(12) United States Patent
Berg et al.

(10) Patent No.: US 7,399,780 B2
(45) Date of Patent: *Jul. 15, 2008

(54) 3-HETEROCYCLYL-INDOLE INHIBITORS OF GLYCOGEN SYNTHASE KINASE-3

(75) Inventors: Stefan Berg, Södertälje (SE); Sven Hellberg, Södertälje (SE); Martin Nylöf, Södertälje (SE); Yafeng Xue, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 417 days.

This patent is subject to a terminal disclaimer.

(21) Appl. No.: 10/509,268

(22) PCT Filed: Mar. 28, 2003

(86) PCT No.: PCT/SE03/00508

§ 371 (c)(1),
(2), (4) Date: Sep. 27, 2004

(87) PCT Pub. No.: WO03/082853

PCT Pub. Date: Oct. 9, 2003

(65) Prior Publication Data

US 2005/0153987 A1 Jul. 14, 2005

(30) Foreign Application Priority Data

Mar. 28, 2002 (SE) .................... 0200979

(51) Int. Cl.
A61K 31/405 (2006.01)
A61K 31/40 (2006.01)
C07D 209/04 (2006.01)
C07D 209/36 (2006.01)

(52) U.S. Cl. ............. 514/415; 514/418; 548/469; 548/484

(58) Field of Classification Search ............ 514/415, 514/418; 548/469, 484
See application file for complete search history.

(56) References Cited

U.S. PATENT DOCUMENTS

| 6,265,411 B1 | 7/2001 | Thomas et al. |
| 6,294,532 B1 | 9/2001 | Thomas et al. |
| 6,987,110 B2 * | 1/2006 | Zhang et al. ............ 514/252.1 |
| 7,205,314 B2 | 4/2007 | Berg et al. |
| 2005/0070559 A1 | 3/2005 | Berg et al. |
| 2005/0075351 A1 | 4/2005 | Berg et al. |
| 2005/0222181 A1 | 10/2005 | Berg et al. |

FOREIGN PATENT DOCUMENTS

| EP | 0667340 A1 | 8/1995 |
| EP | 1136493 A1 | 9/2001 |
| WO | 9515758 A1 | 6/1995 |
| WO | 9523141 A1 | 8/1995 |
| WO | 9533750 A1 | 12/1995 |
| WO | WO-97/42187 A1 | 11/1997 |
| WO | 9910349 A1 | 3/1999 |
| WO | 0010975 A1 | 3/2000 |
| WO | WO-00/71129 A1 | 11/2000 |
| WO | WO-01/25220 A1 | 4/2001 |
| WO | WO-01/32653 A1 | 5/2001 |
| WO | WO-02/10158 A2 | 2/2002 |
| WO | 0230868 A1 | 4/2002 |
| WO | 03053330 A2 | 7/2003 |
| WO | 03053444 A1 | 7/2003 |
| WO | 03055492 A1 | 7/2003 |
| WO | 03055877 A1 | 7/2003 |

OTHER PUBLICATIONS

Co-pending U.S. Appl. No. 10/572,778.*
Bruni, et al (Annali di Chimica, 1967, vol. 57, Issue 6, pp. 688-697, especially p. 693).*
Copending U.S. Appl. No. 10/572,778.*
STN International, File CHEMCATS, accession No. 2001:15770, May 14, 2001, Pharma Library Collection, "2(1H)-Quinoxalinone, 3-(2-hydroxy-1H-indol-3-yl)-", CAS Registry No. RN 312706-99-3.

(Continued)

(Continued)

Primary Examiner—Joseph McKane
Assistant Examiner—Susannah Chung
(74) Attorney, Agent, or Firm—Kenneth F. Mitchell

(57) ABSTRACT

The present invention provides new compounds of formula Ia and Ib: as well as a process for their preparation and new intermediates used therein, pharmaceutical formulations containing said therapeutically active compounds and to the use of said active compounds in therapy.

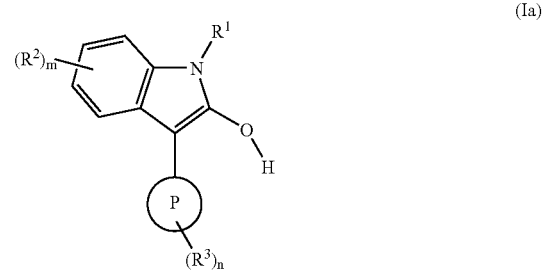

(Ia)

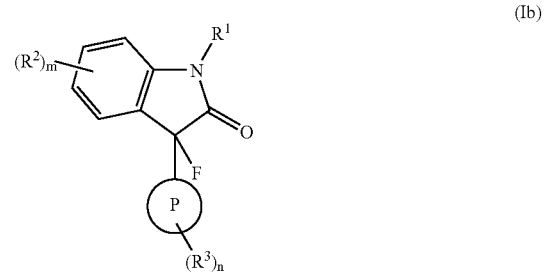

(Ib)

15 Claims, No Drawings

OTHER PUBLICATIONS

STN International, File CAPLUS, CAPLUS accession No. 1967:516779, Document No. 67:116779, Bruni, Paolo et al.: Enolizable cyclic ketones. I. Reaction with activated heteroaromatic N-oxides; & Ann. Chim. (Rome) (1967), 57(6), 688-97.
Ali et al., "Glycogen Synthase Kinase-3: properity, functions, and regulation," Chemical Reviews, Dec. 21, 2000, published online.
"Alzheimers Disease" Wikipedia, online encyclopedia.
Hewawasam et al., "Synthesis and Structure-Activity Relationships of 3-Aryloxindoles: A New Class of Calcium-Dependent, Large Conductance Potassium (Maxi-K) Channel Openers with Neuroprotective Properties," J. Med. Chem., 2002, vol. 45, pp. 1487-1499.
OA issued for U.S. Appl. No. 10/499,685 on Jan. 6, 2006.
Final OA issued for U.S. Appl. No. 10/499,685 on Jul. 20, 2006.
OA issued for U.S. Appl. No. 10/499,685 on Aug. 1, 2007.
OA issued for U.S. Appl. No. 10/499,217 on Jun. 13, 2006.
OA issued for U.S. Appl. No. 10/499,388 on Sep. 20, 2005.
Final OA issued for U.S. Appl. No. 10/499,388 on Oct. 12, 2006.

* cited by examiner

3-HETEROCYCLYL-INDOLE INHIBITORS OF GLYCOGEN SYNTHASE KINASE-3

FIELD OF THE INVENTION

The present invention relates to new compounds of formula Ia and Ib, as a free base or a pharmaceutically acceptable salt thereof, to pharmaceutical formulations containing said compounds and to the use of said compounds in therapy. The present invention further relates to a process for the preparation of compounds of formula Ia and Ib and to new intermediates used therein.

BACKGROUND OF THE INVENTION

Glycogen synthase kinase 3 (GSK3) is a serine/threonine protein kinase composed of two isoforms (α and β), which are encoded by distinct genes but are highly homologous within the catalytic domain. GSK3 is highly expressed in the central and peripheral nervous system. GSK3 phosphorylates several substrates including tau, β-catenin, glycogen synthase, pyruvate dehydrogenase and elongation initiation factor 2b (eIF2b). Insulin and growth factors activate protein kinase B, which phosphorylates GSK3 on serine 9 residue and inactivates it.

Alzheimer's Disease (AD) Dementias, and Taupathies.

AD is characterized by cognitive decline, cholinergic dysfunction and neuronal death, neurofibrillary tangles and senile plaques consisting of amyloid-β deposits. The sequence of these events in AD is unclear, but are believed to be related. Glycogen synthase kinase 3β (GSK3β) or Tau (τ) phosphorylating kinase selectively phosphorylates the microtubule associated protein τ in neurons at sites that are hyperphosphorylated in AD brains. Hyperphosphorylated protein τ has lower affinity for microtubules and accumulates as paired helical filaments, which are the main components that constitute neurofibrillary tangles and neuropil threads in AD brains. This results in depolymerization of microtubules, which leads to dying back of axons and neuritic dystrophy. Neurofibrillary tangles are consistently found in diseases such as AD, amyotrophic lateral sclerosis, parkinsonism-dementia of Gaum, corticobasal degeneration, dementia pugilistica and head trauma, Down's syndrome, postencephalatic parkinsonism, progressive supranuclear palsy, Niemann-Pick's Disease and Pick's Disease. Addition of amyloid-β to primary hippocampal cultures results in hyperphosphorylation of τ and a paired helical filaments-like state via induction of GSK3β activity, followed by disruption of axonal transport and neuronal death (Imahori and Uchida., J. Biochem 121: 179-188, 1997). GSK3β preferentially labels neurofibrillary tangles and has been shown to be active in pre-tangle neurons in AD brains. GSK3 protein levels are also increased by 50% in brain tissue from AD patients. Furthermore, GSK3β phosphorylates pyruvate dehydrogenase, a key enzyme in the glycolytic pathway and prevents the conversion of pyruvate to acetyl-Co-A (Hoshi et al., PNAS 93:2719-2723, 1996). Acetyl-Co-A is critical for the synthesis of acetylcholine, a neurotransmitter with cognitive functions. Thus, GSK3β inhibition may have beneficial effects in progression as well as the cognitive deficits associated with Alzheimer's disease and other above-referred to diseases.

Chronic and Acute Neurodegenerative Diseases.

Growth factor mediated activation of the PI3K /Akt pathway has been shown to play a key role in neuronal survival. The activation of this pathway results in GSK3β inhibition. Recent studies (Bhat et. al., PNAS 97:11074-11079 (2000)) indicate that GSK3β activity is increased in cellular and animal models of neurodegeneration such as cerebral ischemia or after growth factor deprivation. For example, the active site phosphorylation was increased in neurons vulnerable to apoptosis, a type of cell death commonly thought to occur in chronic and acute degenerative diseases such as Alzheimer's Disease, Parkinson's Disease, amyotrophic lateral sclerosis, Huntington's Disease and HIV dementia, ischemic stroke and head trauma. Lithium was neuroprotective in inhibiting apoptosis in cells and in the brain at doses that resulted in the inhibition of GSK3β. Thus GSK3β inhibitors could be useful in attenuating the course of neurodegenerative diseases.

Bipolar Disorders (BD)

Bipolar Disorders are characterised by manic episodes and depressive episodes. Lithium has been used to treat BD based on its mood stabilising effects. The disadvantage of lithium is the narrow therapeutic window and the danger of overdosing that can lead to lithium intoxication. The recent discovery that lithium inhibits GSK3 at therapeutic concentrations has raised the possibility that this enzyme represents a key target of lithium's action in the brain (Stambolic et al., Curr. Biol. 6:1664-1668, 1996; Klein and Melton; PNAS 93:8455-8459, 1996). Inhibition of GSK3β may therefore be of therapeutic relevance in the treatment of BD as well as in AD patients that have affective disorders.

Schizophrenia

GSK3 is involved in signal transduction cascades of multiple cellular processes, particularly during neural development. Kozlovsky et al (Am J Psychiatry 2000 May;157(5): 831-3) found that GSK3β levels were 41% lower in the schizophrenic patients than in comparison subjects. This study indicates that schizophrenia involves neurodevelopmental pathology and that abnormal GSK3 regulation could play a role in schizophrenia. Furthermore, reduced β-catenin levels have been reported in patients exhibiting schizophrenia (Cotter et al., Neuroreport 9:1379-1383 (1998)).

Diabetes

Insulin stimulates glycogen synthesis in skeletal muscles via the dephosphorylation and thus activation of glycogen synthase. Under resting conditions, GSK3 phosphorylates and inactivates glycogen synthase via dephosphorylation. GSK3 is also over-expressed in muscles from Type II diabetic patients (Nikoulina et al., Diabetes 2000 February;49(2):263-71). Inhibition of GSK3 increases the activity of glycogen synthase thereby decreasing glucose levels by its conversion to glycogen. GSK3 inhibition may therefore be of therapeutic relevance in the treatment of Type I and Type II diabetes and diabetic neuropathy.

Hair Loss

GSK3 phosphorylates and degrades β-catenin. β-catenin is an effector of the pathway for keratonin synthesis. β-catenin stabilisation may be lead to increase hair development. Mice expressing a stabilised β-catenin by mutation of sites phosphorylated by GSK3 undergo a process resembling de novo hair morphogenesis (Gat et al., Cell 1998 November 25;95 (5):605-14)). The new follicles formed sebaceous glands and dermal papilla, normally established only in embryogenesis. Thus GSK3 inhibition may offer treatment for baldness.

Oral Contraceptives

Vijaraghavan et al. (Biol Reprod 2000 June; 62 (6):1647-54) reported that GSK3 is high in motile versus immotile sperm. Immunocytochemistry revealed that GSK3 is present in the flagellum and the anterior portion of the sperm head.

These data suggest that GSK3 could be a key element underlying motility initiation in the epididymis and regulation of mature sperm function. Inhibitors of GSK3 could be useful as contraceptives for males.

DISCLOSURE OF THE INVENTION

The object of the present invention is to provide compounds having an inhibiting effect on GSK3 as well as having a good bioavailability.

1. Accordingly, the present invention provides compounds of of formula Ia and Ib:

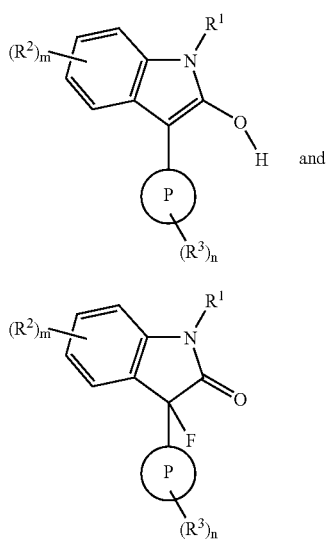

wherein:

P represents a 5- or 6-membered heteroaromatic ring containing one or two heteroatoms selected independently from N, O and S of which at least one atom is nitrogen;

$R^1$ is hydrogen;

$R^2$ and $R^3$ are independently selected from halogen, nitro, $C_{1-6}$alkyl, $C_{2-6}$alkenyl, $C_{2-6}$alkynyl, $C_{0-6}$alkyl$C_{3-6}$cycloalkyl, $C_{0-6}$alkylaryl, $C_{0-6}$alkylheteroaryl, CHO, $C_{0-6}$alkylOR$^4$, OC$_{1-6}$alkylOR$^4$, $C_{0-6}$alkylSR$^4$, OC$_{1-6}$alkylSR$^4$, (CO)R$^4$, (CO)OR$^4$, O(CO)R$^4$, fluoromethyl, difluoromethyl, trifluoromethyl, fluoromethoxy, difluoromethoxy, trifluoromethoxy, OC$_{1-6}$alkylcyano, $C_{0-6}$alkylcyano, $C_{1-6}$alkylCO$_2$R$^4$, OC$_{1-6}$alkylCO$_2$R$^4$, O(CO)OR$^4$, OC$_{1-6}$alkylCOR$^4$, $C_{1-6}$alkylCOR$^4$, NR$^4$OR$^5$, $C_{0-6}$alkylNR$^4$R$^5$, OC$_{1-6}$alkylNR$^4$R$^5$, $C_{0-6}$alkylCONR$^4$R$^5$, OC$_{1-6}$alkylCONR$^4$R$^5$, OC$_{1-6}$alkylNR$^4$(CO)R$^5$, $C_{0-6}$alkylNR$^4$(CO)R$^5$, $C_{0-6}$alkylNR$^4$(CO)NR$^4$R$^5$, O(CO)NR$^4$R$^5$, NR$^4$(CO)OR$^5$, $C_{0-6}$alkyl(SO$_2$)NR$^4$R$^5$, OC$_{1-6}$alkyl(SO$_2$)NR$^4$R$^5$, $C_{0-6}$alkylNR$^4$(SO$_2$)R$^5$, OC$_{1-6}$alkylNR$^4$(SO$_2$)R$^5$, $C_{0-6}$alkyl(SO)NR$^4$R$^5$, OC$_{1-6}$alkyl(SO)NR$^4$R$^5$, SO$_3$R$^4$, $C_{0-6}$alkylNR$^4$(SO$_2$)NR$^4$R$^5$, $C_{0-6}$alkylNR$^4$(SO)R$^5$, OC$_{0-6}$alkylNR$^4$(SO)R$^5$, OC$_{0-6}$alkylSO$_2$R$^4$, $C_{0-6}$alkylSO$_2$R$^4$, $C_{0-6}$alkylSOR$^4$, OC$_{1-6}$alkylSOR$^4$ and a group X$^1$R$^6$, wherein X$^1$ is a direct bond, O, CONR$^7$R$^8$, SO$_2$NR$^9$R$^{10}$, SO$^2$R$^{11}$ or NR$^{12}$R$^{13}$; and wherein R$^6$ is linked to R$^8$, R$^{10}$, R$^{11}$ and R$^{13}$;

$R^7$, $R^9$ and $R^{12}$ each independently are hydrogen or $C_{1-6}$alkyl;

$R^8$, $R^{10}$, $R^{11}$ and $R^{13}$ are $C_{1-6}$alkyl;

$R^6$ is phenyl or a 5-, 6- or 7-membered heterocyclic group containing one or two heteroatoms, selected independently from N, O and S, which heterocyclic group may be saturated or unsaturated or said phenyl or 5-, 6- or 7-membered heterocyclic group may optionally be fused with a 5- or 6-membered saturated or unsaturated ring containing atoms selected independently from C, N, O and S and which phenyl or heterocyclic group may be substituted with one or two substituents selected from W;

m is 0, 1, 2, 3 or 4;

n is 0, 1, 2, 3 or 4;

$R^4$ is selected from hydrogen, $C_{1-6}$alkyl, $C_{2-6}$alkenyl, $C_{2-6}$alkynyl, $C_{0-6}$alkyl$C_{3-6}$cycloalkyl, $C_{0-6}$alkylaryl, $C_{0-6}$alkylheteroaryl, $C_{1-6}$alkylNR$^{14}$R$^{15}$ and a 5- or 6-membered heterocyclic group containing one or two heteroatoms, selected independently from N, O and S, wherein said heterocyclic group may optionally be substituted by a group Y;

$R^5$ is selected from hydrogen, $C_{1-6}$alkyl, $C_{2-6}$alkenyl, $C_{2-6}$alkynyl, $C_{0-6}$alkyl$C_{3-6}$cycloalkyl, $C_{0-6}$alkylaryl, $C_{0-6}$alkylheteroaryl and $C_{1-6}$alkylNR$^{14}$R$^{15}$ and; wherein $R^4$ and $R^5$ may together form a 4-, 5-, 6- or 7-membered heterocyclic group containing one or more heteroatoms selected independently from N, O and S, wherein said heterocyclic group may optionally be substituted by a group Y; and wherein any $C_{1-6}$alkyl, $C_{2-6}$alkenyl, $C_{2-6}$alkynyl, $C_{0-6}$alkyl$C_{3-6}$cycloalkyl, $C_{0-6}$alkylaryl; and $C_{0-6}$alkylheteroaryl defined under $R^2$ to $R^5$ may be substituted by one or more group Z;

$R^{14}$ and $R^{15}$ are independently selected from hydrogen, $C_{1-6}$alkyl and $C_{0-6}$alkyl$C_{3-6}$cycloalkyl and wherein $R^{14}$ and $R^{15}$ may together form a 5- or 6-membered heterocyclic group containing one or more heteroatoms, selected independently from N, O and S, wherein said heterocyclic group may optionally be substituted by a group Y;

W and Z are independently selected from oxo, halogen, nitro, CN, OR$^{16}$, $C_{1-6}$alkyl, $C_{0-6}$alkylaryl, $C_{0-6}$alkyl$C_{3-6}$cycloalkyl, fluoromethyl, difluoromethyl, trifluoromethyl, fluoromethoxy, difluoromethoxy, trifluoromethoxy, OC$_{1-6}$alkylNR$^{16}$R$^{17}$, NR$^{16}$R$^{17}$, CONR$^{16}$R$^{17}$, NR$^{16}$(CO)R$^{17}$, O(CO)C$_{1-6}$alkyl, (CO)OC$_{1-6}$alkyl, COR$^{16}$, (SO$_2$)NR$^{16}$R$^{17}$, SO$_2$R$^{16}$, SOR$^{16}$, (CO)C$_{1-6}$alkylNR$^{16}$R$^{17}$, (SO$_2$)C$_{1-6}$alkylNR$^{16}$R$^{17}$, a 5- or 6-membered heterocyclic group containing one or two heteroatoms, selected independently from N, O and S, phenyl and heteroaryl, which heterocyclic group, phenyl or heteroaryl may optionally be substituted by a group Y;

Y is selected from oxo, halogen, nitro, CN, OR$^{16}$, $C_{1-6}$alkyl, $C_{0-6}$alkylaryl, $C_{0-6}$alkyl$C_{3-6}$cycloalkyl, fluoromethyl, difluoromethyl, trifluoromethyl, fluoromethoxy, difluoromethoxy, trifluoromethoxy, OC$_{1-6}$alkylNR$^{16}$R$^{17}$, NR$^{16}$R$^{17}$, CONR$^{16}$R$^{17}$, NR$^{16}$(CO)R$^{17}$, O(CO)C$_{1-6}$alkyl, (CO)OC$_{1-6}$alkyl, COR$^{16}$, (SO$_2$)NR$^{16}$R$^{17}$, SO$_2$R$^{16}$, SOR$^{16}$, (CO)C$_{1-6}$alkylNR$^{16}$R$^{17}$, (SO$_2$)C$_{1-6}$alkylNR$^{16}$R$^{17}$, phenyl, $C_{0-6}$alkylaryl and heteroaryl wherein the phenyl, $C_{0-6}$alkylaryl and heteroaryl group may be optionally substituted with halogen, nitro, CN, OR$^{16}$, $C_{1-6}$alkyl, fluoromethyl, difluoromethyl, trifluoromethyl, fluoromethoxy, difluoromethoxy and trifluoromethoxy;

$R^{16}$ and $R^{17}$ are independently selected from hydrogen and $C_{1-6}$alkyl and wherein $R^{16}$ and $R^{17}$ may together form a 5- or 6-membered heterocyclic group containing one or more heteroatoms, selected independently from N, O and S;

as a free base or a pharmaceutically acceptable salt thereof.

In one aspect of the invention there is provided compounds of Formula Ia and Ib wherein P is a 6-membered heteroaromatic ring containing one or two nitrogen atoms.

In a first embodiment of this aspect of the invention there is provided compounds of Formula Ia and Ib, wherein P is pyridine.

In another embodiment of this aspect of the invention there is provided compounds of Formula Ia and Ib, wherein P is pyrimidine.

In another aspect of the invention there is provided compounds of Formula Ia.

In yet another aspect of the invention there is provided compounds of Formula Ia and Ib wherein $R^2$ and $R^3$ are independently selected from: halogen, nitro, $C_{0-6}$alkylheteroaryl, trifluoromethyl, $C_{0-6}$alkylcyano, $C_{0-6}$alkylNR$^4$R$^5$, $C_{0-6}$alkylCONR$^4$R$^5$, $OC_{1-6}$alkylNR$^4$R$^5$, $OC_{1-6}$alkylNR$^4$R$^5$, $C_{0-6}$alkyl(SO$_2$)NR$^4$R$^5$, and a group $X^1R^6$, wherein $X^1$ is a direct bond; $R^6$ is a 5-membered heterocyclic group containing one or two heteroatoms, selected independently from N, O and S, and which heterocyclic group may be substituted with one or two substituents W, preferably $C_{1-6}$alkyl; m is 0, 1, 2; and n is 1 or 2.

In yet another aspect of the invention there is provided compounds of Formula Ia and Ib wherein $R^4$ is independently selected from hydrogen, $C_{1-6}$alkyl, $C_{0-6}$alkylC$_{3-6}$cycloalkyl, $C_{0-6}$alkylaryl, $C_{0-6}$alkylheteroaryl, $C_{1-6}$alkylNR$^{14}$R$^{15}$ and a 5- or 6-membered heterocyclic group containing one or two heteroatoms, selected independently from N, O and S, wherein said heterocyclic group may optionally be substituted by a group Y; $R^5$ is selected from hydrogen, $C_{1-6}$alkyl; wherein $R^4$ and $R^5$ may together form a 4-, 5-, 6- or 7-membered heterocyclic group containing one or more heteroatoms selected independently from N, O and S, wherein said heterocyclic group may optionally be substituted by a group Y; and wherein any $C_{1-6}$alkyl, $C_{0-6}$alkylaryl defined under $R^2$ to $R^5$ may be substituted by one or more group Z; $R^{14}$ and $R^{15}$ are independently $C_{1-6}$alkyl and wherein $R^{14}$ and $R^{15}$ may together form a 5- or 6-membered heterocyclic group containing one or more heteroatoms, selected independently from N, O and S; Z is independently selected from, halogen, $C_{1-6}$alkyl, CN, NR$^{16}$R$^{17}$; Y is selected from $C_{1-6}$alkyl, $C_{0-6}$alkylaryl, NR$^{16}$R$^{17}$, phenyl, wherein the phenyl may be optionally substituted with nitro and trifluoromethyl; $R^{16}$ and $R^{17}$ are $C_{1-6}$alkyl and wherein $R^{16}$ and $R^{17}$ may together form a 5- or 6-membered heterocyclic group containing one or more heteroatoms, selected independently from N, O and S.

In yet another aspect of the invention there is provided compounds of Formula Ia and Ib wherein P is pyridine; $R^1$ is hydrogen; $R^2$ is CN; $R^3$ is $C_{0-6}$alkylNR$^4$R$^5$; wherein $R^4$ and $R^5$ may together form a 4-, 5-, 6- or 7-membered heterocyclic group containing one or more heteroatoms selected independently from N, O and S.

Yet another aspect of the invention relates to compounds selected from:

2-(5-Cyano-2-hydroxy-1H-indol-3-yl)-N-[2-(dimethylamino)ethyl]isonicotinamide;
2-Hydroxy-3-{4-[(4-methylpiperazin-1-yl)carbonyl]pyridin-2-yl}-1H-indole-5-carbonitrile hydrochloride;
2-Hydroxy-3-{5-[(4-methylpiperazin-1-yl)carbonyl]pyridin-2-yl}-1H-indole-5-carbonitrile;
2-Hydroxy-3-[5-(morpholin-4-ylmethyl)pyridin-2-yl]-1H-indole-5-carbonitrile hydrochloride;
2-Hydroxy-3-[6-(2-morpholin-4-ylethoxy)pyrimidin-4-yl]-1H-indole-5-carbonitrile;
2-Hydroxy-3-{5-[(4-methylpiperazin-1-yl)methyl]pyridin-2-yl}-1H-indole-5-carbonitrile hydrochloride;
6-(5-Cyano-2-hydroxy-1H-indol-3-yl)-N-[2-(dimethylamino)ethyl]-N-methylnicotinamide hydrochloride;
2-Hydroxy-3-{5-[(4-methylpiperazin-1-yl)sulfonyl]pyridin-2-yl}-1H-indole-5-carbonitrile hydrochloride;
6-(5-Cyano-2-hydroxy-1H-indol-3-yl)-N-(2-pyrrolidin-1-ylethyl)pyridine-3-sulfonamide hydrochloride;
2-Hydroxy-3-[5-(morpholin-4-ylmethyl)pyridin-2-yl]-1H-indole-5-carbonitrile;
2-Hydroxy-3-[5-(pyrrolidin-1-ylmethyl)pyridin-2-yl]-1H-indole-5-carbonitrile hydrochloride;
2-Hydroxy-3-{5-[(4-methyl-1,4-diazepan-1-yl)methyl]pyridin-2-yl}-1H-indole-5-carbonitrile hydrochloride;
2-Hydroxy-3-{5-[(4-pyrrolidin-1-ylpiperidin-1-yl)methyl]pyridin-2-yl)-1H-indole-5-carbonitrile hydrochloride;
3-(5-{[3-(Dimethylamino)pyrrolidin-1-yl]methyl}pyridin-2-yl)-2-hydroxy-1H-indole-5-carbonitrile;
2-Hydroxy-3-{5-[(4-methylpiperidin-1-yl)methyl]pyridin-2-yl}-1H-indole-5-carbonitrile;
2-Hydroxy-3-{5-[(4-phenylpiperazin-1-yl)methyl]pyridin-2-yl}-1H-indole-5-carbonitrile;
3-[5-(Azetidin-1-ylmethyl)pyridin-2-yl]-2-hydroxy-1H-indole-5-carbonitrile;
2-Hydroxy-3-[5-({4-[2-nitro-4-(trifluoromethyl)phenyl]piperazin-1-yl}methyl)pyridin-2-yl]-1H-indole-5-carbonitrile;
3-(5-{[(2-Cyanoethyl)(ethyl)amino]methyl}pyridin-2-yl)-2-hydroxy-1H-indole-5-carbonitrile;
3-(5-{[(4-Chlorobenzyl)(methyl)amino]methyl}pyridin-2-yl)-2-hydroxy-1H-indole-5-carbonitrile;
3-(5-{[(2-Furylmethyl)(methyl)amino]methyl}pyridin-2-yl)-2-hydroxy-1H-indole-5-carbonitrile;
2-Hydroxy-3-(5-{[methyl(phenyl)amino]methyl}pyridin-2-yl)-1H-indole-5-carbonitrile;
2-Hydroxy-3-{5-[(3-methylpiperidin-1-yl)methyl]pyridin-2-yl}-1H-indole-5-carbonitrile;
3-(5-{[Cyclohexyl(methyl)amino]methyl}pyridin-2-yl)-2-hydroxy-1H-indole-5-carbonitrile;
2-Hydroxy-3-[5-(piperidin-1-ylmethyl)pyridin-2-yl]- H-indole-5-carbonitrile;
3-{5-[(4-Methylpiperazin-1-yl)sulfonyl]pyridin-2-yl}-1H-indol-2-ol hydrochloride;
6-Chloro-3-{5-[(4-methylpiperazin-1-yl)sulfonyl]pyridin-2-yl}-1H-indol-2-ol hydrochloride;
3-[5-(Morpholin-4-ylcarbonyl)pyridin-2-yl]-5-nitro-1H-indol-2-ol;
6-Bromo-3-[5-(morpholin-4-ylmethyl)pyridin-2-yl]-1H-indol-2-ol hydrochloride;
2-Hydroxy-3-[5-(morpholin-4-ylmethyl)pyridin-2-yl]-1H-indole-6-carbonitrile hydrochloride;
5-Bromo-3-[5-(morpholin-4-ylmethyl)pyridin-2-yl]-1H-indol-2-ol hydrochloride;
5,6-Dibromo-3-[5-(morpholin-4-ylmethyl)pyridin-2-yl]-1H-indol-2-ol hydrochloride;
3-Fluoro-3-[5-(morpholin-4-ylmethyl)pyridin-2-yl]-2-oxoindoline-6-carbonitrile hydrochloride;
3-{5-[(4-Benzylpiperazin-1-yl)sulfonyl]pyridin-2-yl}-2-hydroxy-1H-indole-5-carbonitrile hydrochloride;
2-Hydroxy-3-(5-{[4-(3-methylbutyl)piperazin-1-yl]sulfonyl}pyridin-2-yl)-1H-indole-5-carbonitrile hydrochloride;
2-Hydroxy-3-(5-[(4-isopropylpiperazin-1-yl)sulfonyl]pyridin-2-yl}-1H-indole-5-carbonitrile hydrochloride;
3-{5-[(4-Ethylpiperazin-1-yl)sulfonyl]pyridin-2-yl}-2-hydroxy-1H-indole-5-carbonitrile hydrochloride;
3-[5-(Morpholin-4-ylmethyl)pyridin-2-yl]-5-pyidin-3-yl-1H-indol-2-ol;
3-[5-(Morpholin-4-ylmethyl)pyridin-2-yl]-5-thien-2-yl-1H-indol-2-ol hydrochloride;
5-(2-Furyl)-3-[5-(morpholin-4-ylmethyl)pyridin-2-yl]-1H-indol-2-ol hydrochloride;

3-{3-Bromo-5-[(4-methylpiperazin-1-yl)sulfonyl]pyridin-2-yl}-5-nitro-1H-indol-2-ol hydrochloride;
3-[5-(Morpholin-4-ylmethyl)pyridin-2-yl]-5-(trifluoromethyl)-1H-indol-2-ol hydrochloride;
2-Hydroxy-3-{5-[(4-methylpiperazin-1-yl)sulfonyl]pyridin-2-yl}-1H-indole-6-carbonitrile hydrochloride;
N-[(1-Ethylpyrrolidin-2-yl)methyl]-6-(2-hydroxy-5-nitro-1H-indol-3-yl)nicotinamide hydrochloride;
6-(2-Hydroxy-5-nitro-1H-indol-3-yl)-N-(2-morpholin-4-ylethyl)nicotinamide hydrochloride;
6-(2-Hydroxy-5-nitro-1H-indol-3-yl)-N-methyl-N-(1-methylpiperidin-4-yl)nicotinamide hydrochloride;
5-Nitro-3-{5-[(4-pyrrolidin-1-ylpiperidin-1-yl)carbonyl]pyridin-2-yl}-1H-indol-2-ol hydrochloride;
3-(5-{[3-(Dimethylamino)pyrrolidin-1-yl]carbonyl}pyridin-2-yl)-5-nitro-1H-indol-2-ol hydrochloride;
N-[2-(Dimethylamino)-1-methylethyl]-6-(2-hydroxy-5-nitro-1H-indol-3-yl)nicotinamide hydrochloride;
6-(2-Hydroxy-5-nitro-1H-indol-3-yl)-N-(2-pyrollindin-1-ylethyl)nicotinamide fumarate;
3-{5-[(4-Methylpiperazin-1-yl)carbonyl]pyridin-2-yl}-5-nitro-1H-indol-2-ol fumarate;
6-(5-Cyano-2-hydroxy-1H-indol-3-yl)-N-(2-pyrrolidin-1-ylethyl)nicotinamide fumarate;
6-(5-Cyano-2-hydroxy-1H-indol-3-yl)-N-methyl-N-(2-pyrrolidin-1-ylethyl)pyridine-3-sulfonamide hydrochloride;
6-(5-Cyano-2-hydroxy-1H-indol-3-yl)-N-[2-(dimethylamino)ethyl]pyridine-3-sulfonamide fumarate;
6-(5-Cyano-2-hydroxy-1H-indol-3-yl)-N-[2-(dimethylamino)ethyl]-N-ethylpyridine-3-sulfonamide fumarate;
6-(5-Cyano-2-hydroxy-1H-indol-3-yl)-N-[(1-ethylpyrrolidin-2-yl)methyl]pyridine-3-sulfonamide fumarate;
2-Hydroxy-3-{5-[(4-methyl-1,4-diazepan-1-yl)sulfonyl]pyridin-2-yl}-1H-indole-5-carbonitrile fumarate;
2-Hydroxy-3-[5-(morpholin-4-ylsulfonyl)pyridin-2-yl]-1H-indole-5-carbonitrile;
3-{5-[(4-Methylpiperazin-1-yl)sulfonyl]pyridin-2-yl}-5-(2-methyl-1,3-thiazol-4-yl)-1H-indol-2-ol hydrochloride;
3-{5-[(4-Methylpiperazin-1-yl)sulfonyl]pyridin-2-yl}-5-(1,3-thiazol-4-yl)-1H-indol-2-ol fumarate;
3-{5-[(4-Methylpiperazin-1-yl)sulfonyl]pyridin-2-yl}-5-(1,3-oxazol-5-yl)-1H-indol-2-ol;
3-[5-(Morpholin-4-ylmethyl)pyridin-2-yl]-5-nitro-1H-indol-2-ol hydrochloride.

Listed below are definitions of various terms used in the specification and claims to describe the present invention.

For the avoidance of doubt it is to be understood that where in this specification a group is qualified by 'hereinbefore defined', 'defined hereinbefore' or 'defined above' the said group encompasses the first occurring and broadest definition as well as each and all of the other definitions for that group.

For the avoidance of doubt it is to be understood that in this specification '$C_{0-6}$' means a carbon group having 0, 1, 2, 3, 4, 5 or 6 carbon atoms.

For the avoidance of doubt it is to be understood that in this specification '$C_{1-6}$' means a carbon group having 1, 2, 3, 4, 5 or 6 carbon atoms.

In this specification, unless stated otherwise, the term "alkyl" includes both straight and branched chain alkyl groups and may be, but is not limited to, methyl, ethyl, n-propyl, i-propyl, n-butyl, i-butyl, s-butyl, t-butyl, n-pentyl, i-pentyl, t-pentyl, neo-pentyl, n-hexyl or i-hexyl, t-hexyl.

In this specification, unless stated otherwise, the term "cycloalkyl" refers to an optionally substituted, saturated cyclic hydrocarbon ring system. The term "$C_{3-6}$cycloalkyl" may be, but is not limited to, cyclopropyl, cyclobutyl, cyclopentyl or cyclohexyl.

In this specification, unless stated otherwise, the term "alkylaryl", includes both substituted and unsubstituted alkylaryl groups, which may be substituted on the alkyl and/or the aryl and may be, but are not limited to, $C_{1-6}$alkylaryl, benzyl or ethylphenyl.

In this specification, unless stated otherwise, the term "heteroaryl" may be a monocyclic heteroaromatic, or a bicyclic fused-ring heteroaromatic group. Examples of said heteroaryl include, but are not limited to, pyridyl, pyrrolyl, furyl, thienyl, imidazolyl, oxazolyl, isoxazolyl, thiazolyl, pyrazolyl, benzofuryl, indolyl, isoindolyl, benzimidazolyl, pyridazinyl, pyrimidinyl, pyrazinyl, tetrazolyl and triazolyl.

In this specification, unless stated otherwise, the term "alkenyl" includes both straight and branched chain alkenyl groups but references to individual alkenyl groups such as 2-butenyl are specific for the straight chain version only. The term $C_2$-$C_6$ alkenyl having 2 to 6 carbon atoms and one or two double bonds, and may be, but is not limited to, vinyl, allyl, propenyl, i-propenyl, butenyl, i-butenyl, crotyl, pentenyl, i-pentenyl or hexenyl.

In this specification, unless stated otherwise, the term "alkynyl" includes both straight and branched chain alkynyl groups but references to individual alkynyl groups such as 2-butynyl are specific for the straight chain version only. The term $C_2$-$C_6$ alkynyl having 2 to 6 carbon atoms and one or two trippel bonds, and may be, but is not limited to, etynyl, propargyl, butynyl, i-butynyl, pentynyl, i-pentynyl or hexynyl.

In this specification, unless stated otherwise, the term "5- or 6-membered heteroaromatic ring containing one or two heteroatoms selected independently from N, O and S of which at least one atom is selected from nitrogen" includes, but is not limited to, isoxazolyl, isothiazolyl, oxazolyl, pyrazinyl, pyrazolyl, pyridazinyl, pyridyl, pyriridyl, pyrrolyl, thiazolyl, imidazolyl.

In this specification, unless stated otherwise, the terms "5- or 6-membered heterocyclic group containing one or more heteroatoms, selected independently from N, O and S" or "5-, 6- or 7-membered heterocyclic group containing one or two heteroatoms, selected independently from N, O and S, which heterocyclic group may be saturated or unsaturated" or "4-, 5-, 6- or 7-membered heterocyclic group containing one or more heteroatoms selected independently from N, O and S" may be, but are not limited to, azepanyl, azitidinyl, imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl, thiomorpholinyl, furyl, isoxazolyl, isothiazolyl, oxazolyl, pyrazinyl, pyrazolyl, pyridazinyl, pyridyl, pyrimidyl, pyrrolyl, thiazolyl, thienyl, imidazolyl.

In this specification, unless stated otherwise, the term "5- or 6-membered saturated or unsaturated ring containing atoms selected independently from C, N, O and S", includes both aromatic, heteroaromatic rings and heterocyclic rings that are saturated or unsaturated. Examples of such heterocyclic rings may be, but are not limited to furyl, isoxazolyl, isothiazolyl, oxazolyl, pyrazinyl, pyrazolyl, pyridazinyl, pyridyl, pyrimidyl, pyrrolyl, thiazolyl, thienyl, imidazolyl, imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl, thiomorpholinyl, phenyl, cyclohexyl or cyclopentyl.

In this specification, unless stated otherwise, the term "6-membered heteroaromatic ring containing one or two nitrogen atoms" includes, but is not limited to, pyrazinyl, pyridazinyl, pyridyl or pyrimidyl.

In this specification, unless stated otherwise, the term "5-membered heterocyclic group containing one or two heteroatoms atoms, selected independently from N, O and S" includes, but is not limited to, pyrazolyl, pyrrolyl, thiazolyl, oxazolyl, thienyl, furyl, imidazolyl, isothiazolyl or isoxazolyl.

In the case where a subscript is the integer 0 (zero) the group to which the subscript refers to, indicates that the group is absent, i.e. there is a direct bond between the groups.

In this specification, unless stated otherwise, the term halogen may be fluorine, chlorine, bromine or iodine.

The present invention relates to the use of compounds of formula Ia and Ib as hereinbefore defined as well as to the salts thereof. Salts for use in pharmaceutical compositions will be pharmaceutically acceptable salts, but other salts may be useful in the production of the compounds of formula Ia and Ib.

Both organic and inorganic acids can be employed to form non-toxic pharmaceutically acceptable salts of the compounds of this invention. Pharmaceutically acceptable salts include, but are not limited to hydrochloride, and fumarate. These salts are readily prepared by methods known in the art.

Some compounds of formula Ia and Ib may have chiral centres and/or geometric isomeric centres (E- and Z-isomers), and it is to be understood that the invention encompasses all such optical, diastereoisomeric and geometric isomers.

Within the present invention it is to be understood that a compound of formula Ia or a salt thereof may exhibit the phenomenon of tautomerism as shown in FIG. 1. It is to be understood that the invention encompasses any tautomeric form of compounds of formula Ia and is not to be limited merely to any one tautomeric form utilized within the formula drawings:

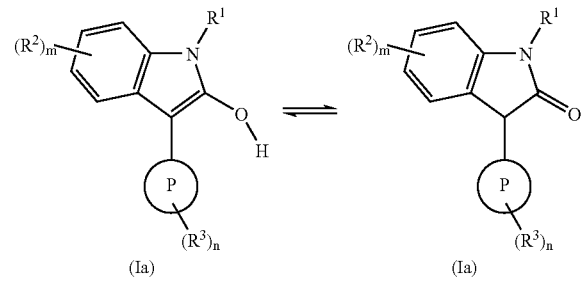

wherein P, $R^1$, $R^2$, $R^3$, m and n are as defined above.

An object of the invention is to provide compounds of formula Ia or Ib for therapeutic use, especially compounds that are useful for the prevention and/or treatment of conditions associated with glycogen synthase kinase-3 (GSK3) in mammals including man. Particularly, compounds of formula Ia or Ib exhibiting a selective affinity for GSK-3.

Pharmaceutical Compositions

According to one aspect of the present invention there is provided a pharmaceutical composition comprising a compound of formula Ia or Ib, as a free base or a pharmaceutically acceptable salt thereof, for use in the prevention and/or treatment of conditions associated with glycogen synthase kinase-3.

The composition may be in a form suitable for oral administration, for example as a tablet, for parenteral injection as a sterile solution or suspension. In general the above compositions may be prepared in a conventional manner using pharmaceutically carriers or diluents. Suitable daily doses of the compounds of formula Ia or Ib in the treatment of a mammal, including man, are approximately 0.01 to 250 mg/kg bodyweight at peroral administration and about 0.001 to 250 mg/kg bodyweight at parenteral administration. The typical daily dose of the active ingredients varies within a wide range and will depend on various factors such as the relevant indication, the route of administration, the age, weight and sex of the patient and may be determined by a physician.

A compound of formula Ia or Ib, or a pharmaceutically acceptable salt thereof, can be used on its own but will usually be administered in the form of a pharmaceutical composition in which the formula Ia or Ib compound/salt (active ingredient) is in association with a pharmaceutically acceptable diluent or carrier. Dependent on the mode of administration, the pharmaceutical composition may comprise from 0.05 to 99% w (per cent by weight), for example from 0.10 to 50% w, of active ingredient, all percentages by weight being based on total composition.

A diluent or carrier includes water, aqueous polyethylene glycol, magnesium carbonate, magnesium stearate, talc, a sugar (such as lactose), pectin, dextrin, starch, tragacanth, microcrystalline cellulose, methylcellulose, sodium carboxymethyl cellulose or cocoa butter.

A composition of the invention can be in tablet or injectable form. The tablet may additionally comprise a disintegrant and/or may be coated (for example with an enteric coating or coated with a coating agent such as hydroxypropyl methylcellulose).

The invention further provides a process for the preparation of a pharmaceutical composition of the invention which comprises mixing a compound of formula I, or a pharmaceutically acceptable salt thereof, a hereinbefore defined, with a pharmaceutically acceptable diluent or carrier.

An example of a pharmaceutical composition of the invention is an injectable solution containing a compound of the invention, or a a pharmaceutically acceptable salt thereof, as hereinbefore defined, and sterile water, and, if necessary, either sodium hydroxide or hydrochloric acid to bring the pH of the final composition to about pH 5, and optionally a surfactant to aid dissolution.

Liquid solution comprising a compound of formula Ia or Ib, or a salt thereof, dissolved in water.

| Solution | mg/mL |
|---|---|
| Active Compound | 5.0% w/v |
| Pure water | To 100% |

Medical Use

Surprisingly, it has been found that the compounds defined in the present invention, as a free base or a pharmaceutically acceptable salt thereof, are well suited for inhibiting glycogen synthase kinase-3 (GSK3). Accordingly, the compounds of the present invention are expected to be useful in the prevention and/or treatment of conditions associated with glycogen synthase kinase-3 activity, i.e. the compounds may be used to produce an inhibitory effect of GSK3 in mammals, including man, in need of such prevention and/or treatment.

GSK3 is highly expressed in the central and peripheral nervous system and in other tissues. Thus, it is expected that compounds of the invention are well suited for the prevention and/or treatment of conditions associated with glycogen synthase kinase-3 in the central and peripheral nervous system.

In particular, the compounds of the invention are expected to be suitable for prevention and/or treatment of conditions associated with especially, dementia, Alzheimer's Disease, Parkinson's Disease, Frontotemporal dementia Parkinson's Type, Parkinson dementia complex of Guam, HIV dementia, diseases with associated neurofibrillar tangle pathologies and dementia pugilistica.

Other conditions are selected from the group consisting of amyotrophic lateral sclerosis, corticobasal degeneration, Down syndrome, Huntington's Disease, postencephelatic parkinsonism, progressive supranuclear palsy, Pick's Disease, Niemann-Pick's Disease, stroke, head trauma and other chronic neurodegenerative diseases, Bipolar Disease, affective disorders, depression, schizophrenia, cognitive disorders, hair loss and contraceptive medication.

Further conditions are selected from the group consisting predemented states, Mild Cognitive Impairment, Age-Associated Memory Impairment, Age-Related Cognitive Decline, Cognitive Impairement No Dementia, mild cognitive decline, mild neurocognitive decline, Late-Life Forgetfulness, memory impairment and cognitive impairment, vascular dementia, dementia with Lewy bodies and androgenetic alopecia.

One embodiment of the invention relates to the prevention and/or treatment of dementia and Alzheimer's Disease.

The dose required for the therapeutic or preventive treatment of a particular disease will necessarily be varied depending on the host treated, the route of administration and the severity of the illness being treated.

The present invention relates also to the use of a compound of formula Ia or Ib as defined hereinbefore, in the manufacture of a medicament for the prevention and/or treatment of conditions associated with glycogen synthase kinase-3.

In the context of the present specification, the term "therapy" also includes "prevention" unless there are specific indications to the contrary. The terms "therapeutic" and "therapeutically" should be construed accordingly.

The invention also provides for a method of treatment and/or prevention of conditions associated with glycogen synthase kinase-3 comprising administering to a mammal, including man in need of such treatment and/or prevention a therapeutically effective amount of a compound of formula Ia or Ib, as hereinbefore defined.

Non-Medical Use

In addition to their use in therapeutic medicine, the compounds of formula Ia or Ib as a free base or a pharmaceutically acceptable salt thereof, are also useful as pharmacological tools in the development and standardisation of in vitro and in vivo test systems for the evaluation of the effects of inhibitors of GSK3 related activity in laboratory animals such as cats, dogs, rabbits, monkeys, rats and mice, as part of the search for new therapeutics agents.

Methods of Preparation

The present invention also relates to processes for preparing the compound of formula Ia or Ib. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in "Protective Groups in Organic Synthesis", T. W. Greene, P. G. M Wutz, Wiley-Interscience, New York, 1999.

Preparation of Intermediates

The process, wherein halo is halogen, $R^3$, $R^4$, $R^5$, $R^6$, $X^1$, n and m, unless otherwise specified, are as defined hereinbefore, comprises, (i) halogenation of a compound of formula II,

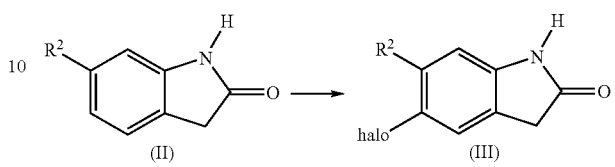

wherein $R^2$ is halogen, to obtain a compound of formula III, wherein halo is halogen e.g. bromine, chlorine or iodine, may be performed by an aromatic electrophilic substitution using a suitable halogenation agent such as $Br_2$, $Cl_2$, $I_2$, ICl, $SO_2Cl_2$ or another suitable halogenation agent such as N-bromosuccinimid in an appropriate solvent such as acetonitrile, acetic acid, HCl/ethanol or water, with or without a suitable base e.g. an alkali metal acetate such as sodium acetate, at a reaction temperature between $-20°$ C. and room temperature.

(ii) conversion of a compound of formula IV, wherein halo is a halogen, e.g. bromine or iodine, to obtain a compound of formula V, wherein $X^1$ is a direct bond and $R^6$ is as defined above,

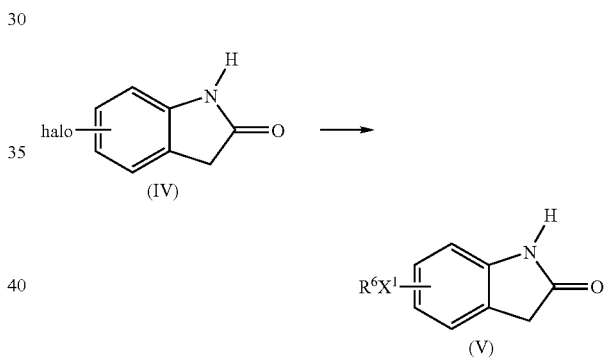

that may be carried out by reaction with a suitable tin reagent such as a trialkyltin-$R^6$ reagent e.g. tributyltin-$R^6$ in the presence of a suitable catalyst such as bis(triphenylphosphine) palladium(II) chloride, tetrakis(triphenylphosphine)palladium(0) or bis(triphenylphosphine)palladium(II) acetate in a suitable solvent such as tetrahydrofuran, acetonitrile, toluene or N,N-dimethylformamide and at a temperature range between 25° C. and reflux. The reaction may be aided by the presence of tetraethyl ammonium chloride.

(iii) reduction of a compound of formula VI to obtain a compound of formula VII,

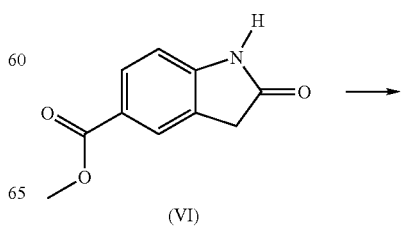

-continued

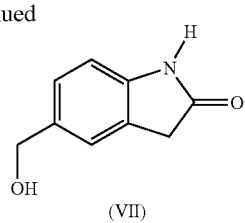
(VII)

that may be carried out in a suitable solvent such as toluene, tetrahydrofuran, diethyl ether or a mixture of tetrahydrofuran and an alcohol such as methanol or ethanol in the presence of a suitable reducing reagent such as lithium borohydride or sodium borohydride and at a reaction temperature between 0° C. and reflux.

(iv) oxidation of a compound of formula VII to obtain a compound of formula VIII,

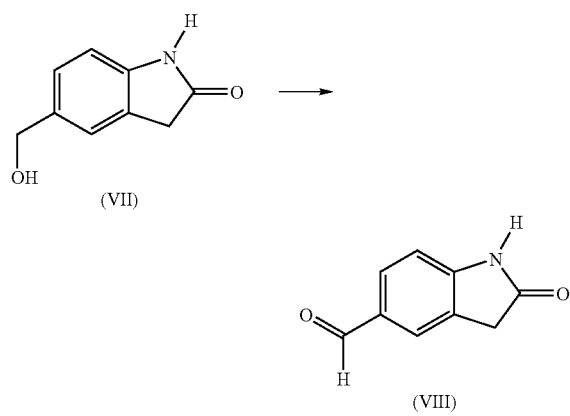

that may be carried out in a suitable solvent such as chloform, tetrahydrofuran or pyridine in the presence of a suitable oxidizing reagent such as chromium(VI) oxide or manganese (IV) oxide and at a reaction temperature between 0° C. and +100° C.

(v) conversion of a compound of formula VIII to obtain a compound of formula IX,

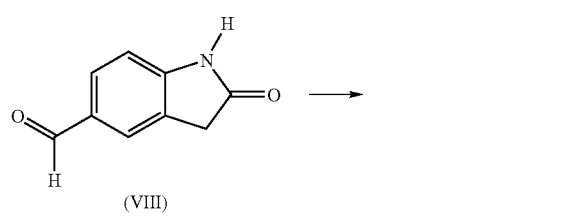

that may be carried out in a suitable solvent such as an alcohol e.g. methanol in the presence of a suitable reagent such as tosylmethyl isocyanide and a suitable base such as potassium carbonate or sodium carbonate and at a reaction temperature between 0° C. and reflux.

(vi) conversion of a compound of formula X to obtain a compound of formula XI,

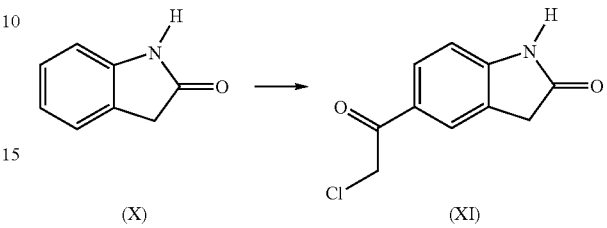

that may be carried out in a suitable solvent such as carbon disulfide in the presence of suitable reagents such as aluminum trichloride and chloroacetyl chloride and at a reaction temperature between 0° C. and reflux.

(vii) Conversion of a compound of formula XI to obtain a compound of formula XII,

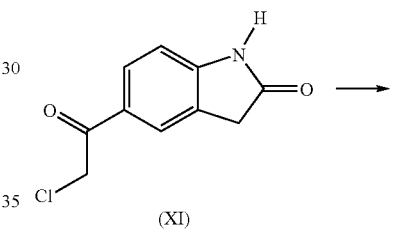

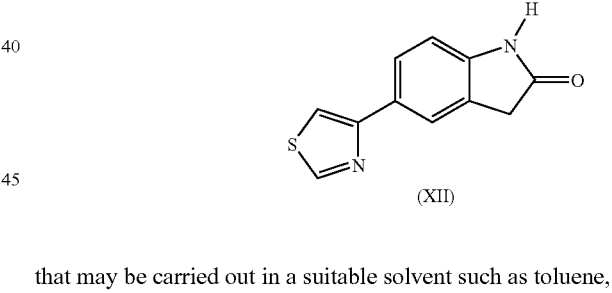

that may be carried out in a suitable solvent such as toluene, dioxane or tetrahydrofuran in the presence of a suitable reagent such as thioformamide and a suitable base such as a trialkylamine e.g triethylamine, or potassium carbonate and at a reaction temperature between +25° C. and reflux.

(viii) conversion of a compound of formula XI to obtain a compound of formula XIII,

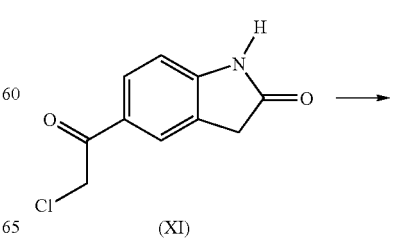

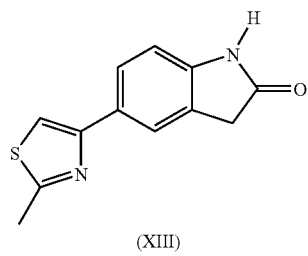

(XIII)

that may be carried out in a suitable solvent such as acetic acid in the presence of a suitable reagent such as thioacetamide and at a reaction temperature between +25° C. and reflux.

(ix) conversion of a compound of formula XIV, wherein halo is halogen e.g. fluorine, chlorine or bromine, to a compound of formula XV may be carried out by

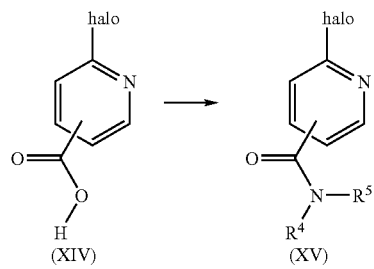

activation of the acid function in a compound of formula XIV, with a) a halogenation reagent such as thionyl chloride or oxalyl chlorid in a suitable solvent such as methylene chloride, chloroform or toluene or using the reagent neat and the reaction may occur at a temperature between 0° C. and +80° C., followed by the reaction with the appropriate amine R⁴R⁵NH in a suitable solvent such as methylene chloride, chloroform, toluene or acetonitrile with or without a suitable base such as an alkali metal, an alkaline earth metal carbonate or hydroxide such as sodium carbonate, potassium carbonate, calcium carbonate, sodium hydroxide or potassium hydroxide or an alkylamine base such as triethylamine and the reaction may occur at a temperature between −20° C. and +80° C., or b) a suitable coupling reagent such as 1,3-diisopropylcarbodiimide, 1-[3-(dimethylamino)propyl]-3-ethylcarbodiimide hydrochloride, 1,3-dicyclohexylcarbodiimide, O-(benzotriazol-1-yl)-N,N,N',N'-tetramethyluronium tetrafluoroborate, O-(benzotriazol-1-yl)-N,N,N',N'-tetramethyluronium hexafluorophosphate, 1,1'-carbonyldiimidazole or O-(7-azabenzotriazol-1-yl)-N,N,N',N'-tetramethyluronium hexafluorophosphate where the reaction may be aided by the addition of 1-hydroxybenzotriazole hydrate and in a suitable solvent such as methylene chloride, N,N-dimethylformamide or tetrahydrofuran and the reaction may occur at a temperature between +20° C. and +130° C., followed by addition of the appropriate amine R⁴R⁵NH and at a reaction temperature between +20° C. and +130° C.

(x) conversion of a compound of formula XVI, wherein halo is halogen e.g. fluorine, chlorine or bromine, to a compound of formula XV may be carried out by

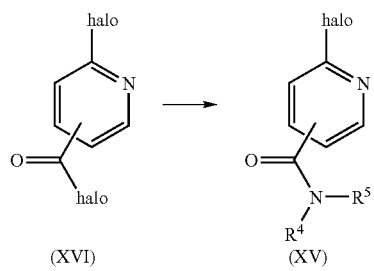

the reaction with the appropriate amine R⁴R⁵NH in a suitable solvent such as methylene chloride, chloroform, toluene or acetonitrile with or without a suitable base such as sodium carbonate, potassium carbonate, calcium carbonate, sodium hydroxide or potassium hydroxide or an alkylamine base such as triethylamine, the reaction may occur at a temperature between −20° C. and +80° C.

(xi) Conversion of a compound of formula XVII, wherein halo is halogen e.g. fluorine, chlorine or bromine, to a compound of formula XVIII may be carried out by

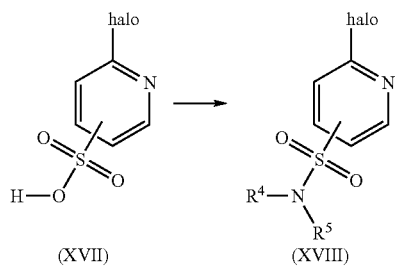

activation of the sulfonic acid function in the compound of formula XVII with a suitable halogenating reagent such as thionyl chloride or phosphorus oxychloride in a suitable solvent such as methylene chloride, chloroform, acetonitrile or toluene, and sulfolane may be added as a co-solvent to facilitate the reaction. A catalytic amount of N,N-dimethylacetamide may speed up the reaction and the reaction may occur at a temperature between 0° C. and +120° C., followed by the reaction with the appropriate substituted amine R⁴R⁵NH in a suitable solvent such as methylene chloride, chloroform, toluene or acetonitrile with or without a suitable base such as sodium carbonate, potassium carbonate, calcium carbonate, sodium hydroxide or potassium hydroxide or an alkylamine base such as triethylamine and the reaction may occur at a temperature between −20° C. and +80° C.

(xii) conversion of a compound of formula XIX, wherein halo is halogen e.g. fluorine, chlorine or bromine and $R^3$ is hydrogen or a halogen e.g. fluorine, chlorine or bromine, to a compound of formula XVIIIa may be carried out by

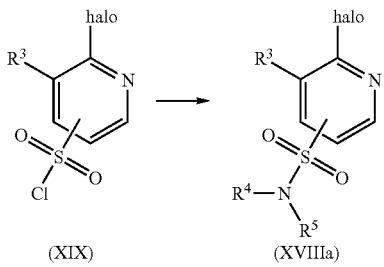

the reaction with the appropriate amine $R^4R^5NH$ in a suitable solvent such as methylene chloride, chloroform, toluene or acetonitrile with or without a suitable base such as sodium carbonate, potassium carbonate, calcium carbonate, sodium hydroxide or potassium hydroxide or an alkylamine base such as triethylamine and the reaction may occur at a temperature between −20° C. and +80° C.

(xiii) reaction of a compound of formula XX, wherein halo is halogen, to a compound of formula XXI may be carried out by

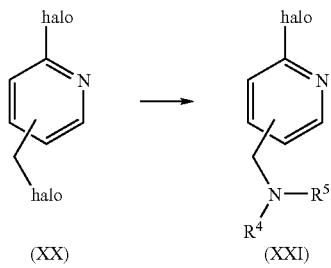

the reaction with an appropriate amine $R^4R^5NH$ in a suitable solvent such as methylene chloride, chloroform, acetonitrile or N,N-dimethylformamide with or without a suitable base such as sodium carbonate, potassium carbonate, calcium carbonate, sodium hydroxide or potassium hydroxide or an alkylamine base such as triethylamine and the reaction may occur at a temperature between 0° C. and +120° C.

(xiv) reaction of a compound of formula XXII, wherein halo is halogen e.g. fluorine chlorine, bromine, to a compound of formula XXIII may be carried out by

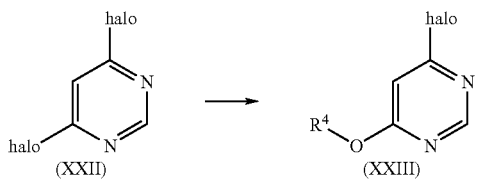

the reaction with an appropriate reagent $R^4OH$ in a suitable solvent such as acetonitrile, methylene chloride, chloroform, toluene or NDN-dimethylformamide in the presence of a suitable base such as sodium carbonate, potassium carbonate, calcium carbonate, sodium hydroxide, potassium hydroxide or sodium hydride or an alkylamine base such as triethylamine and the reaction may occur at a temperature between 0° C. and +80° C.

(xv) Conversion of a compound of formula XXIV, wherein halo is halogen e.g. fluorine, chlorine, bromine, to a compound of formula XXV may be carried out by

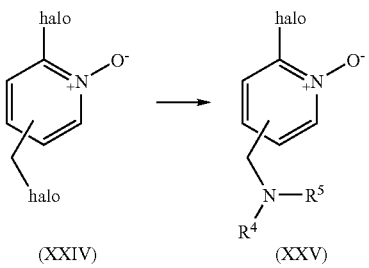

reacting a compound of formula XXIV with an appropriate amine $R^4R^5NH$ in a suitable solvent such as methylene chloride, chloroform, acetonitrile or N,N-dimethylformamide with or without a suitable base such as sodium carbonate, potassium carbonate, calcium carbonate, sodium hydroxide or potassium hydroxide or, an alkylamine base such as triethylamine or, a macroporous polystyrene anion-exchange resin such as MP-Carbonate or, a cross linked polystyrene-co-divinylbenzene such as PS-diisopropylethylamine and the is reaction may occur at a temperature between 0° C. and +120° C.

(xvi) reacting a compound of formula XXVI, wherein $R^4$ is $C_{1-6}$alkyl and halo is a halogen, e.g. fluorine, chlorine or bromine, with a compound of formula C (wherein $R^2$ and m are as defined above e.g. compounds of formula III, V, IX, XII or XIII) to form a compound of formula XXVII,

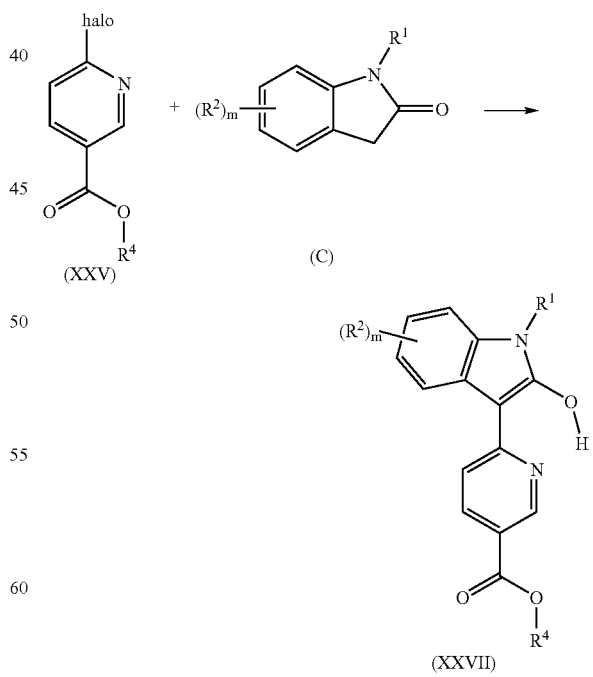

may be carried out in an appropriate solvent such as an ether e.g. tetrahydrofuran or 1,4-dioxan, an aromatic hydrocarbon solvent such as toluene or a dipolar aprotic solvent such as N,N-dimethylformamide, N,N-dimethylacetamide, N-methylpyrrolidin-2-one or dimethylsulphoxide and the reaction may occur at a temperature between +10° C. and +150° C.

The reaction is advantageously effected in the presence of a base. A suitable base may be an organic amine base such as pyridine, 2,6-lutidine, collidine, 4-dimethylaminopyridine, triethylamine, morpholine, N-methylmorpholine, diazabicyclo[5.4.0]undec-7-ene, tetramethylguanidine or an alkali metal or an alkaline earth metal carbonate or hydroxide such as sodium carbonate, potassium carbonate, calcium carbonate, sodium hydroxide or potassium hydroxide. Alternatively, such a base may be an alkali metal hydride such as sodium hydride, or an alkali metal or alkaline earth metal amide such as sodium amide, sodium bis(trimethylsilyl)amide, potassium amide or potassium bis(trimethylsilyl)amide.

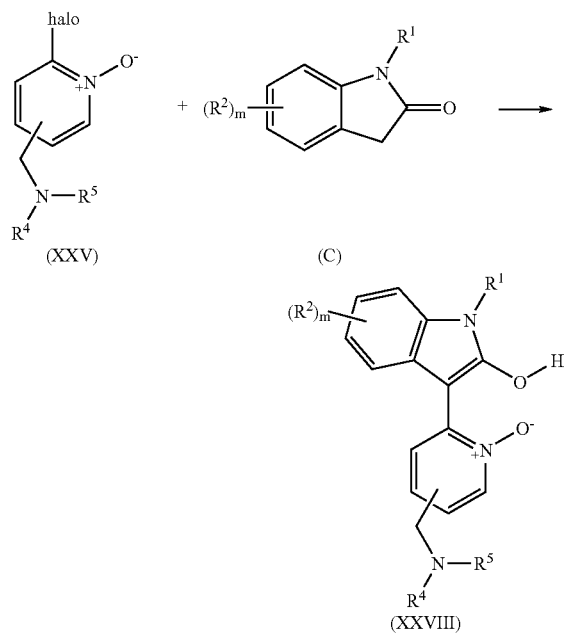

(xvii) reacting a compound of formula XXV, wherein halo is a halogen, e.g. fluorine, chlorine or bromine, with a compound of formula C (wherein $R^2$ and m are as defined above e.g. compounds of formula III, V, IX, XII or XIII), to form a compound of formula XXVIII, may be carried out in an appropriate solvent such as an ether e.g. tetrahydrofuran or 1,4-dioxan, an aromatic hydrocarbon solvent such as toluene or a dipolar aprotic solvent such as N,N-dimethylformrnamide, N,N-dimethylacetamide, N-methylpyrrolidin-2-one or dimethylsulphoxide and the reaction may occur at a temperature between +10° C. and +150° C.

The reaction is advantageously effected in the presence of a base. A suitable base may be an organic amine base such as pyridine, 2,6-lutidine, collidine, 4-dimethylaminopyridine, triethylamine, morpholine, N-methylmorpholine, diazabicyclo[5.4.0]undec-7-ene, tetramethylguanidine or an alkali metal or an alkaline earth metal carbonate or hydroxide such as sodium carbonate, potassium carbonate, calcium carbonate, sodium hydroxide or potassium hydroxide. Alternatively, such a base may be an alkali metal hydride such as sodium hydride, or an alkali metal or alkaline earth metal amide such as sodium amide, sodium bis(trimethylsilyl)amide, potassium amide or potassium bis(trimethylsilyl)amide.

Methods of Preparation of End Products

Another object of the invention are processes a, b, c, d and e for the preparation of compounds of general formula Ia and Ib, wherein halo is halogen, P, $R^1$, $R^2$, $R^3$, $R^4$, $R^5$, m and n, unless otherwise specified, are defined as hereinbefore, and salts thereof.

These processes comprise;

a) reacting a compound of formula B (XV, XVIII, XVIIIa, XXI, XXIII), wherein $L^1$ is a leaving group such as halogen, e.g. fluorine, chlorine or bromine, with a compound of formula C (e.g. compounds of formula III, V, IX, XII, XIII); wherein $R^1$, $R^2$ and m are as defined as hereinbefore to form a compound of formula Ia;

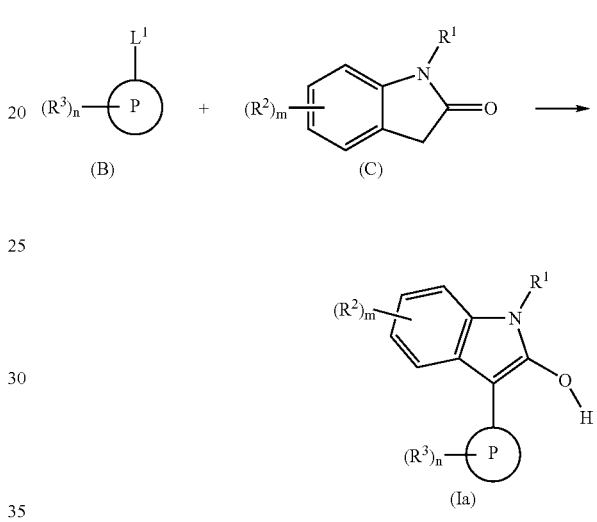

The reaction of process a may be carried out in an appropriate solvent such as an ether e.g. tetrahydrofuran or 1,4-dioxan, an aromatic hydrocarbon solvent such as toluene or a dipolar aprotic solvent such as N,N-dimethylformamide, N,N-dimethylacetamide, N-methylpyrrolidin-2-one or dimethylsulphoxide and the reaction may occur at a temperature between +10° C. and +150° C.

The reaction is advantageously effected in the presence of a base. A suitable base may be an organic amine base such as pyridine, 2,6-lutidine, collidine, 4-dimethylaminopyridine, triethylamine, morpholine, N-methylmorpholine, diazabicyclo[5.4.0]undec-7-ene, tetramethylguanidine or an alkali metal or an alkaline earth metal carbonate or hydroxide such as sodium carbonate, potassium carbonate, calcium carbonate, sodium hydroxide or potassium hydroxide. Alternatively, such a base may be an alkali metal hydride such as sodium hydride, or an alkali metal or alkaline earth metal amide such as sodium amide, sodium bis(trimethylsilyl)amide, potassium amide or potassium bis(trimethylsilyl)amide. When it is desired to obtain the acid salt, the free base may be treated with an acid such as a hydrogen halide such as hydrogen chloride or, a carboxylic acid such as fumaric acid in a suitable solvent such as tetrahydrofuran, diethyl ether, methanol, ethanol, chloroform or methylene chloride or mixtures thereof, the reaction may occur between –30° C. to +50° C.

b) reacting a compound of formula XXV, wherein halo is halogen, e.g. fluorine, chlorine or bromine, with a compound of formula C (e.g. compounds of formula III, V, IX, XII, XIII); wherein $R^1$, $R^2$ and m are as defined as hereinbefore); to form a compound of formula Ia;

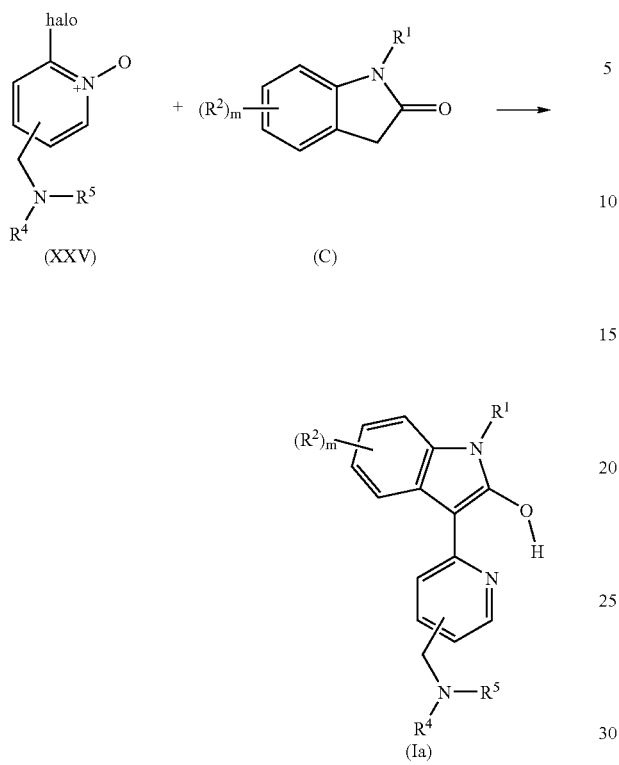

(XXV)    (C)    →

(Ia)

The reaction of process b may be carried out in an appropriate solvent such as an ether e.g. tetrahydrofuran or 1,4-dioxan, an aromatic hydrocarbon solvent such as toluene, or a dipolar aprotic solvent such as N,N-dimethylformamide, N,N-dimethylacetamide, N-methylpyrrolidin-2-one or dimethylsulphoxide, the reaction may occur at a temperature between +10° C. and +150° C.

The reaction is advantageously effected in the presence of a base. Such a base may be an organic amine base such as pyridine, 2,6-lutidine, collidine, 4-dimethylaminopyridine, triethylamine, morpholine, N-methylmorpholine, diazabicyclo[5.4.0]undec-7-ene, tetramethylguanidine or an alkali metal or an alkaline earth metal carbonate or hydroxide such as sodium carbonate, potassium carbonate, calcium carbonate, sodium hydroxide or potassium hydroxide. Alternatively, such a base may be an alkali metal hydride such as sodium hydride, an alkali metal or an alkaline earth metal amide such as sodium amide, sodium bis(trimethylsilyl)amide, potassium amide or potassium bis(trimethylsilyl)amide. The N-oxide may be removed by using a suitable reagent such as phosphorus trichloride in a suitable solvent such as methylene chloride, chloroform, toluene or ethyl acetate and the reaction may occur at a temperature between 0° C. and +100° C.

When it is desired to obtain the acid salt, the free base may be treated with an acid such as a hydrogen halide such as hydrogen chloride, or a carboxylic acid such as fumaric acid in a suitable solvent such as tetrahydrofuran, diethyl ether, methanol, ethanol, chloroform or methylene chloride or mixtures thereof, the reaction may occur between −30° C. to +50° C.

c) reacting a compound of formula XXVII, wherein $R^4$ is $C_{1-6}$alkyl, with the appropriate amine $HNR^4R^5$, to form a compound of formula Ia;

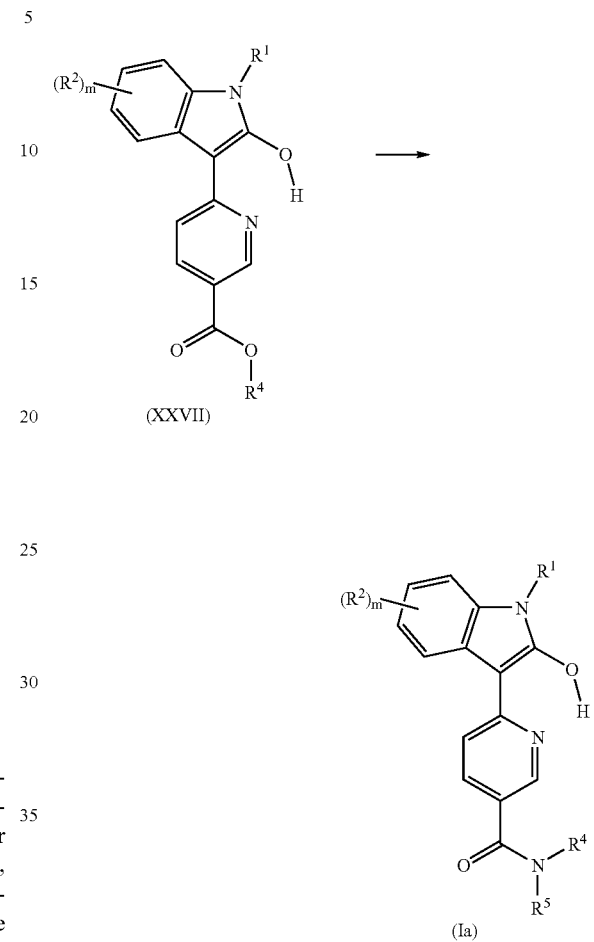

(XXVII)

(Ia)

The reaction of process c may be carried out by:

i) the reaction of the compound of formula XXVII with the appropriate amine $R^4R^5NH$ in a suitable solvent such as benzene, methylene chloride, chloroform, toluene or acetonitrile in the presence of a suitable reagent such as trimethyl aluminum and at a reaction temperature between 0° C. and reflux or, ii) the reaction of the compound of formula XXVII with the appropriate amine $R^4R^5NH$ neat or in a suitable solvent such as methylene chloride, chloroform, toluene or acetonitrile with or without a suitable base such as an alkali metal, an alkaline earth metal carbonate or is hydroxide such as sodium carbonate, potassium carbonate, calcium carbonate, sodium hydroxide or potassium hydroxide or an alkyl aminebase such as triethylamine, the reaction may occur at a temperature between −20° C. and +150° C.

When it is desired to obtain the acid salt, the free base may be treated with an acid such as a hydrogen halide such as hydrogen chloride, or a carboxylic acid such as fumaric acid in a suitable solvent such as tetrahydrofuran, diethyl ether, methanol, ethanol, chloroform or methylene chloride or mixtures thereof, the reaction may occur between −30° C. to +50° C.

d) reduction of the N-oxide in the compound of formula XXVIII to form a compound of formula Ia;

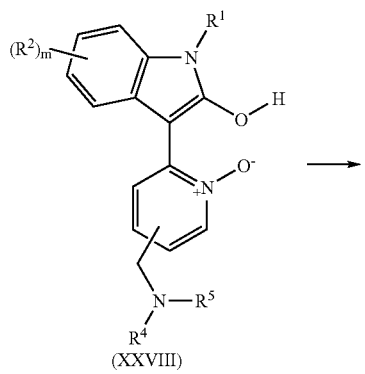
(XXVIII)

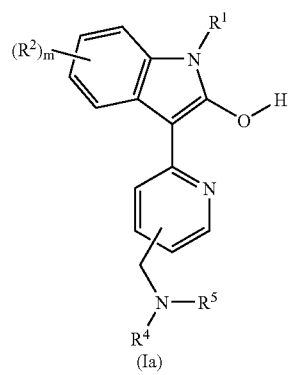
(Ia)

The N-oxide may be reduced by using a suitable reagent such as phosphorus trichloride in a suitable solvent such as methylene chloride, chloroform, toluene or ethyl acetate and the is reaction may occur at a temperature between 0° C. and +100° C.

When it is desired to obtain the acid salt, the free base may be treated with an acid such as a hydrogen halide such as hydrogen chloride, or a carboxylic acid such as fumaric acid in a suitable solvent such as tetrahydrofuran, diethyl ether, methanol, ethanol, chloroform or methylene chloride or mixtures thereof, the reaction may occur between −30° C. to +50° C.

e) fluorinating a compound of formula Ia to form a compound of formula Ib;

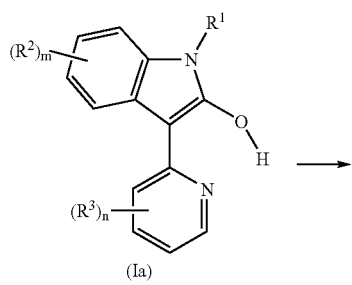
(Ia)

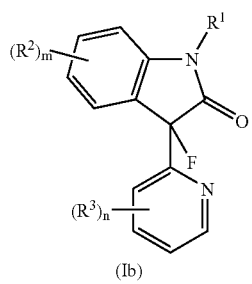
(Ib)

The reaction of process e may be carried out in an appropriate solvent such as an ether e.g. tetrahydrofuran or 1,4-dioxan or mixtures thereof in the presence of a suitable fluorinating reagent such as 1-fluoro-2,4,6-trimethylpyridinium triflate and a suitable base such as n-butyllithium or sodium bis(trimethylsilyl)amide and at a reaction temperature between −40° C. and +80° C.

When it is desired to obtain the acid salt, the free base may be treated with an acid such as a hydrogen halide such as hydrogen chloride, or a carboxylic acid such as fumaric acid in a suitable solvent such as tetrahydrofuran, diethyl ether, methanol, ethanol, chloroform or methylene chloride or mixtures thereof, the reaction may occur between −30° C. to +50° C.

Intermediates

The present invention further relates to new intermediates and the use of these intermediates in the preparation of compounds of formula Ia and Ib as defined hereinbefore.

In one aspect of the invention the intermediate is a compound according to formula XXV

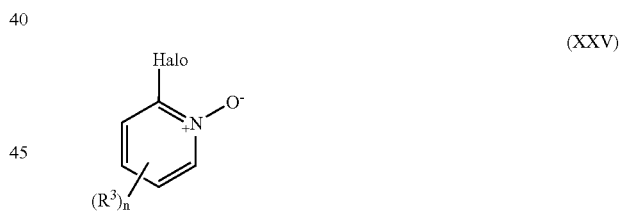
(XXV)

wherein halo is halogen; $R^3$ is selected from halogen, nitro, $C_{1-6}$alkyl, fluoromethyl, difluoromethyl, trifluoromethyl, fluoromethoxy, difluoromethoxy, trifluoromethoxy, $OC_{1-6}$alkylNR$^4$R$^5$, $C_{0-6}$alkylcyano, $C_{0-6}$alkylCONR$^4$R$^5$, $C_{0-6}$alkyl(SO$_2$)NR$^4$R$^5$, $C_{0-6}$alkylNR$^4$R$^5$ and a group $X^1R^6$, wherein $X^1$ is a direct bond, O, CONR$^7$R$^8$, SO$_2$NR$^9$R$^{10}$, SO$_2$R$^{11}$ or NR$^{12}$R$^{13}$; R$^7$, R$^9$ and R$^{12}$ each independently are hydrogen or $C_{1-3}$alkyl; R$^8$, R$^{10}$, R$^{11}$ and R$^{13}$ are $C_{0-4}$alkyl; R$^6$ is phenyl or a 5-, 6- or 7-membered heterocyclic group containing one or two heteroatoms, selected independently from N, O and S, which heterocyclic group may be saturated or unsaturated or said phenyl or 5-, 6- or 7-membered heterocyclic group may optionally be fused with a 5- or 6-membered saturated or unsaturated ring containing atoms selected independently from C, N, O and S and which phenyl or heterocyclic group may be substituted with one or two substituents selected from W; and $R^6$ is linked to $R^8$, $R^{10}$, $R^{11}$ and $R^{13}$.

In one embodiment of this aspect there are provided compounds according to formula XXV wherein $R^3$ is $C_{0-6}$alkylNR$^4$R$^5$; and n is 1.

In another aspect there are provided compounds, said compounds being:
1-[(6-Chloropyridin-3-yl)methyl]-4-methylpiperazine;
2-Chloro-5-(morpholin-4-ylmethyl)pyridine 1-oxide;
2-Chloro-5-(pyrrolidin-1-ylmethyl)pyridine 1-oxide;
1-[(6-Chloro-1-oxidopyridin-3-yl)methyl]-4-methyl-1,4-diazepane;
2-Chloro-5-[(4-pyrrolidin-1-ylpiperidin-1-yl)methyl]pyridine 1-oxide;
1-[(6-Chloro-1-oxidopyridin-3-yl)methyl]-N,N-dimethylpyrrolidin-3-amine;
2-Chloro-5-[(4-methylpiperidin-1-yl)methyl]pyridine 1-oxide;
1-[(6-Chloro-1-oxidopyridin-3-yl)methyl]-4-phenylpiperazine;
1-[(6-Chloro-1-oxidopyridin-3-yl)methyl]-4-[2-nitro-4-(trifluoromethyl)phenyl]piperazine;
3-[[(6-Chloro-1-oxidopyridin-3-yl)methyl](ethyl)amino]propanenitrile;
N-(4-Chlorobenzyl)-N-[(6-chloro-1-oxidopyridin-3-yl)methyl]-N-methylamine;
N-[(6-Chloro-1-oxidopyridin-3-yl)methyl]-N-(2-furylmethyl)-N-methylamine;
N-[(6-Chloro-1-oxidopyridin-3-yl)methyl]-N-methyl-N-phenylamine;
5-(Azetidin-1-ylmethyl)-2-chloropyridine 1-oxide;
2-Chloro-5-[(3-methylpiperidin-1-yl)methyl]pyridine 1-oxide;
N-[(6-Chloro-1-oxidopyridin-3-yl)methyl]-N-cyclohexyl-N-methylamine;
2-Chloro-5-(piperidin-1-ylmethyl)pyridine 1-oxide;
as a free base or a salt thereof.

In another aspect of the invention the intermediate is a compound according to formula B (XV, XVIII, XVIIIa XXI, XXIII)

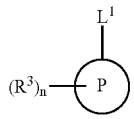

(B)

wherein P represents a 5- or 6-membered heteroaromatic ring containing one or two heteroatoms selected independently from N, O and S of which at least one atom is selected from nitrogen and $L^1$ is a leaving group such as a halogen e.g. fluorine, chlorine or bromine; wherein $R^3$ is selected from halogen, nitro, $C_{1-6}$alkyl, fluoromethyl, difluoromethyl, trifluoromethyl, fluoromethoxy, difluoromethoxy, trifluoromethoxy, $OC_{1-6}$alkylNR$^4$R$^5$, $C_{0-6}$alkylcyano, $C_{0-6}$alkylCONR$^4$R$^5$, $C_{0-6}$alkyl(SO$_2$)NR$^4$R$^5$, $C_{0-6}$NR$^4$R$^5$ and a group $X^1R^6$, wherein $X^1$ is a direct bond, O, CONR$^7$R$^8$, SO$_2$NR$^9$R$^{10}$, SO$_2$R$^{11}$ or NR$^{12}$R$^{13}$; $R^7$, $R^9$ and $R^{12}$ each independently are hydrogen or $C_{1-3}$alkyl; $R^8$, $R^{10}$, $R^{11}$ and $R^{13}$ are $C_{0-4}$alkyl; $R^6$ is phenyl or a 5-, 6- or 7-membered heterocyclic group containing one or two heteroatoms, selected independently from N, O and S, which heterocyclic group may be saturated or unsaturated or said phenyl or 5-, 6- or 7-membered heterocyclic group may optionally be fused with a 5- or 6-membered saturated or unsaturated ring containing atoms selected independently from C, N, O and S and which phenyl or heterocyclic group may be substituted with one or two substituents selected from W; and $R^6$ is linked to $R^8$, $R^{10}$, $R^{11}$ and $R^{13}$.

In one embodiment of this aspect there are provided compounds according to formula B (XV, XVIII, XVIIIa XXI, XXIII) wherein P is a pyridine or pyrimidine ring and $L^1$ is a leaving group such as a halogen e.g. chlorine; wherein $R^3$ is selected from $C_{0-6}$alkylCONR$^4$R$^5$, $C_{0-6}$alkyl(SO$_2$)NR$^4$R$^5$ and $C_{0-6}$alkylNR$^4$R$^5$; n is 1.

In another aspect there are provided compounds, said compounds being:
2-Chloro-N-[2-(dimethylamino)ethyl]isonicotinamide;
1-(2-Chloroisonicotinoyl)-4-methylpiperazine;
6-Chloro-N-[2-(dimethylamino)ethyl]-N-methylnicotinamide;
4-{2-[(6-Chloropyrimidin-4-yl)oxy]ethyl}morpholine;
1-Benzyl-4-[(6-chloropyridine-3-yl)sulfonyl]piperazine;
1-[(6-Chloropyridin-3-yl)sulfonyl]-4-(3-methylbutyl)piperazine;
1-[(6-Chloropyridin-3-yl)sulfonyl]-4-isopropylpiperazine;
1-[(6-Chloropyridin-3-yl)sulfonyl]-4-ethylpiperazine;
1-[(5-Bromo-6-chloropyridin-3-yl)sulfonyl]-4-methylpiperazine;
6-Chloro-N-methyl-N-(2-pyrrolidin-1-ylethyl)pyridine-3-sulfonamide;
6-Chloro-N-[2-(dimethylamino)ethyl]pyridine-3-sulfonamide;
6-Chloro-N-[2-(dimethylamino)ethyl]-N-ethylpyridine-3-sulfonamide;
6-Chloro-N-[(1-ethylpyrrolidin-2-yl)methyl]pyridine-3-sulfonamide;
1-[(6-Chloropyridin-3-yl)sulfonyl]-4-methyl-1,4-diazepane;
4-[(6-Chloropyridin-3-yl)sulfonyl]morpholine;
as a free base or a salt thereof.

In yet another aspect of the invention the intermediate is a compound according to formula C (III, V, IX, XII, XIII)

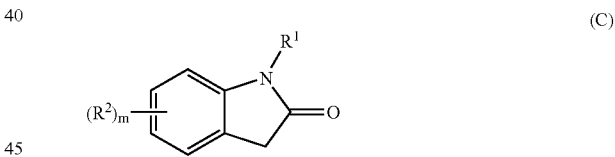

(C)

wherein $R^1$ is hydrogen; $R^2$ is selected from halogen, nitro, $C_{1-6}$alkyl, fluoromethyl, difluoromethyl, trifluoromethyl, fluoromethoxy, difluoromethoxy, trifluoromethoxy, $OC_{1-6}$alkylNR$^4$R$^5$, $C_{0-6}$alkylcyano, $C_{0-6}$alkylCONR$^4$R$^5$, $C_{0-6}$alkyl(SO$_2$)NR$^4$R$^5$, $C_{0-6}$alkylNR$^4$R$^5$ and a group $X^1R^6$, wherein $X^1$ is a direct bond, O, CONR$^7$R$^8$, SO$_2$NR$^9$R$^{10}$, SO$_2$R$^{11}$ or NR$^{12}$R$^{13}$; $R^7$, $R^9$ and $R^{12}$ each independently are hydrogen or $C_{1-3}$alkyl; $R^8$, $R^{10}$, $R^{11}$ and $R^{13}$ are $C_{0-4}$alkyl; $R^6$ is phenyl or a 5-, 6- or 7-membered heterocyclic group containing one or two heteroatoms, selected independently from N, O and S, which heterocyclic group may be saturated or unsaturated or said phenyl or 5-, 6- or 7-membered heterocyclic group may optionally be fused with a 5- or 6-membered saturated or unsaturated ring containing atoms selected independently from C, N, O and S and which phenyl or heterocyclic group may be substituted with one or two substituents selected from W; and $R^6$ is linked to $R^8$, $R^{10}$, $R^{11}$ and $R^{13}$.

In one embodiment of this aspect there are provided compounds according to formula C (III, V, IX, XII, XIII) wherein $R^1$ is hydrogen; $R^2$ is selected from halogen and a group $X^1R^6$, wherein $X^1$ is a direct bond; $R^6$ is a 5- or 6-membered heterocyclic group containing one or two heteroatoms, selected independently from N, O and S; m is 1 or 2.

In another aspect there are provided compounds, said compounds being:

5,6-Dibromo-1,3-dihydroindol-2-one;
5-Pyridin-3-yl-1,3-dihydro-2H-indol-2-one;
5-Thien-2-yl-1,3-dihydro-2H-indol-2-one;
5-(2-Furyl)-1,3-dihydro-2H-indol-2-one;
5-(1,3-Oxazol-5-yl)-1,3-dihydro-2H-indol-2-one;
5-(1,3-Thiazol-4-yl)-1,3-dihydro-2H-indol-2-one;
5-(2-Methyl-1,3-thiazol-4-yl)-1,3-dihydro-2H-indol-2-one;
as a free base or a salt thereof.

In yet another aspect of the invention the intermediate is a compound according to formula XXVII

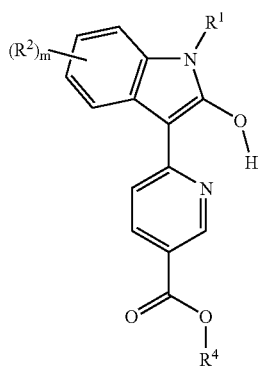

(XXVII)

wherein $R^1$ is hydrogen; $R^2$ is selected from halogen, nitro, $C_{1-6}$alkyl, fluoromethyl, difluoromethyl, trifluoromethyl, fluoromethoxy, difluoromethoxy, trifluoromethoxy, $OC_{1-6}$alkyl$NR^4R^5$, $C_{0-6}$alkylcyano, $C_{0-6}$alkylCONR$^4$R$^5$, $C_{0-6}$alkyl(SO$_2$)NR$^4$R$^5$, $C_{0-6}$alkylNR$^4$R$^5$ and a group $X^1R^6$, wherein $X^1$ is a direct bond, O, CONR$^7$R$^8$, SO$_2$NR$^9$R$^{10}$, SO$_2$R$^{11}$ or NR$^{12}$R$^{13}$; $R^7$, $R^9$ and $R^{12}$ each independently are hydrogen or $C_{1-3}$alkyl; $R^8$, $R^{10}$, $R^{11}$ and $R^{13}$ are $C_{0-4}$alkyl; $R^6$ is phenyl or a 5-, 6- or 7-membered heterocyclic group containing one or two heteroatoms, selected independently from N, O and S, which heterocyclic group may be saturated or unsaturated or said phenyl or 5-, 6- or 7-membered heterocyclic group may optionally be fused with a 5- or 6-membered saturated or unsaturated ring containing atoms selected independently from C, N, O and S and which phenyl or heterocyclic group may be substituted with one or two substituents selected from W; and $R^6$ is linked to $R^8$, $R^{10}$, $R^{11}$ and $R^{13}$.

In one embodiment of this aspect there are provided compounds according to formula Is XXVII, wherein $R^1$ is hydrogen; $R^2$ is selected from nitro and cyano; m is 1.

In another aspect there are provided compounds, said compounds being:

Ethyl 6-(2-hydroxy-5-nitro-1H-indol-3-yl)nicotinate;
Ethyl 6-(2-hydroxy-5-cyano-1H-indol-3-yl)nicotinate;

as a free base or a salt thereof.

In yet another aspect of the invention the intermediate is a compound according to formula XXVIII

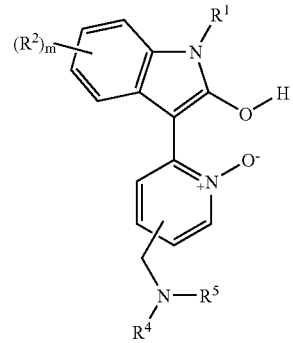

(XXVIII)

wherein $R^1$ is hydrogen; $R^2$ is selected from halogen, nitro, $C_{1-6}$alkyl, fluoromethyl, difluoromethyl, trifluoromethyl, fluoromethoxy, difluoromethoxy, trifluoromethoxy, $OC_{1-6}$alkylNR$^4$R$^5$, $C_{0-6}$alkylcyano, $C_{0-6}$alkylCONR$^4$R$^5$, $C_{0-6}$alkyl(SO$_2$)NR$^4$R$^5$, $C_{0-6}$alkylNR$^4$R$^5$ and a group $X^1R^6$, wherein $X^1$ is a direct bond, O, CONR$^7$R$^8$, SO$_2$NR$^9$R$^{10}$, SO$_2$R$^{11}$ or NR$^{12}$R$^{13}$; $R^7$, $R^9$ and $R^{12}$ each independently are hydrogen or $C_{1-3}$alkyl; $R^8$, $R^{10}$, $R^{11}$ and $R^{13}$ are $C_{0-4}$alkyl; $R^6$ is phenyl or a 5-, 6- or 7-membered heterocyclic group containing one or two heteroatoms, selected independently from N, O and S, which heterocyclic group may be saturated or unsaturated or said phenyl or 5-, 6- or 7-membered heterocyclic group may optionally be fused with a 5- or 6-membered saturated or unsaturated ring containing atoms selected independently from C, N, O and S and which phenyl or heterocyclic group may be substituted with one or two substituents selected from W; and $R^6$ is linked to $R^8$, $R^{10}$, $R^{11}$ and $R^{13}$.

In one embodiment of this aspect there are provided compounds according to formula XXVIII, wherein $R^1$ is hydrogen; $R^2$ is a group $X^1R^6$, wherein $X^1$ is a direct bond; $R^6$ is a 5- or 6-membered heterocyclic group containing one or two heteroatoms, selected independently from N, O and S; m is 1.

In yet another aspect there are provided compounds, said compounds being:

3-[5-(Morpholin-4-ylmethyl)-1-oxidopyridin-2-yl]-5-pyridin-3-yl-1H-indol-2-ol;
3-[5-(Morpholin-4-ylmethyl)-1-oxidopyridin-2-yl]-5-thien-2-yl-1H-indol-2-ol;
5-(2-Furyl)-3-[5-(morpholin-4-ylmethyl)-1-oxidopyridin-2-yl]-1H-indol-2-ol;

as a free base or a salt thereof.

In yet another aspect there are provided compounds, said compounds being:

5-(Hydroxymethyl)-1,3-dihydro-2H-indol-2-one;
2-Oxoindoline-5-carbaldehyde;
5-(Chloroacetyl)-1,3-dihydro-2H-indol-2-one;

as a free base or a salt thereof.

A further aspect of the invention relates to use of the compounds according to any one of formulas XXV; B (XV, XVIII, XVIIIa XXI, XXIII); C (III, V, IX, XII, XIII); XXVII; XXVIII; in the preparation of a compound of formula Ia or Ib.

WORKING EXAMPLES

The invention will now be illustrated in the following non-limiting Examples and unless stated otherwise:

(i) temperatures are given in degrees Celsius (° C.); operations were carried out at room temperature, i.e. at a temperature in the range of 18 to 25° C.;

(ii) yields are given for illustration only and are not necessarily those which can be obtained by diligent process development; preparations were repeated if more material was required;

(iii) when given, NMR data is in the form of delta values, given in parts per million (ppm) relative to the solvent or relative to tetramethylsilane (TMS) as an internal standard;

(iv) chemical symbols have their usual meanings; SI units and symbols are used;

(v) solvent ratios are given in volume:volume (v/v) terms; and (vi) mass spectra: where indicated, ionization was effected by chemical ionization (CI), electron impact (EI), fast atom bombardment (FAB) or electrospray (ESP) unless otherwise indicated; values for m/z are given; generally, only ions which indicate the parent mass are reported.

Example 1

2-Chloro-N-[2-(dimethylamino)ethyl]isonicotinamide

To a solution of 2-chloroisonicotinic acid (0.50 g, 3.17 mmol) in N,N-dimethylformamide (20 mL) was added 1,1'-carbonyldiimtidazole (0.565 g, 3.49 mmol). The solution was heated at 70° C. for 30 min. The reaction mixture was cooled to room temperature and N,N-dimethylethane-1,2-diamine (0.31 g, 3.49 mmol) was added. The solution was stirred at room temperature overnight. The solvent was evaporated in vacuo and the residue was purified on a silica gel column using chloroform/methanol/conc. $NH_3$(aq), (90:10:1), as the eluent to afford 40 mg (5,7% yield) of the title compound as a colorless oil: $^1$H NMR (CDCl$_3$, 400 MHz) 8.51 (d, J=5 Hz, 1 H), 7.68 (s, 1 H), 7.56 (dd, J=5, 1 Hz, 1 H), 6.92-7.08 (br s, 1 H), 3.58-3.48 (m, 2 H), 2.59-2.52 (m, 2 H), 2.28 (s, 6 H); MS (TSP) m/z 228 (M$^+$+1).

Example 2

1-(2-Chloroisonicotinoyl)-4-methylpiperazine

The title compound was prepared as described for Example 1 using 2-chloroisonicotinic acid and 1-methylpiperazine. The crude product was purified on a silica gel column using chloroform/methanolkconc. $NH_3$(aq), (100:10:1), as the eluent to give the title compound as a colorless oil. Yield: 68%: $^1$H NMR (CDCl$_3$, 400 MHz) δ 8.51 (d, J=5 Hz, 1 H), 7.57 (s, 1 H), 7.43 (dd, J=5, 1 Hz, 1 H), 3.66-3.58 (m, 2 H), 3.28-3.21 (m, 2 H), 2.41-2.34 (m, 2 H), 2.30-2.24 (m, 2 H), 2.20 (s, 3 H); MS (TSP) niz 240 (M$^+$+1).

Example 3

6-Chloro-N-[2-(dimethylamino)ethyl]-N-methylnicotinamide

To a solution of N,N,N-trimethylethylenediamine (1.0 g, 10 mmol) and triethylamine (2.0 g, 20 mmol) in methylene chloride (25 mL) was added 6-chloronicotinyl chloride (1.7 g, 10 mmol) in methylene chloride (50 mL) at room temperature. After 2 h at room temperature, the solvent was removed in vacuo and the residue was partitioned between a 2 M aqueous NaOH solution and methylene chloride. The combined extracts were dried (Na$_2$SO$_4$) and the solvent was removed in vacuo to afford 2.6 g of a crude product. The residue was purified on a silica gel column using acetonitrile/triethylamine, (90:10), as the eluent to afford 2.1 g (87% yield) of the title compound as an bright yellow oil: $^1$H NMR (DMSO-d6, 400 MHz) δ 8.62 (d, J=2 Hz, 1 H), 8.06 (dd, J=8, 2 Hz, 1 H), 7.76 (d, J=8 Hz, 1 H), 3.70 (s, 1 H), 3.41 (s, 1 H), 3.12 (d, J=19 Hz, 3 H), 2.64 (s, 1 H), 2.51 (s, 1 H), 2.37 (s, 3 H), 2.13 (s, 3 H); MS (TSP) m/z 242 (M$^+$+1).

Example 4

4-{2-[(6-Chloropyrimidin-4-yl)oxy]ethyl}morpholine

To a solution of N-(2-hydroxyethyl)morpholine (1.09 g, 8.27 mmol) in N,N-dimethylformamide (5 mL) was added sodium hydride (364 mg, 9.10 mmol, 60% dispersion in oil) in portions. The mixture was stirred at room temperature for 1 h and at 45° C. for 1.5 h. The greenish solution was added dropwise over 5 min to a solution of 4,6-dichloropyrimidine (3.0 g, 20.1 mmol) in N,N-dimethylformamide (5 mL). The solvent was removed in vacuo, and the residue was partitioned between water and ethyl acetate. The organic layer was dried (Na$_2$SO$_4$) and the solvent was removed in vacuo. The crude product was purified on a silica gel column using ethyl acetate as the eluent affording 1.17 g (58% yield) of the title compound as a yellow oil: $^1$H NMR (CDCl$_3$, 400 MHz) δ 8.57 (s, 1H), 6.80 (s, 1 H), 4.53 (t, J=6 Hz, 2 H), 3.72 (t, J=5 Hz, 4 H), 2.77 (t, J=6 Hz, 2 H), 2.55 (t, J=4 Hz, 4 H); $^{13}$C NMR (CDCl$_3$, 100 MHz) δ 170.0, 160.7, 158.1, 108.0, 66.9, 64.6, 57.1, 53.9; MS (ESP) m/z 244 (M$^+$+1).

Example 5

1-[(6-Chloropyridin-3-yl)methyl]-4-methylpiperazine

To a suspension of 2-chloro-5-(chloromethyl)pyridine (971 mg, 5.99 mmol) in acetonitrile (50 mL) was added a solution of N-methylpiperazine (1.20 g, 12.0 mmol) in acetonitrile (3 mL) followed by potassium carbonate (0.83 g, 5.99 mmol). The obtained yellow solution was heated at reflux for 40 min. The mixture was allowed to cool for 10 min and the solvent was removed in vacuo. The residue was partitioned between water, NaCl (s), and ethyl acetate. The aqueous layer was extracted with another portion of ethyl acetate. The combined organic layers were dried (Na$_2$SO$_4$) and the solvent was removed in vacuo affording 1.0 g (74% yield) of the title compound as a yellow oil: $^1$H NMR (CDCl$_3$, 400 MHz) δ 8.31 (d, J=2 Hz, 1 H), 7.65 (dd, J=8, 2 Hz, 1 H), 7.29 (d, J=8 Hz, 1 H), 3.49 (s, 2 H), 2.46 (br s, 8 H), 2.28 (s, 3 H); $^{13}$C NMR (CDCl$_3$, 100 MHz) δ 150.2, 150.1, 139.5, 132.8, 124.0, 59.2, 55.0, 53.0, 46.0; MS (ESP) m/z 226 (M$^+$+1).

Example 6

2-Chloro-5-(morpholin-4-ylmethyl)pyridine 1-oxide

A mixture of 2-chloro-5-(chloromethyl)pyridine 1-oxide (1.16 g, 6.52 mmol; described in: Tilley, J. W. et al, *J. Heterocyclic Chem.* 1979, 16, 333), morpholine (1.14 g, 13.0 mmol), and potassium carbonate (0.90 g, 6.52 mmol) in acetonitrile (30 mL) was stirred at room temperature for 72 h. The solvent was removed in vacuo and the residue was purified on a silica gel column using chloroform/ethanol, (9:1), as the eluent affording 1.21 g (81% yield) of the title compound as a colorless solid: mp 72-74° C.; $^1$H NMR (CDCl$_3$, 400 MHz) δ 8.34 (s, 1 H), 7.39 (d, J=8 Hz, 1 H), 7.16 (dd, J=8, 2 Hz, 1 H), 3.65 (t, J=5 Hz, 4 H), 3.40 (s, 2 H), 2.40 (t, J=4 Hz, 4 H); $^{13}$C NMR (CDCl$_3$, 100 MHz) δ 140.4 (br), 135.9, 126.6, 126.6, 66.8, 59.2, 53.4; MS (ESP) m/z 229 (M$^+$+1).

Example 7

6-Chloro-N-(2-pyrrolidin-1-ylethyl)pyridine-3-sulfonamide

The title compound was prepared as described for Example 3 using 2-pyrrolidin-1-yl-ethylamine and 6-chloropyridine-3-sulfonyl chloride (described in: Naegeli, C. et al. *Helv. Chim. Actal.* 1938, 21, 746-1750). Purification on a silica gel column using ethyl acetate/triethylamine, (9:1), as the eluent gave the title compound. Yield: 58%: $^1$H NMR (CDCl$_3$, 400 MHz) δ 8.79 (d, J=2Hz, 1 H), 8.05 (dd, J=8, 3Hz, 1 H), 7.42 (d, J=9 Hz, 1 H), 3.00 (app. t, J=6 Hz, 2 H), 2.50 (app. t, J=6 Hz, 2 H), 2.33 (m, 4 H), 1.67 (m, 4 H); $^{13}$C NMR (CDCl$_3$, 100 MHz) δ 155.7, 148.8, 137.8, 136.1, 125.0, 54.1, 53.9, 41.6, 23.9; MS (TSP) m/z 290 (M$^+$+1).

Example 8

2-Chloro-5-(pyrrolidin-1-ylmethyl)pyridine 1-oxide

To a solution of 2-chloro-5-(chloromethyl)pyridine 1-oxide (477 mg, 2.68 mmol; described in: Tilley, J. W. et al, *J. Heterocyclic Chem.* 1979, 16, 333) in acetonitrile (10 mL) was added pyrrolidine (381 mg, 5.36 mmol), and the reaction mixture was stirred at room temperature overnight. The solvent was evaporated, and the residue was dissolved in 2 M HCl(aq) and washed with ethyl acetate. The aqueous layer was alkalized to pH 8 with NaHCO$_3$ (s), and the mixture was extracted four times with ethyl acetate. The combined organic layers were dried (Na$_2$SO$_4$), and the solvent was evaporated to give 0.43 g (75% yield) of the title compound as a red oil: $^1$H NMR (CDCl$_3$, 400 MHz) δ 8.37 (d, J=1 Hz, 1 H), 7.44 (d, J=8 Hz, 1 H), 7.23 (dd, J=8, 2 Hz, 1 H), 3.57 (s, 2 H), 2.51 (m, 4 H), 1.80 (m, 4 H); $^{13}$C NMR (CDCl$_3$, 100 MHz) δ 140.1, 139.9, 137.2, 126.4, 126.4, 56.4, 54.0, 23.5; MS (ES) m/z 213 (M$^+$+1).

Example 9

1-[(6-Chloro-1-oxidopyridin-3-yl)methyl]-4-methyl-1,4-diazepane

To a solution of 2-chloro-5-(chloromethyl)pyridine 1-oxide (940 mg, 5.28 mmol; described in: Tilley, J. W. et al, *J. Heterocyclic Chem.* 1979, 16, 333) in acetonitrile (30 mL) were added N-methylhomopiperazine (1.21 g, 10.6 mmol), and K$_2$CO$_3$ (730 mg, 5.28 mmol). The reaction mixture was stirred at room temperature for 3.5 days. The solvent was removed in vacuo, and the residue was partitioned between brine and ethyl acetate. The aqueous layer was extracted with another two portions of ethyl acetate and one portion of tetrahydrofuran. The combined organic layers were dried (Na$_2$SO$_4$), and evaporated to give 0.86 g (64% yield) of the title compound as an orange oil: $^1$H NMR (aceton-d6, 400 MHz) δ 8.30 (dd, J=2 Hz, 1 H), 7.60 (d, J=8 Hz, 1 H), 7.29 (dd, J=8, 2 Hz, 1 H), 3.65 (s, 2 H), 2.74-2.69 (m, 4 H), 2.62-2.54 (m, 4 H), 2.29 (s, 3 H), 1.81-1.75 (m, 2 H); MS (ES) m/z 256 (M$^+$+1).

The following Examples, 10-11, were prepared as described for Example 9:

Example 10

2-Chloro-5-[(4-pyrrolidin-1-ylpiperidin-1-yl)methyl]pyridine 1-oxide

Starting material: 4-(1-pyrrolidinyl)piperidine. Yield: 93%: $^1$H NMR (CDCl$_3$, 400 MHz) δ 8.33 (d, J=1 Hz, 1 H), 7.41 (d, J=8 Hz, 1 H), 7.21 (dd, J=8, 2 Hz, 1 H), 3.41 (s, 2 H), 2.83-2.78 (m, 2 H), 2.58-2.53 (m, 4 H), 2.15-2.00 (m, 3 H), 1.88-1.83 (m, 2 H), 1.81-1.75 (m, 4 H), 1.61-1.53 (m, 2 H); MS (ES) m/z 296 (M$^+$+1).

Example 11

1-[(6-Chloro-1-oxidopyridin-3-yl)methyl]-N,N-dimethylpyrrolidin-3-amine

Starting material: 3-(dimethylamino)pyrrolidine. Yield: 67%: $^1$H NMR (aceton-d6, 400 MHz) δ 8.28 (d, J=1 Hz, 1 H), 7.60 (d, J=8 Hz, 1 H), 7.27 (dd, J=8, 2 Hz, 1 H), 3.66-3.53 (m, 2 H), 2.76-2.63 (m, 2 H), 2.58-2.50 (m, 1 H), 2.43-2.35 (m, 1 H), 2.24-2.21 (m, 1 H), 2.12 (s, 6 H), 1.96-1.89 (m, 1 H), 1.74-1.64 (m, 1 H); MS (ES) m/z 256 (M$^+$+1).

Example 12

2-Chloro-5-[(4-methylpiperidin-1-yl)methyl]pyridine 1-oxide

To a solution of 2-chloro-5-(chloromethyl)pyridine 1-oxide (222 mg, 1.25 mmol; described in: Tilley, J. W. et al, *J. Heterocyclic Chem.* 1979, 16, 333) in tetrahydrofuran (2 mL) were added a solution of 4-methylpiperidine (247 mg, 2.49 mmol) in tetrahydrofuran (1.5 mL), a catalytic amount of potassium iodide, and MP-Carbonate (2.55 mmol/g, 1.47 g, 3.74 mmol). The mixture was gently stirred at room temperature for one week. The mixture was filtered (20 μm polyethylene filter), and the beads were washed with several portions of methylene chloride. The filtrate was washed with NaHCO$_3$ (aq. sat.), dried (Na$_2$SO$_4$), and the solvent was evaporated to give a crude product which was purified by column chromatography using chloroform/ethanol, (95:5), as the eluent to give 168 mg (56% yield) of the title compound as a yellow oil: $^1$H NMR (CDCl$_3$, 400 MHz) δ 8.37 (d, J=1 Hz, 1 H), 7.41 (d, J=8 Hz, 1 H), 7.20 (dd, J=8, 2 Hz, 1 H), 3.41 (s, 2 H), 2.80-2.75 (m, 2 H), 2.00 (dt, J=12, 2 Hz, 2 H), 1.63-1.58 (m, 2 H), 1.45-1.30 (m, 1 H), 1.22 (m, 2 H), 0.92 (d, J=6 Hz, 3 H); MS (ES) m/z 241 (M$^+$+1).

Example 13

1-[(6-Chloro-1-oxidopyridin-3-yl)methyl]-4-phenylpiperazine

PS-Diisopropylethylamine (3.54 mmol/g, 0.4 g, 1.40 mmol) was washed with tetrahydrofuran and 2-chloro-5-(chloromethyl)pyridine 1-oxide (100 mg, 0.56 mmol; described in: Tilley, J. W. et al, *J. Heterocyclic Chem.* 1979, 16, 333) was added followed by tetrahydrofuran (1 mL). A solution of 1-phenylpiperazine (182 mg, 1.12 mmol) in tetrahydrofuran (1 mL) and a catalytic amount of potassium iodide were added, and the mixture was gently stirred (100 r/min) at room temperature for one week. PS-Isocyanate (1.76 mmol/g, 0.80 g, 1.40 mmol) was washed with tetrahydrofuran and added to the mixture followed by additional tetrahydrofuran (1 mL). The suspension was gently stirred (100 r/min) at room temperature for 19 h. The suspension was filtered (20 μm polyethylene filter), and the resins were washed with methylene chloride, tetrahydrofuran, and ethanol. Volatiles were removed in vacuo, and the residue was suspended in a 1:1-mixture of tetrahydrofuran and ethanol (8 mL) followed by the addition of N-ethyl-N,N-diisopropylamine (50 μL, 0.28 mmol). The mixture was added to PS-Thiophenol (1.35 mmol/g, 0.21 g, 0.28 mmol), and MP-Carbonate (3.20 mmol/g, 90 mg, 0.28 mmol), both pre-swelled in tetrahydrofuran. The mixture was stirred (100 r/min) at room temperature overnight followed by filtration. The resins were washed with methylene chloride, tetrahydrofuran, and ethanol, and the filtrate was concentrated in vacuo to give 141 mg (83% yield) of the title compound: $^1$H NMR (CDCl$_3$, 400 MHz) δ 8.42 (s, 1 H), 7.45 (d, J=8 Hz, 1 H), 7.30-7.26 (m, 2 H), 7.25-7.21 (m, 1 H), 6.95-6.90 (m, 2 H), 6.89-6.85 (m, 1 H), 3.51 (s, 2 H), 3.22-3.18 (m, 4 H), 2.65-2.60 (m, 4 H); MS (ES) m/z 304 (M$^+$+1).

The following Examples, 14-19, were prepared as described for Example 13:

Example 14

1-[(6-Chloro-1-oxidopyridin-3-yl)methyl]-4-[2-nitro-4-(trifluoromethyl)phenyl]piperazine Starting material: 1-[2-nitro-4-(trifluoromethyl)phenyl]piperazine. Yield: 100%: $^1$H NMR (CDCl$_3$, 400 MHz) δ 8.43 (d, J=1 Hz, 1 H), 8.06 (d, J=2 Hz, 1 H), 7.68 (dd, J=9, 2 Hz, 1 H), 7.45 (d, J=8 Hz, 1 H), 7.19 (dd, J=8, 2Hz, 1 H), 7.16 (d, J=9 Hz, 1 H), 3.54 (s, 2 H), 3.18 (t, J=5 Hz, 4 H), 2.64 (t, J=5 Hz, 4 H); MS (ES) m/z 417 (M$^+$+1).

Example 15

3-[[(6-Chloro-1-oxidopyridin-3-yl)methyl](ethyl)amino]propanenitrile

Starting material: 3-(ethylamino)propionitrile. Yield: 82%: $^1$H NMR (CDCl$_3$, 400 MHz) δ 8.35 (d, J=Hz, 1 H), 7.46 (d, J=8 Hz, 1 H), 7.32 (dd, J=9, 1 Hz, 1 H), 3.60 (s, 2 H), 2.82 (t, J=7 Hz, 2 H), 2.60 (q, J=7 Hz, 2 H), 2.47 (t, J=7 Hz, 2 H), 1.07 (t, J=7 Hz, 3 H); MS (ES) m/z 240 (M$^+$+1).

Example 16

N-(4-Chlorobenzyl)-N-[(6-chloro-1-oxidopyridin-3-yl)methyl]-N-methylamine

Starting material: p-chloro-N-methylbenzylamine. Yield: 100%: $^1$H NMR (CDCl$_3$/DMSO-d6, 7:1, 400 MHz) δ 8.39 (s, 1 H), 7.46 (dd, J=8, 1 Hz, 1 H), 7.34-7.26 (m, 4 H), 7.24-7.20 (m, 1 H), 3.54 (d, J=2 Hz, 2 H), 3.45 (s, 2 H), 2.20 (d, J=2 Hz, 3 H); MS m/z 297 (M$^+$+1).

Example 17

N-[(6-Chloro-1-oxidopyridin-3-yl)methyl]-N-(2-furylmethyl)-N-methylamine

Starting material: N-methylfurfurylamine. Yield: 71%: $^1$H NMR (CDCl$_3$, 400 MHz) δ 8.37 (d, J=1 Hz, 1 H), 7.43 (d, J=8 Hz, 1 H), 7.39 (dd, J=2, 1 Hz, 1 H), 7.22 (dd, J=8, 2 Hz, 1 H), 6.34 (dd, J=3, 2 Hz, 1 H), 6.22-6.20 (m, 1 H), 3.61 (s, 2 H), 3.46 (s, 2 H), 2.26 (s, 3 H); MS (ES) m/z 253 (M$^+$+1).

Example 18

N-[(6-Chloro-1-oxidopyridin-3-yl)methyl]-N-methyl-N-phenylamine

Starting material: N-methylaniline. Yield: 100%: $^1$H NMR (CDCl$_3$, 400 MHz) δ 8.26 (d, J=1 Hz, 1 H), 7.42 (d, J=8 Hz, 1 H), 7.26-7.20 (m, 2 H), 7.10-7.06 (m, 1 H), 6.81-6.75 (m, 1 H), 6.71-6.67 (m, 2 H), 4.45 (s, 2 H), 3.02 (s, 3 H); MS (ES) m/z 249 (M$^+$+1).

Example 19

5-(Azetidin-1-ylmethyl)-2-chloropyridine 1-oxide

Starting material: azetidine. Yield: 100%: MS (ES) m/z 199 (M$^+$+1).

Example 20

2-Chloro-5-[(3-methylpiperidin-1-yl)methyl]pyridine 1-oxide

PS-Diisopropylethylamine (3.54 mmol/g, 0.4 g, 1.40 mmol) was washed with tetrahydrofuran and 2-chloro-5-(chloromethyl)pyridine 1-oxide (100 mg, 0.56 mmol; described in: Tilley, J. W. et al, *J. Heterocyclic Chem*. 1979, 16, 333) was added followed by tetrahydrofuran (1 mL). A solution of 3-methylpiperidine in tetrahydrofuran (1.5 mL) and a catalytic amount of potassium iodide were added, and the mixture was gently stirred (80 r/min) at room temperature for 5 days. PS-Isocyanate (1.10 mmol/g, 1.27 g, 1.40 mmol) was washed with tetrahydrofuran and added to the mixture followed by additional tetrahydrofuran (2 mL). The suspension was gently stirred (80 r/min) at room temperature overnight. N-Ethyl-N,N-diisopropylamine (50 μL, 0.28 mmol) and MP-Carbonate (2.55 mmol/g, 0.66 g, 1.68 mmol) were added, and the containts were mixed and gently stirred for 24 h. The mixture was filtered (20 μm polyethylene filter), and the resins were washed with methylene chloride. Volatiles were removed in vacuo to give 138 mg (99% yield) of the title compound: MS (ES) m/z 241 (M$^+$+1).

The following Examples, 21-22, were prepared as described for Example 20:

Example 21

N-[(6-Chloro-1-oxidopyridin-3-yl)methyl]-N-cyclohexyl-N-methylamine

Starting material: N-methylcyclohexylamine. Yield: 96%: MS (ES) nvz 255 (M$^+$+1).

Example 22

2-Chloro-5-(piperidin-1-ylmethyl)pyridine 1-oxide

Starting material: piperidine: MS (ES) m/z 227 (M$^+$+1).

Example 23

5,6-Dibromo-1,3-dihydroindol-2-one

6-Bromooxindole (0.168 g, 0.8 mmol) was dissolved in acetic acid (4 mL) and stirred for 5 min at room temperature. N-Bromosuccinimide (0.14 g, 0.8 mmol) was added and the yellow reaction mixture was stirred for 3 h at ambient temperature. The mixture was poured onto ice and the resulting precipitate was collected by filtration and dried in vacuo to give 0.192 g (83% yield) of the title compound as a white solid: $^1$H NMR (DMSO-d6, 400 MHz) δ 10.61 (s, 1 H), 7.60 (s, 1 H), 7.14 (s, 1 H), 3.52 (s, 2 H).

Example 24

1-Benzyl-4-[(6-chloropyridine-3-yl)sulfonyl]piperazine

To a solution of benzylpiperazine (0.45 mL, 2.59 mmol) in methylene chloride (15 mL), cooled on an ice-bath, was 6-chloropyridine-3-sulfonyl chloride (0.50 g, 2.36 mmol; described in: Naegeli, C. et al. *Helv. Chim. Actal.* 1938, 21, 1746-1750) dissolved in methylene chloride (10 mL) added slowly. The reaction was stirred for 30 min and the formed white precipitation was filtered and washed with methylene chloride and water affording, after drying, 0.68 g (82% yield) of the title compound: $^1$H NMR (DMSO-d6, 400 MHz) δ 8.70 (d, J=3 Hz, 1 H), 8.14 (dd, J=8, 3 Hz, 1 H), 7.76 (d, J=8 Hz, 1 H), 7.50-7.43 (m, 2 H), 7.38-7.30 (m, 3 H), 4.23 (br s, 2 H), 3.79-3.63 (m, 2 H), 3.45-3.18 (m, 2 H), 3.11-2.96 (m, 2 H), 2.96-2.81 (m, 2 H); MS (ES) m/z 352 (M$^+$+1).

Example 25

1-[(6-Chloropyridin-3-yl)sulfonyl]-4-(3-methylbutyl) piperazine

To a solution of 1-(3-methylbutyl)piperazine (0.41 g, 2.60 mmol; described in: Yamane, T. et al. *Chem. Pharm. Bull.* 1993, 41, 148-155) in methylene chloride (15 mL) cooled on an ice-bath was 6-chloropyridine-3-sulfonyl chloride (0.50 g, 2.36 mmol; described in: Naegeli, C. et al. *Helv. Chim. Actal.* 1938, 21, 1746-1750) dissolved in methylene chloride (10 mL) added slowly. The reaction was stirred for 30 min and a 5% HCl(aq) solution (30 mL) was added and the phases were separated. The aqueous layer was alkalyzed with a saturated aqueous NaHCO$_3$ solution until pH 9 and the mixture was extracted with methylene chloride. The organic layers were combined, dried (Na$_2$SO$_4$) and the solvent was removed in vacuo affording 650 mg (83% yield) of the title compound as a white solid: $^1$H NM (CDCl$_3$, 400 MHz) δ 8.75 (d, J=2 Hz, 1 H), 7.97 (dd, J=8, 2 Hz, 1 H), 7.51 (d, J=8 Hz, 1 H), 3.33-3.05 (m, 4 H), 2.86-2.29 (m, 6 H), 1.66-1.50 (m, 1 H), 1.5-1.28 (m, 2 H), 0.88 (d, J=7 Hz, 6 H); MS (ES) mz 332 (M$^+$+1).

Example 26

1-[(6-Chloropyridin-3-yl)sulfonyl]-4-isopropylpiperazine

The title compound was prepared as described for Example 25 using N-isopropylpiperazine and 6-chloropyridine-3-sulfonyl chloride (described in: Naegeli, C. et al. *Helv. Chim. Actal.* 1938, 21, 1746-1750). Yield: 89%: $^1$H NMR (CDCl$_3$, 400 MHz) δ 8.73 (d, J=3 Hz, 1 H), 7.96 (dd, J=8, 3 Hz, 1 H), 7.48 (d, J=8 Hz, 1 H), 3.12-3.01 (m, 4 H), 2.76-2.63 (m, 1 H), 2.63-2.54 (m, 4 H), 0.99 (d, J=7 Hz, 6 H); $^{13}$C NMR (CDCl$_3$, 100 MHz) δ 156.1, 149.3, 138.2, 131.7, 125.0, 54.8, 48.0, 46.7, 18.7; MS (ES) m/z 304 (M$^+$+1).

Example 27

1-[(6-Chloropyridin-3-yl)sulfonyl]-4-ethylpiperazine

The title compound was prepared as described for Example 25 using N-ethylpiperazine and 6-chloropyridine-3-sulfonyl chloride (described in: Naegeli, C. et al. *Helv. Chim. Actal.* 1938, 21, 1746-1750). Yield:83%: $^1$H NMR (CDCl$_3$, 400 MHz) δ 8.75 (d, J=3 Hz, 1 H), 7.97 (dd, J=8, 3 Hz, 1 H), 7.50 (d, J=8 Hz, 1 H), 3.16-3.06 (m, 4 H), 2.60-2.46 (m, 4 H), 2.42 (q, J=7 Hz, 2 H), 1.04 (t, J=7 Hz, 3 H); $^{13}$C NMR (CDCl$_3$, 100 MHz) δ 155.8, 148.9, 137.8, 131.3, 124.7, 51.9, 51.6, 46.0, 11.9; MS (ES) m/z 290 (M$^+$+1).

Example 28

1-[(5-Bromo-6-chloropyridin-3-yl)sulfonyl]-4-methylpiperazine

The title compound was prepared as described for Example 3 using 1-methylpiperazine and 5-bromo-6-chloropyridine-3-sulfonyl chloride. Yield: 91%: $^1$H NMR (CDCl$_3$, 400 MHz) δ 8.59 (d, J=2 Hz, 1 H), 7.67 (d, J=2 Hz, 1 H), 3.08-3.01 (m, 4 H), 2.43 (t, J=5 Hz, 4 H), 2.22 (s, 3 H); $^{13}$C NMR (CDCl$_3$, 100 MHz) δ 155.5, 146.8, 141.2, 132.7, 121.4, 54.2, 46.3, 46.1.

Example 29

6-Chloro-N-methyl-N-(2-pyrrolidin-1-ylethyl)pyridine-3-sulfonamide

To a solution of 6-chloropyridine-3-sulfonylchloride (636 mg, 3 mmol; described in: Naegeli, C. et al. *Helv. Chim. Actal.* 1938, 21, 1746-1750) in methylene chloride (10 mL) was added methyl-(2-pyrrolidin-1-ylethyl)amine (384 mg, 3 mmol; described in: *J. Amer. Chem. Soc.* 1955, 77, 3632-3634) dissolved in methylene chloride (10 mL) dropwise. The reaction mixture was stirred over night at room temperature followed by the extraction with aqueous HCl (3%). The acidic water layer was alkalized with an aqueous saturated solution of NaHCO$_3$ and extracted with methylene chloride. The organic phase was dried (Na$_2$SO$_4$) and evaporated in vacuo to give 0.75 gram (80% yield) of the title compound: MS (ES) m/z 304 (M$^+$+1).

Example 30

6-Chloro-N-[2-(dimethylamino)ethyl]pyridine-3-sulfonamide

The title compound was prepared as described for Example 29 using 6-chloropyridine-3-sulfonylchloride and N,N-dimethylethane-1,2-diamine. Yield: 72%: MS (MS) m/z 264 (M$^+$+1).

Example 31

6-Chloro-N-[2-(dimethylamino)ethyl]-N-ethylpyridine-3-sulfonamide

To a solution of N'-ethyl-N,N-dimethylethane-1,2-diamine (0.62 mL, 4.4 mmol) in methylene chloride (10 mL) was added 6-chloropyridine-3-sulfonylchloride (0.85 g, 4 mmol; described in: Naegeli, C. et al. *Helv. Chim. Actal.* 1938, 21, 1746-1750) dissolved in methylene chloride (10 mL) dropwise. The reaction mixture was stirred for 30 min at room temperature followed by the extraction with aqueous HCl (5%). The acidic water layer was alkalized with an aqueous saturated solution of NaHCO$_3$ and extracted with methylene chloride. The organic phase was dried (Na$_2$SO$_4$) and evaporated in vacuo to give 0.7 gram (60% yield) of the title compound: MS (ES) m/z 292 (M$^+$+1).

Example 32

6-Chloro-N-[(1-ethylpyrrolidin-2-yl)methyl]pyridine-3-sulfonamide

The title compound was prepared as described for Example 31 using (1-ethylpyrrolidin-2-yl)methylamine. Yield: 58%: MS (ES) m/z 304 (M$^+$+1).

Example 33

1-[(6-Chloropyridin-3-yl)sulfonyl]-4-methyl-1,4-diazepane

The title compound was prepared as described for Example 31 using 1-methylhomopiperazine. Yield: 60%: MS (ES) m/z 290 (M$^+$+1).

Example 34

4-[(6-Chloropyridin-3-yl)sulfonyl]morpholine

The title compound was prepared as described for Example 31 using morpholine. The crude product was purified on a silica gel column using heptane/ethyl acetate, (1:1), as the eluent: Yield: 60%: MS (ES) m/z 263 (M$^+$+1).

Example 35

Ethyl 6-(2-hydroxy-5-nitro-1H-indol-3-yl)nicotinate

To a cooled solution of 5-nitrooxindol (5.27 g, 29.6 mmol) in N,N-dimethylamide (50 mL) was added sodium hydride (1.4 g, 35 mmol) during 5 min at 0° C. After 10 min at 0° C., 6-chloronicotinic acid ethyl ester (5.0 g, 26.9 mmol) was added dropwise and the reaction was heated to 135° C. for 45 min. The mixture was diluted with water (200 mL) and saturated NH$_4$Cl(aq) (100 mL). The formed precipitate was filtrated and washed with water, methanol, ethyl acetate and diethyl ether. The residual green yellow solid was dried to give 4.1 g (47% yield) of the title compound: $^1$H NMR (DMSO-d6, 300 MHz) δ 14.57 (s, 1 H), 11.24 (s, 1 H), 8.73 (s, 1 H), 8.26 (s, 1 H), 8.10 (d, J=9 Hz, 1 H), 7.92 (d, J=8 Hz, 1 H), 7.67 (d, J=9 Hz, 1 H), 7.03 (d, J=9 Hz, 1 H), 4.31 (q, J=7 Hz, 2 H), 1.32 (t, J=7 Hz, 3 H).

Example 36

Ethyl 6-(2-hydroxy-5-cyano-1H-indol-3-yl)nicotinate

To a solution of 5-cyanooxindole (360 mg, 2.27 mmol) in N,N-dimethylformamide (5 mL) was added sodium hydride (106 mg, 4.41 mmol). The greenish reaction mixture was stirred for 50 min whereafter 6-chloronicotinic acid ethyl ester (350 mg, 1.89 mmol) dissolved in N,N-dimethylformamide (5 mL) was added. The reaction mixture was heated at 110° C. for 30 min and water (50 mL) and saturated NH$_4$Cl (aq) (20 mL) was added, followed by extraction with ethyl acetate. The phases were separated and the organic phase contained the title compound as a precipitation that was filtered off. The solvent was concentrated in vacuo and additional product precipitated that was filtered to give 200 mg (34% yield) of the title compound in total: $^1$H NMR (DMSO-d6, 300 MHz) δ 14.50 (br s, 1 H), 11.00 (s, 1 H), 8.73 (s, 1 H), 7.95 (s, 2 H), 7.80 (s, 1 H), 7.48 (s, 1 H), 6.95 (d, J=7 Hz, 1 H), 4.50-4.15 (m, 2 H), 1.32 (t, J=7 Hz, 3 H).

Example 37

5-Pyridin-3-yl-1,3-dihydro-2H-indol-2-one

A mixture of 5-bromooxindole (0.95 g, 4.48 mmol), 3-(tri-n-butylstannyl)pyridine (1.65 g, 4.48 mmol), tetraethyl ammonium chloride (2.23 g, 13.4 mmol) and bis(triphenylphospine palladium (II) chloride (0.16 g, 0.22 mmol) in acetonitrile (20 mL) was heated at reflux over night. After cooling to ambient temperature the mixture was diluted with chloroform (100 mL) and a potassium fluoride solution (10%, 250 mL) was added. The mixture was filtered through Celite and the layers were separated. The organic layer was dried (Na$_2$SO$_4$) and the solvent was removed in vacuo. The residue was purified on a silica gel column using chloroform/ethanol, (50:1), as the eluent affording 165 mg (18% yield) of the title compound as a white solid: $^1$H NMR (DMSO-d6, 400 MHz) δ 9.64 (br s, 1 H), 7.97 (d, J=2 Hz, 1 H), 7.66 (dd, J=5, 1 Hz, 1 H), 7.21-7.10 (m, 1 H), 6.73 (s, 1 H), 6.73-6.65 (m, 1 H), 6.65-6.54 (m, 1 H), 6.08 (d, J=8 Hz, 1 H), 2.69 (s, 2 H); MS (ES) m/z 211 (M$^+$+1).

Example 38

5-Thien-2-yl-1,3-dihydro-2H-indol-2-one

The title compound was prepared as described for Example 37 using 5-bromooxindole and tri-n-butyl(2-thienyl)tin: MS (ES) n/z 216 (M$^+$+1).

Example 39

5-(2-Furyl)-1,3-dihydro-2H-indol-2-one

The title compound was prepared as described for Example 37 using 5-bromooxindole and tri-n-butyl(2-furyl)tin: MS (ES) m/z 200 (M$^+$+1).

Example 40

5-(Hydroxymethyl)-1,3-dihydro-2H-indol-2-one

To an ice-cooled mixture of methyl 2-oxoindoline-5-carboxylate (0.5 gram, 2.6 mmol) in a tetrahydrofuran/ethanol mixture (15:0.3 mL) was added lithium borohydride (115 mg, 5.2 mmol) in one portion. After 30 min, another portion of lithium borohydride (100 mg, 4.5 mmol) was added and the reaction solution was stirred for 4 h at room temperature. A third portion of lithium borohydride (200 mg, 9.2 mmol) and ethanol (0.3 mL) were added and the reaction solution was stirred for 14 h at room temperature. The reaction was quenched with water (10 mL) and an aqueous saturated ammonium chloride solution (30 mL) and extracted with ethyl acetate. The combined organic phases were dried (Na$_2$SO$_4$) and evaporated in vacuo. The crude product was purified on a silica gel column using methylene chloride/methanol, (10:1) as the eluent to give 140 mg (33% yield) of the title compound: $^1$H NMR (DMSO-d6, 300 MHz) δ 10.3

(br s, 1 H), 7.14 (s, 1 H), 7.09 (d, J=8 Hz, 1 H), 6.74 (d, J=8 Hz, 1 H), 5.03 (t, J=6 Hz, 1 H), 4.41 (7, J=6 Hz, 2 H), 3.44 (s, 2 H).

Example 41

2-Oxoindoline-5-carbaldehyde

Chromium(VI) oxide (240 mg, 2.4 mmol) was added to ice-cooled pyridine (3 mL). To the formed yellow suspension was added additional pyridine (2 mL) and 5-(hydroxymethyl)-1,3-dihydro-2H-indol-2-one (130 mg, 0.8 mmol) dissolved in pyridine (3 mL). The reaction was quenched after 15 min by the addition of water (50 mL) and extracted with ethyl acetate. The organic phases were dried ($Na_2SO_4$) and evaporated in vacuo. The crude product was purified on a silica gel column using methylene chloride/methanol, (10:1), as the eluent to give 60 mg (46% yield) of the title compound.

Example 42

5-(1,3-Oxazol-5-yl)-1,3-dihydro-2H-indol-2-one

A mixture of 2-oxoindoline-5-carbaldehyde (60 mg, 0.38 mmol), tosylmethyl isocyanide (145 mg, 0.75 mmol) and potassium carbonate (103 mg, 0.75 mmol) in methanol (20 mL) was heated at reflux for 2 h. The mixture was concentrated in vacuo and diluted with an aqueous saturated solution of sodium hydrogencarbonate and extracted with methylene chloride. The combined organic layers were dried ($Na_2SO_4$) and evaporated in vacuo. The crude product was purified on a silica gel column using heptane/ethyl acetate, (1:4), as the eluent to give 40 mg (53% yield) of the title compound: $^1$H NMR (DMSO-d6, 300 M ) δ 10.54 (br s, 1 H), 8.36 (br s, 1 H), 7.64-7.44 (m, 3 H), 6.89 (d, J=8 Hz, 1 H), 3.54 (br s, 2 H).

Example 43

5-(Chloroacetyl)-1,3-dihydro-2H-indol-2-one

To a mixture of aluminum trichloride (17 gram, 128 mmol) and chloroacethyl chloride (3 gram, 2.65 mmol) in carbon disulfide (40 mL) was oxindole (2.73 gram, 20.5 mmol) added and the mixture was stirred at reflux for 3.5 h. The mixture was cooled to room temperature and carefully quenched with cooled water (50 mL). The quenched reaction mixture was stirred for 2 h and the formed precipitate was filtered and washed two times with water. The solid was dried to give 2.3 gram (53% yield) of the title compound: $^1$H NMR (DMSO-d6, 300 MHz) δ 10.82 (br s, 1 H), 7.87 (d, J=8 Hz, 1 H), 7.82 (s, 1 H), 6.92 (d, J=8 Hz, 1 H), 5.08 (s, 2 H), 3.57 (s, 2 H).

Example 44

5-(1,3-Thiazol-4-yl)-1,3-dihydro-2H-indol-2-one

A suspension of 5-(chloroacetyl)-1,3-dihydro-2H-indol-2-one (630 mg, 3 mmol), thioformamide (30 mL, 30 mmol; described in: *J. Med. Chem.* 1995, 858-868) and triethylamine (0.42 mL, 3 mmol) in dioxane was heated at 110° C. for 3 h. Additional thioformamide (10 mL, 10 mmol) was added and the reaction was stirred at 110° C. for 2 h. This batch was combined with an new batch starting from 230 mg of 5-(chloroacetyl)-1,3-dihydro-2H-indol-2-one and the combined reaction mixtures was concentrated to approximately 10 mL and an aqueous saturated sodium hydrogencarbonate solution (50 mL) was added and the solution was extracted with ethyl acetate. The combined organic layers were dried ($Na_2SO_4$) and evaporated in vacuo. The crude product was purified on a silica gel column using heptane/ethyl acetate, (1:2), as the eluent to give 400 mg (35% yield) of the title compound: $^1$H NMR (DMSO-d6, 300 MHz) δ 10.47 (s, 1 H), 9.15 (s, 1 H), 7.97 (s, 1 H), 7.83 (br s, 2 H), 6.87 (d, J=8 Hz, 1 H), 3.54 (s, 2 H); MS (ES) m/z 217 ($M^+$+1).

Example 45

5-(2-Methyl-1,3-thiazol-4-yl)-1,3-dihydro-2H-indol-2-one

A suspension of 5-(chloroacetyl)-1,3-dihydro-2H-indol-2-one (1.5 g, 7.15 mmol) and thioacetamide (540 mg, 7.15 mmol) in acetic acid (18 mL) was heated at 80° C. for 3 h. The mixture was cooled to room temperature and the formed precipitate was filtered and washed with ethyl acetate two times and diethyl ether two times and the solid was dried under vacuo to give 1.5 gram (91% yield) of the title compound: $^1$H NMR (DMSO-d6, 300 MHz) δ 10.49 (s, 1 H), 7.90-7.70 (m, 3 H), 6.85-6.75 (m, 1 H), 3.55 (s, 2 H), 2.70 (s, 3 H).

Example 46

3-[5-(Morpholin-4-ylmethyl)-1-oxidopyridin-2-yl]-5-pyridin-3-yl-1H-indol-2-ol

To a suspension of sodium hydride (0.05 g, 1.2 mmol, 60% dispersion in oil, pre-washed with hexane) in N,N-dimethylformamide (3 mL) was added a solution of 5-pyridin-3-yl-1,3-dihydro-2H-indol-2-one (0.19 g, 0.90 mmol) in N,N-dimethylformamide (4 mL). The mixture was stirred for 20 min under nitrogen atmosphere. 2-Chloro-5-(morpholin-4-ylmethyl)pyridine 1-oxide (0.14 g, 0.60 mmol), dissolved in N,N-dimethylformamide (3 mL) was added dropwise and the mixture was stirred at room temperature for 2 h and then heated at 130° C. for 1.5 h. The solvent was evaporated in vacuo and the residue was partitioned between 2 M HCl and ethyl acetate and the phases were separated. The aqueous layer was alkalized by addition of $NaHCO_3$ (s) and extracted with ethyl acetate. The organic layer was dried ($Na_2SO_4$) and the solvent was removed in vacuo affording 200 mg of the title compound as a yellow solid: MS (ES) m/z 403 ($M^+$+1).

Example 47

3-[5-(Morpholin-4-ylmethyl)-1-oxidopyridin-2-yl]-5-thien-2-yl-1H-indol-2-ol

The title compound was prepared as described for Example 46 using 5-thien-2-yl-1,3-dihydro-2H-indol-2-one: MS (ES) m/z 408 ($M^+$+1).

Example 48

5-(2-Furyl)-3-[5-(morpholin-4-ylmethyl)-1-oxidopyridin-2-yl]-1H-indol-2-ol

The title compound was prepared as described for Example 46 using 5-(2-furyl)-1,3-dihydro-2H-indol-2-one: MS (ES) m/z 392 ($M^+$+1).

Example 49

2-(5-Cyano-2-hydroxy-1H-indol-3-yl)-N-[2-(dimethylamino)ethyl]isonicotinamide

To a suspension of sodium hydride (0.15 g, 3.70 mmol, 60% dispersion in oil, pre-washed with hexane) in N,N-dimethylformamide (3 mL) was added a solution of 5-cyanooxindole (0.29 g, 1.84 mmol) in N,N-dimethylformamide (4 mL). The mixture was stirred for 30 min under a nitrogen atmosphere. 2-Chloro-N-[2-(dimethylamino)ethyl]isonicotinamide (0.21 g, 0.92 mmol) dissolved in N,N-dimethylformamide (4 mL) was added dropwise and the mixture was stirred at room temperature for 30 min and then heated at 150° C. for 45 min. The solvent was evaporated in vacuo and the residue was partitioned between ethyl acetate and water. A 2 M aqueous HCl solution was added until pH 2 and the mixture was extracted with ethyl acetate. To the aqueous layer, a 45% aqueous NaOH solution was added until pH 11 and the suspension was extracted with ethyl acetate. The aqueous layer was concentrated in vacuo and the crude product was purified by preparative HPLC (column: Xterra, 19×300 mm, eluent: 0.05 M $NH_4OAc$ buffert/acetonitrile, 9:1 to 3:7) to give 15 mg (5% yield) of the title compound as a red solid: $^1H$ NMR (DMSO-$d_6$, 400 MHz) δ 14.88 (br s, 1 H), 11.03 (br s, 1 H), 9.10 (br s, 1 H), 8.28 (d, J=6 Hz, 1 H), 8.04-7.96 (m, 1 H), 7.95-7.83 (m, 1 H), 7.42-7.34 (m, 1 H), 7.13-7.02 (m, 2 H), 3.62-3.50 (m, 2 H), 2.86-2.69 (m,.2 H), 2.58-2.29 (m, 6 H); MS (TSP) m/z 350 ($M^+$+1).

Example 50

2-Hydroxy-3-{4-[(4-methylpiperazin-1-yl)carbonyl]pyridin-2-yl}-1H-indole-5-carbonitrile hydrochloride The reaction was performed as described in Example 49 using 5-cyanooxindole and 1-(2-chloroisonicotinoyl)-4-methylpiperazine. The crude product was purified on a silica gel column using chloroform/ethanol/conc. $NH_3$(aq), (100:10:1), as the eluent. The base (20 mg) was dissolved in chloroform and a solution of HCl in diethyl ether was added until acidic pH. The formed precipitation was filtered and washed with diethyl ether. Drying in vacuo afforded 10 mg the title compound as a red solid. Yield: 2%: $^1H$ NMR ($D_2O$, 400 MHz) δ 7.82-7.77 (m, 1 H), 7.18-7.11 (m, 1 H), 7.09-7.05 (m, 1 H), 7.04-6.98 (m, 1 H), 6.78-6.71 (m, 1 H), 6.67-6.61 (m, 1 H), 4.05-3.94 (m, 1 H), 3.93-3.82 (m, 1 H), 3.67-3.48 (m, 2 H), 3.48-3.37 (m, 1 H), 3.35-3.04 (m, 3 H), 2.92-2.80 (m, 3 H); MS (TSP) m/s 362 ($M^+$+1).

Example 51

2-Hydroxy-3-{5-[(4-methylpiperazin-1-yl)carbonyl]pyridin-2-yl -1H-indole-5-carbonitrile A mixture of 5-cyanooxindole (213 mg, 1.35 mmol) and sodium hydride (72 mg, 1.80 mmol, 60% dispersion in oil) in N,N-dimethylforrnamide (4 mL) was stirred at room temperature for 10 min. A solution of 1-[(6-chloropyridin-3-yl)carbonyl]-4-methylpiperazine (216 mg, 0.901 mmol; described in: Thunus, L. *Ann. Pharm. Fr.* 1977, 35(5-6), 197-203) in N,N-dimethylformamide (2 mL) was added dropwise. The reaction was stirred at room temperature for 3 h, then at 50° C. for 2.5 h. The solvent was removed in vacuo, and the residue was partitioned between chloroform and water. The phases were separated and the pH of the water phases was adjusted to 8 with a 2 M aqueous solution of HCl. The aqueous layer was extracted with ethyl acetate and the organic layers were dried ($Na_2SO_4$), combined, and the solvent was removed in vacuo affording an orange semi-solid. The material was purified on a silica gel column using chloroform/methanol, (8:2), as the eluent affording 24 mg (7% yield) of the title compound as a yellow solid: mp decomposes >295° C.; $^1H$ NMR ($CDCl_3$, 400 MHz) δ 7.95 (s, 1 H), 7.91 (s, 1 H), 7.74 (dd, J=9, 2 Hz, 1 H), 7.69 (s, 1 H), 7.48 (d, J=9 Hz, 1 H), 7.36 (dd, J=8, 1 Hz, 1 H), 7.06 (d, J=8 Hz, 1 H), 3.69 (br s, 4 H); 2.48 (br s, 4 H), 2.36 (s, 3 H); MS (TSP) m/z 362 ($M^+$+1).

Example 52

2-Hydroxy-3-[5-(morpholin-4-ylmethyl)pyridin-2-yl]-1H-indole-5-carbonitrile hydrochloride To a suspension of 5-cyanooxindole (720 mg, 4.55 mmol) in N,N-dimethylformamide (5 mL) was added sodium hydride (248 mg, 6.2 mmol, 60% dispersion in oil). After 15 min, was added 4-[(6-chloropyridin-3-yl)methyl]morpholine (323 mg, 1.52 mmol; described in: Maienfisch, P. et al. *J. Med. Chem.* 2000, 43, 5003) to the solution. The reaction mixture was heated at reflux for 1 h. The solvent was removed in vacuo, and the residue was partitioned between ethyl acetate and water. A 2 M aqueous HCl solution was added to the ethyl acetate and water mixture until slightly acidic pH, and then $NaHCO_3$ (s) was added until saturation. The mixture was extracted with ethyl acetate. The organic layer was washed with brine, dried ($Na_2SO_4$) and the solvent was removed in vacuo. The crude product was dissolved in a mixture of methanol and ethyl acetate and was cooled on ice. A solution of HCl in diethyl ether was added until acidic pH. Approximately half of the solvent volume was removed in vacuo. The precipitated hydrochloride salt was filtered, washed with ethyl acetate, and dried in vacuo. The salt was converted back to the base by partitioning between ethyl acetate and an aqueous saturated $NaHCO_3$ solution. The obtained material (142 mg) was purified on a silica gel column using chloroform/ethanol, (9:1), as the eluent affording 34 mg (7% yield) of the title compound as the base as a yellow solid: $^1H$ NMR ($CDCl_3$, 400 MHz) δ 14.96 (br s, 1 H), 8.83 (br s, 1 H), 7.79 (dd, J=9, 1 Hz, 1 H), 7.69 (s, 1 H), 7.63 (s, 1 H), 7.50 (d, J=9 Hz, 1 H), 7.29-7.26 (m, 1 H), 7.06 (d, J=8 Hz, 1 H), 3.75-3.72 (m, 4 H), 3.44 (s, 2 H), 2.50-2.49 (m, 4 H).

The base was dissolved in a mixture of methanol, dichloromethane, and ethyl acetate (15 mL total volume) and cooled on ice. A solution of HCl in diethyl ether (1 M) was added until acidic pH. Approximately half of the solvent volume was removed in vacuo, and ethyl acetate was added. The precipitated hydrochloride salt was filtered, washed with ethyl acetate, and dried in vacuo at 40° C. affording 33 mg (87% yield from the base) as a yellow solid: $^1H$ NMR (DMSO-d6, 400 MHz) δ 14.75 (br s, 1 H), 11.36 (br s, 1 H), 10.98 (s, 1 H), 8.30 (s, 1 H), 8.07-8.02 (m, 2 H), 7.90 (d, J=9 Hz, 1 H), 7.32 (d, J=8 Hz, 1 H), 7.02 (d, J=8 Hz, 1 H), 4.29 (s, 2 H), 3.98-3.94 (m, 2 H), 3.82-3.75 (m, 2 H), 3.37-3.32 (m, 2 H), 3.11-3.08 (m, 2 H); $^{13}C$ NMR (DMSO-d6, 100 MHz) δ 168.9, 148.4, 142.6, 139.7, 137.4, 124.8, 124.8, 120.8, 119.4, 118.4, 113.1, 108.9, 101.5, 85.6, 63.0, 55.5, 50.2; MS (TSP) m/z 335 ($M^+$+1).

Example 53

2-Hydroxy-3-[6-(2-morpholin-4-ylethoxy)pyrimidin-4-yl]-1H-indole-5-carbonitrile

To a solution of 5-cyanooxindole (411 mg, 2.60 mmol) in N,N-dimethylformamide (4 mL) was added sodium hydride (181 mg, 4.52 mmol, 60% dispersion in oil). After 10 min, a solution of 4-(2-[(6-chloropyrimidin-4-yl)oxy]ethyl )morpholine (367 mg, 1.51 mmol) in N,N-dimethylformamide (1.5 mL) was added dropwise. The mixture was stirred at room temperature for 3 h. The solvent was removed in vacuo, and the residue was suspended in a 2 M aqueous HCl solution and washed twice with ethyl acetate. The aqueous layer was alkalized to pH 8 by adding a 45% aqueous NaOH solution. The obtained suspension was extracted twice with ethyl acetate. The combined phases were washed with brine, dried ($Na_2SO_4$) and the solvent was removed in vacuo. The crude product was purified on a silica gel column using chloroform/ethanol, (9:1), to chloroform/methanol, (8:2), as the eluent affording 172 mg (31% yield) of the title compound as a yellow solid: $^1$H NMR (DMSO-d6, 400 MHz) δ 10.89 (br s, 1 H), 8.62 (s, 1 H), 8.02 (s, 1 H), 7.30 (d, J=7 Hz, 1 H), 6.97 (d, J=8 Hz, 1 H), 6.83 (br s, 1 H), 4.52 (t, J=5 Hz, 2 H), 3.60 (t, J=4 Hz, 4 H), 2.77 (m, 2 H), 2.54 (m, 4 H); MS (TSP) m/z 366 ($M^+$+1).

Example 54

2-Hydroxy-3-{5-[(4-methylpiperazin-1-yl)methyl]pyridin-2-yl}-1H-indole-5-carbonitrile hydrochloride

A mixture of 5-cyanooxindole (694 mg, 4.39 mmol) and sodium hydride (234 mg, 5.85 mmol, 60% dispersion in oil) in N,N-dimethylformamide (2.5 mL) was stirred at room temperature for 15 min. To the greenish solution was added a solution of 1-[(6-chloropyridin-3-yl)methyl]-4-methylpiperazine (330 mg, 1.46 mmol) in N,N-dimethylformamide (1.2 mL) and the mixture was heated at 150° C. for 30 min. The mixture was allowed to cool and the solvent was removed in vacuo. The residue was suspended in a 2 M aqueous HCl solution and washed twice with ethyl acetate. The aqueous layer was alkalized with $NaHCO_3$ (s) until saturation followed by three extractions with ethyl acetate. The organic layers were combined, dried ($Na_2SO_4$), and the solvent was removed in vacuo. The obtained material was purified twice by column chromatography on silica using chloroform/methanol/conc. $NH_3$(aq), (90:10:0.5), as the eluent affording 56 mg of an oil. 38 mg of the oil was purified by preparative HPLC (column: Xterra, 19×300 mm, eluent: 0.05 M $NH_4OAc$ buffert/acetonitrile, 9:1-3:7) affording 29 mg (6% yield) of the title compound as a yellow solid: mp decomposes>240° C.; $^1$H NMR ($CDCl_3$, 400 MHz) δ 8.74 (s, 1 H), 7.78 (d, J=9 Hz, 1 H), 7.70 (s, 1 H), 7.64 (s, 1 H), 7.50 (d, J=9 Hz, 1 H), 7.29 (m, 1 H), 7.06 (d, J=8 Hz, 1 H), 3.44 (s, 2 H), 2.52 (br s, 8 H), 2.31 (s, 3 H); $^{13}$C NMR ($CDCl_3$, 100 MHz) δ 169.1, 149.6, 141.7, 136.1, 134.2, 125.4, 124.7, 123.6, 121.0, 119.7, 118.4, 109.3, 103.2, 85.4, 59.0, 55.0, 52.9, 45.9.

10 mg of the solid was dissolved in a mixture of ethyl acetate, methylene chloride, and a small volume of methanol (10 mL total volume). The solution was cooled on ice and HCl in diethyl ether (1 M) was added until acidic pH. Approximately ⅔ of the solvent volume was removed in vacuo and ethyl acetate was added. The precipitated hydrochloride salt was filtered, washed with ethyl acetate and dried in vacuo affording 12 mg of the title compound as an orange solid: $^1$H NMR ($D_2O$, 400 MHz) δ 7.78 (s, 1 H), 7.68-7.65 (m, 1 H), 7.47 (s, 1 H), 7.34-7.31 (m, 1 H), 7.14-7.11 (m, 1 H), 6.93-6.6.90 (m, 1 H), 3.62-3.48 (m, 10 H), 2.77 (s, 3 H); MS (TSP) m/z 348 ($M_+$+1).

Example 55

6-(5-Cyano-2-hydroxy-1H-indol-3-yl)-N-[2-(dimethylamino)ethyl]-N-methylnicotinamide hydrochloride

A mixture of sodium hydride (330 mg, 8.2 mmol, 60% dispersion in oil, pre-washed with hexane) in N,N-dimethylformamide (2 mL) was added to 5-cyanooxindole (980 mg, 6.2 mmol) in N,N-dimethylformamide (4 mL). The formed brown mixture was stirred at room temperature for 20 min and 6-chloro-N-[2-(dimethylamino)ethyl]-N-methylnicotinamide (500 mg, 2.1 mmol) in N,N-dimethylformamide (3 mL) was added. The obtained red solution was heated at 150° C. for 30 min and was then allowed to reach room temperature overnight. The solvent was removed in vacuo and the residue was partitioned between a 2 M aqueous HCl solution and ethyl acetate. The mixture was alkalized to pH 8 by adding $NaHCO_3$ (s) and extracted with ethyl acetate. The combined extracts were dried ($Na_2SO_4$) and the solvent was removed in vacuo to afford 450 mg of a crude product. The residue was purified on a silica gel column using chloroform/methanol/conc. $NH_3$(aq), (80:19:1), as the eluent. Fractions containing product were collected, evaporated in vacuo and dried at 25° C. in vacuo to afford 70 mg. The residue was purified by preparative HPLC (column: Xterra, 19×300 mm, eluent: 0.05 M $NH_4OAc$ buffert/acetonitrile, 9:1-3:7). Fractions containing product were collected, evaporated in vacuo and dried at 25° C. in vacuo to afford 35 mg (4.6% yield) of the title compound as the base: $^1$H NMR ($D_2O$, 400 MHz) δ 7.89 (s, 1 H), 7.59 (d, J=9 Hz, 1 H), 6.96 (s, 1 H), 6.92 (d, J=8 Hz, 1 H), 6.84 (d, J=9 Hz, 1 H), 6.65 (d, J=8 Hz, 1 H), 3.76 (s, 2 H), 3.30 (s, 2 H), 3.07 (s, 3 H), 2.84 (s, 6 H).

10 mg of the base was dissolved in diethyl ether and treated with 5 M HCl in diethyl ether. The hydrochloride salt was dried at 25° C. in vacuo to afford 6 mg of the title compound as an orange powder: MS (ESP) m/z 364 ($M^+$+1).

Example 56

2-Hydroxy-3-{5-[(4-methylpiperazin-1-yl)sulfonyl]pyridin-2-yl-1H-indole-5-carbonitrile hydrochloride

The reaction was performed as described in Example 55 using 1-(6-chloropyridine-3-sulfonyl)-4-methylpiperazine (described in: Thunus L., Annales Pharmaceutiques Francaises 1977, 35, 197-203). Yield: 9.8%: $^1$H NMR ($D_2O$, 400 MHz) δ 8.12 (s, 1 H), 7.60 (d, J=10 Hz, 1 H), 7.13 (s, 1 H), 7.00 (dd, J=8, 2 Hz, 1 H), 6.93 (d, J=9 Hz, 1 H), 6.73 (dd, J=8, 2 Hz, 1 H), 3.91 (d, J=13 Hz, 2 H), 3.60 (d, J=11 Hz, 2 H), 3.24 (app. t, J=11 Hz, 2 H), 3.02 (app. t, J=12 Hz, 2 H), 2.89 (s, 3 H); MS (TSP) m/z 398 ($M^+$+1).

Example 57

6-(5-Cyano-2-hydroxy-1H-indol-3-yl)-N-(2-pnyrolidin-1-ylethyl)pyridine-3-sulfonamide hydrochloride

The reaction was performed as described in Example 55 using 6-chloro-N-(2-pyrrolidin-1-ylethyl)pyridine-3-sulfonamide. Purification on a silica gel column using chloroform/methanol/conc. $NH_3$(aq), (80:19:1), as the eluent gave the title compound as the base. Yields: 9.8%. 15 mg of the base was dissolved in methylene chloride/tetrahydrofuran/methanol (3 mL total volume) and treated with 5 M HCl in diethyl ether. The hydrochloride salt was dried at 40° C. in vacuo to afford 11 mg of the title compound as an orange powder: $^1$H NMR (D$_2$O, 400 MHz) δ 7.96 (s, 1 H), 7.47 (d, J=9 Hz, 1 H), 6.87 (s, 1 H), 6.74 (d, J=8 Hz, 1 H), 6.66 (d, J=9 Hz, 1 H), 6.50 (d, J=8 Hz, 1 H), 3.61 (m, 2 H), 3.25 (m, 4 H), 3.02 (m, 2 H), 1.97 (m, 4 H); MS (TSP) m/z 412 (M$^+$+1).

Example 58

2-Hydroxy-3-[5-(morpholin-4-ylmethyl)pyridin-2-yl]-1H-indole-5-carbonitrile

To a suspension of sodium hydride (105 mg, 2.62 mmol, 60% in oil) in N,N-dimethylformamide (2 mL) was added 5-cyanooxindole (310 mg, 1.96 mmol). The mixture was stirred at room temperature for 10 min. To the obtained yellowish solution was added 2-chloro-5-(morpholin-4-ylmethyl)pyridine 1-oxide (299 mg, 1.31 mmol) and the mixture was heated under nitrogen at 130° C. for 30 min. The dark reaction mixture was allowed to cool and the solvent was removed in vacuo. The residue was partitioned between a 2 M aqueous solution of HCl and ethyl acetate. The aqueous layer was carefully saturated with NaHCO$_3$ (s) and extracted twice with ethyl acetate. The two last organic layers were combined, dried (Na$_2$SO$_4$) and the solvent was removed in vacuo. The residue was dissolved in ethyl acetate (50 mL) and a concentrated solution of phosphorus trichloride (0.5 mL, 5.7 mmol) in ethyl acetate (3 mL) was added. A yellowish precipitate was formed. The mixture was stirred at room temperature overnight and then heated at 60° C. for 30 min and finally at reflux for 10 min. The mixture was allowed to cool and was then diluted with ethyl actetate and washed with a saturated aqueous NaHCO$_3$ solution. The aqueous layer was extracted repeatedly with ethyl acetate. The combined organic layers were dried (Na$_2$SO$_4$) and the solvent was removed in vacuo. The residue was purified on a silica gel column using chloroform/ethyl acetate, (9:1), as the eluent affording 195 mg (45% yield) of the title compound as a yellow solid: mp 228-230° C.; $^1$H NMR (DMSO-d6, 400 MHz) δ 14.79 (br s, 1 H), 10.87 (s, 1 H), 8.10 (s, 1 H), 7.91 (s, 1 H), 7.84 (d, J=9 Hz, 1 H), 7.79 (dd, J=9, 1 Hz, 1 H), 7.28 (d, J=8 Hz, 1 H), 7.00 (d, J=8 Hz, 1 H), 3.58 (t, J=4 Hz, 4 H), 3.39 (s, 2 H), 2.38 (br s, 4 H); $^{13}$C NMR (DMSO-d6, 100 MHz) δ 168.6, 148.4, 142.0, 136.9, 135.9, 125.2, 124.0, 122.3, 121.0, 118.7, 118.3, 108.7, 101.2, 84.4, 66.1, 58.3, 52.8; MS (ESP) m/z 335 (M$^+$+1).

Example 59

2-Hydroxy-3-[5-(pyrrolidin-1-ylmethyl)pyridin-2-yl]-1H-indole-5-carbonitrile hydrochloride To a suspension of sodium hydride (60% in mineral oil, 72 mg, 1.80 mmol) in N,N-dimethylformamide (1 mL) was added 5-cyanooxindole (213 mg, 1.35 mmol), and the mixture was stirred at ambient temperature for 15 min. To the obtained brownish solution was added a solution of 2-chloro-5-(pyrrolidin-1-ylmethyl)pyridine 1-oxide (191 mg, 0.90 mmol) in N,N-dimethylformamide (1.5 mL). The obtained red solution was heated at 125° C. for 20 min, and was then allowed to cool. The mixture was dissolved in 2 M HCl(aq) and washed with ethyl acetate. The organic layer was extracted with 2 M HCl(aq). The combined aqueous layers were alkalized to saturation with NaHCO$_3$ (s), and extracted two times with ethyl acetate. The extracts were combined, dried (Na$_2$SO$_4$) and the solvent was removed in vacuo to give 270 mg of a crude product. The material was dissolved in ethyl acetate (15 mL), and a solution of phosphorus trichloride (0.25 mL, 2.87 mmol) in ethyl is acetate (3 mL) was added. An orange precipitate was immediately formed. The mixture was heated at reflux for 30 min, and was then allowed to cool. The mixture was partitioned between ethyl acetate and a saturated aqueous NaHCO$_3$ solution. The aqueous layer was extracted with another two portions of ethyl acetate. The combined organic layers were dried (Na$_2$SO$_4$) and the solvent was evaporated to give a crude product which was purified on a silica gel column using chloroform/methanol/conc. NH$_3$ (aq), (90:10:0.5), as the eluent affording 85 mg (37% yield) of the title compound as the free base as an orange solid: $^1$H NMR (CDCl$_3$, 400 MHz) δ 14.9 (br s, 1 H), 9.02 (s, 1 H), 7.78 (dd, J=9, 2 Hz, 1 H), 7.68 (s, 1 H), 7.60 (s, 1 H), 7.46 (d, J=9 Hz, 1 H), 7.25-7.22 (m, 1 H), 7.05 (d, J=8 Hz, 1 H), 3.56 (s, 2 H), 2.55-2.51 (m, 4 H), 1.83-1.79 (m, 4 H); MS (ES) m/z 319 (M$^+$+1). The base (65 mg) was dissolved in a mixture of ethyl acetate (20 mL), methylene chloride (10 mL), and methanol (2 mL), and was then cooled on an ice-bath. A solution of HCl in diethyl ether (1 M) was added until acidic pH. About 60% of the solvent volume was evaporated and to the residual suspension was added ethyl acetate. The obtained orange hydrochloride was filtered, washed with ethyl acetate, and dried in vacuo at 40° C. affording 65 mg (95% yield from the base) of the title compound as a brownish solid: $^1$H NMR (DMSO-d6, 400 Mz) δ 14.70 (br s, 1 H), 11.00 (br s, 1 H), 10.97 (s, 1 H), 8.31 (s, 1 H), 8.07 (dd, J=9, 1 Hz, 1 H), 8.02 (s, 1 H), 7.91 (d, J=8 Hz, 1 H), 7.32 (d, J=7 Hz, 1 H), 7.02 (d, J=7 Hz, 1 H), 4.29 (d, J=6 Hz, 2 H), 3.45-3.39 (m, 2 H), 3.09-3.02 (m, 2 H), 2.04-1.98 (m, 2 H), 1.92-1.87 (m, 2 H).

Example 60

2-Hydroxy-3-{5-[(4-methyl-1,4-diazepan-1-yl)methyl]pyridin-2-yl}-1H-indole-5-carbonitrile hydrochloride To a suspension of sodium hydride (60% in mineral oil, 263 mg, 6.58 mmol) in N,N-dimethylformamide (3 mL) was added 5-cyanooxindole (0.78 g, 4.94 mmol) in portions. The mixture was stirred at ambient temperature for 10 min. To the obtained brownish solution was added a solution of 1-[(6-chloro-1-oxidopyridin-3-yl)methyl]-4-methyl-1,4-diazepane (842 mg, 3.29 mmol) in N,N-dimethylformamide (3 mL). The reaction mixture was heated at 130° C. under a nitrogen atmosphere for 30 min. The dark mixture was allowed to cool and the solvent was removed in vacuo. To the residual oil was added 2 M HCl(aq) and the obtained suspension was washed twice with ethyl acetate. The aqueous layer was neutralized with 45% NaOH and alkalized to saturation with NaHCO$_3$ (s), and extracted two times with ethyl acetate, and once with tetrahydrofuran. The extracts were combined, dried (Na$_2$SO$_4$) and the solvent was removed in vacuo affording 1.0 g of the crude N-oxide: MS (ES) n/z 278 (M$^+$+1). Part of the material (841 mg, 2.23 mmol) was dissolved in acetonitrile (70 mL) during heating. To the warm solution was added phosphorus trichloride (1 mL, 11.1 mmol), dropwise initially and then at a faster rate. The obtained orange suspension was heated at reflux for 1 h, and was then allowed to cool. The precipitate was filtered, washed with acetonitrile, and dried in vacuo affording 780 mg of an orange residue. Part of the material (240 mg) was dissolved in H$_2$O. NaHCO$_3$ (s) was added until saturation, and the mixture was extracted three times with ethyl acetate and once with tetrahydrofuran. The combined organic layers were dried (Na$_2$SO$_4$ and MgSO$_4$), and the solvent was evaporated to give 165 mg of an oil which was purified on a silica gel column using chloroform/methanol/conc. $NH_3$(aq), (80:20:1), as the eluent to give 84 mg of the title compound as the free base as a brownish solid: $^1H$ NMR (DMSO-d6, 400 MHz) δ 14.70 (br s, 1 H), 10.79 (br s, 1 H), 8.11 (s, 1 H), 7.92 (s, 1 H), 7.87 (d, J=9 Hz, 1 H), 7.79 (d, J=8 Hz, 1 H), 7.25 (d, J=7 Hz, 1 H), 6.98 (d, J=7 Hz, 1 H), 3.53 (s, 2 H), 2.69-2.57 (m, 8 H), 2.30 (s, 3 H), 1.78-1.70 (m, 2 H). The base (66 mg) was converted to the hydrochloride using the method described for Example 59. Yield: 99% (calculated from the base) of the title compound as an orange solid: $^1H$ NMR ($D_2O$, 400 MHz) δ 7.91 (s, 1 H), 7.65 (dd, J=9, 2 Hz, 1 H), 7.01-6.95 (m, 3 H), 6.74 (d, J=7 Hz, 1 H), 4.32 (s, 2 H), 3.80-3.54 (m, 8 H), 2.97 (s, 3 H), 2.31 (br s, 2 H).

The following Examples, 61-62, were prepared as described for Example 60:

Example 61

2-Hydroxy-3-{5-[(4-pyrrolidin-1-ylpiperidin-1-yl)methyl]pyridin-2-yl}-1H-indole-5-carbonitrile hydrochloride Starting material: 2-chloro-5-[(4-pyrrolidin-1-yl)methyl]pyridine 1-oxide. The product was purified on a silica gel column using chloroform/methanol/conc. $NH_3$(aq), (90:10:0.5), as the eluent. Yield: 15% of the title compound as the base as an orange solid: $^1H$ NMR ($CDCl_3$, 400 MHz) δ 8.75 (br s, 1 H), 7.76 (dd, J=9, 2 Hz, 1 H), 7.69 (s, 1 H), 7.64 (s, 1 H), 7.49 (d, J=9 Hz, 1 H), 7.29-7.25 (m, 1 H), 7.05 (d, J=8 Hz, 1 H), 3.41 (s, 2 H), 2.88 (d, J=11 Hz, 2 H), 2.58 (br s, 4 H), 2.11-1.99 (m, 3 H), 1.90 (d, J=12 Hz, 2 H), 1.80 (br s, 4 H), 1.65-1.53 (m, 2 H); MS (ES) m/z 402 ($M^+$+1). The base (72 mg) was dissolved in a mixture of ethyl acetate (5 mL), methylene chloride (10 mL), and was then cooled on an ice-bath. A solution of HCl in diethyl ether was (1 M) added until acidic pH. The obtained orange hydrochloride was filtered, washed with ethyl acetate, and dried in vacuo at room temperature affording 68 mg (80% yield, calculated from the base) of the title compound as an orange solid: $^1H$ NR ($D_2O$, 400 MHz) δ 7.90 (s, 1 H), 7.71 (d, J=9 Hz, 1 H), 7.25 (s, 1 H), 7.15 (d, J=9 Hz, 1 H), 7.12 (d, J=8 Hz, 1 H), 6.89(d, J=8 Hz, 1 H), 4.00 (br s, 2 H), 3.55-3.41 (m, 5 H), 2.92-2.82 (m, 2 H), 2.43 (d, J=13 Hz, 2 H), 2.09 (br s, 4 H), 1.98-1.87 (m, 2 H).

Example 62

3-(5-{[3-(Dimethylamino)pyrrolidin-1-yl]methyl}pyridin-2-yl)-2-hydroxy-1H-indole-5-carbonitrile Starting material: 1-[(6-chloro-1-oxidopyridin-3-yl)methyl]-N,N-dimethylpyrrolidin-3-amine. The crude product was purified on a silica gel column using chloroform/methanol/conc. $NH_3$(aq), (85:15:1), as the eluent. The obtained material was purified further by preparative HPLC (column: Xterra, $C_8$, 7 μm, 19×300 mm; eluent: 0.1 M $NH_4OAc$ buffer/acetonitrile, 8:2 to 4:6) affording the title compound as an orange solid. Yield: 6%: $^1H$ NMR ($CDCl_3$, 400 MHz) δ 9.12 (br s, 1 H), 7.77 (d, J=9 Hz, 1 H), 7.71 (s, 1 H), 7.63 (s, 1 H), 7.49 (d, J=9 Hz, 1 H), 7.28-7.24 (m, 1 H), 7.06 (d, J=8 Hz, 1 H), 3.60-3.48 (m, 2 H), 2.95-2.89 (m, 1 H), 2.82-2.76 (m, 1 H), 2.72-2.68 (m, 1 H), 2.64-2.58 (m, 1 H), 2.53-2.48 (m, 1 H), 2.27 (s, 6 H), 2.09-2.00 (m, 1 H), 1.87-1.79(m, 1H); MS (ES) m/z 362 ($M^+$+1).

Example 63

2-Hydroxy-3-{5-[(4-methylpiperidin-1-yl)methyl]pyridin-2-yl}-1H-indole-5-carbonitrile To a suspension of sodium hydride (60% in mineral oil, 54 mg, 1.35 mmol) in N,N-dimethylformamide (1 mL) was added 5-cyanooxindole (161 mg, 1.02 mmol), and the mixture was stirred at ambient temperature for 10 min. To the obtained brownish solution was added a solution of 2-chloro-5-[(4-methylpiperidin-1-yl)methyl]pyridine 1-oxide (163 mg, 0.677 mmol) in N,N-dimethylformamide (1.5 mL). The reaction mixture was heated at 130° C. for 25 min, and was then allowed to cool. The solvent was removed in vacuo, and is to the residue was added 2 M HCl(aq). The obtained precipitate was partitioned between a saturated aqueous $NaHCO_3$ solution and ethyl acetate. The aqueous layer was extracted with another two portions of ethyl acetate. The combined organic layers were dried ($Na_2SO_4$), and the solvent was removed in vacuo affording a crude product. The material was dissolved in ethyl acetate (25 mL), and phosphorus trichloride (0.24 mL, 2.71 mmol) was added. An orange precipitate was immediately formed. The mixture was heated at reflux for 30 min, and was then allowed to cool. The mixture was partitioned between ethyl acetate and a saturated aqueous $NaHCO_3$ solution. The aqueous layer was extracted with another portion of ethyl acetate. The combined organic layers were dried ($Na_2SO_4$), and the solvent was evaporated. The crude product was purified on a silica gel column using chloroform/methanol, (95:5), as the eluent followed by preparative HPLC (column: Xterra, $C_8$, 7 μm, 19×300 mm; eluent: 0.1 M $NH_4OAc$ buffer/acetonitrile, 8:2 to 4:6) affording 4 mg (2% yield) of the title compound as an orange solid: $^1H$ NMR (acetone-d6, 400 MHz) δ 9.88 (br s, 1 H), 8.11 (d, J=1 Hz, 1 H), 7.90 (dd, J=9, 2 Hz, 1 H), 7.85 (d, J=9 Hz, 1 H), 7.82 (d, J=1 Hz, 1 H), 7.26 (dd, J=8, 2 Hz, 1 H), 7.11 (d, J=8 Hz, 1 H), 3.44 (s, 2 H), 2.91-2.86 (m, 2 H), 2.10-1.98 (m, 2 H), 1.65-1.59 (m, 2 H), 1.40-1.35 (m, 1 H), 1.28-1.16 (m, 2 H), 0.92 (d, J=7 Hz, 3 H); MS (ES) m/z 347 ($M^+$+1).

Example 64

2-Hydroxy-3-{5-[(4-phenylpiperazin-1-yl)methyl]pyridin-2-yl}-1H-indole-5-carbonitrile To a suspension of sodium hydride (60% dispersion in mineral oil, 45 mg, 1.12 mmol) in N,N-dimethylformamide (1 mL) was added 5-cyanooxindole (133 mg, 0.84 mmol). The mixture was stirred for 15 min, and a suspension of 1-[(6-chloro-1-oxidopyridin-3-yl)methyl]-4-phenylpiperazine (0.56 mmol) in N,N-dimethylformamide (2.3 mL) was added. The reaction mixture was heated at 130° C. for 10 min and was then allowed to cool to room temperature. The dark reaction mixture was acid/base-extracted using an Allex robot. The following steps were included: addition of HCl (aq), washing with ethyl acetate (to remove excess of 5-cyanooxindole), alkalization with (sat) $NaHCO_3$, and finally repeated extractions with ethyl acetate. The combined organic extracts were dried ($Na_2SO_4$), and the solvent was removed in vacuo. The residue was dissolved in ethyl acetate (10 mL), and phosphorus trichloride (0.2 mL, 2.24 mmol) was added. The resulting suspension was stirred at ambient temperature for 1.5 h, and then heated at reflux for 30 min. The reaction mixture was allowed to cool to room temperature. The mixture was washed with a saturated aqueous $NaHCO_3$ solution using an Allex robot. The aqueous layer was repeatedly extracted with ethyl acetate. The combined organic layers were dried (Na$_2$SO$_4$), and the solvent was evaporated to give 20 mg of an orange product which was purified on silca using chloroform/ethanol, (95:5), as the eluent. The obtained material (10 mg) was purified further by preparative HPLC (column: Xterra, C$_8$, 7 µm, 19×300 mm; eluent: 0.1 M NH$_4$OAc buffer/acetonitrile, 8:2 to 4:6) affording 5 mg (1.1% yield) of the title compound: $^1$H NMR (DMSO-d6, 400 MHz) δ 14.78 (br s, 1 H), 10.86 (s, 1 H), 8.14 (s, 1 H), 7.91 (s, 1 H), 7.86-7.82 (m, 2 H), 7.27 (d, J=8 Hz, 1 H), 7.23-7.16 (m, 2 H), 7.00 (d, J=8 Hz, 1 H), 6.93 (d, J=8 Hz, 2 H), 6.77 (t, J=7 Hz, 1 H), 3.46 (s, 3.16-3.12 (m, 4 H), 2.57-2.53 (m, 4 H); MS (ES) m/z 410 (M$^+$+1).

The following Examples, 65-70, were prepared as described for Example 64:

Example 65

3-[5-(Azetidin-1-ylmethyl)pyridin-2-yl]-2-hydroxy-1H-indole-5-carbonitrile

Starting material: 5-(azetidin-1-ylmethyl)-2-chloropyridine 1-oxide. The title compound was purified on a silica gel column using chloroform/methanol/conc. NH$_3$(aq), (90:10:0.5). Yield: 1%: $^1$H NMR (acetone-d6, 400 MHz) δ 9.86 (br s, 1 H), 8.10 (s, 1 H), 7.86-7.83 (m, 2 H), 7.81 (d, J=2 Hz, 1 H), 7.26 (dd, J=8, 2 Hz, 1 H), 7.11 (d, J=8 Hz, 1 H), 3.51 (d, J=1 Hz, 2 H), 3.22 (t, J=7 Hz, 4 H); MS (ES) m/z 305 (M$^+$+1).

Example 66

2-Hydroxy-3-[5-({4-[2-nitro-4-(trifluoromethyl)phenyl]piperazin-1-yl}methyl)pyridin-2-yl]-1H-indole-5-carbonitrile Starting material: 1-[(6-chloro-1-oxidopyridin-3-yl)methyl]-4-[2-nitro-4-(trifluoromethyl)phenyl]piperazine. Yield: 1%: $^1$H NMR (DMSO-d6, 400 MHz) δ 14.79 (br s, 1 H), 10.85 (s, 1 H), 8.15-8.12 (m, 2 H), 7.90 (s, 1 H), 7.87-7.80 (m, 3 H), 7.43 (d, J=9 Hz, 1 H), 7.27 (d, J=8 Hz, 1 H), 7.00 (d, J=8 Hz, 1 H), 3.47 (s, 2 H), 3.17-3.14 (m, 4 H), 2.55-2.52 (m, 4 H); MS (ES) m/z 523 (M$^+$+1).

Example 67

3-(5-{[(2-Cyanoethyl)(ethyl)amino]methyl}pyridin-2-yl)-2-hydroxy-1H-indole-5-carbonitrile Starting material: 3-[[(6-chloro-1-oxidopyridin-3-yl)methyl](ethyl)amino]propanenitrile. Yield: 1%: $^1$H NMR (DMSO-d6, 400 MHz) δ 14.80 (br s, 1 H), 10.84 (s, 1 H), 8.11 (s, 1 H), 7.93 (s, 1 H), 7.86 (d, J=9 Hz, 1 H), 7.83 (d, J=9 Hz, 1 H), 7.26 (d, J=8 Hz, 1 H), 6.99 (d, J=8 Hz, 1 H), 3.52 (s, 2 H), 2.73-2.70 (m, 2 H), 2.69-2.65 (m, 2 H), 2.53 (q, J=7 Hz, 2 H), 1.00 (t, J=7 Hz, 3 H); MS (ES) m/z 346 (M$^+$+1).

Example 68

3-(5-{[(4-Chlorobenzyl)(methyl)amino]methyl}pyridin-2-yl)-2-hydroxy-1H-indole-5-carbonitrile Starting material: N-(4-chlorobenzyl)-N-[(6-chloro-1-oxidopyridin-3-yl)methyl]-N-methylamine. Yield: 1%: $^1$H NMR (DMSO-d6, 400 MHz) δ 14.79 (br s, 1 H), 10.85 (s, 1 H), 8.15 (s, 1 H), 7.90 (s, 1 H), 7.85-7.82 (m, 2 H), 7.41-7.36 (m, 4 H), 7.27 (d, J=8 Hz, 1 H), 7.00 (d, J=8 Hz, 1 H), 3.52 (s, 2 H), 3.44 (s, 2 H), 2.11 (s, 3 H); MS (ES) m/z 401 (M$^+$−1).

Example 69

3-(5-{[(2-Furylmethyl)(methyl)amino]methyl}pyridin-2-yl)-2-hydroxy-1H-indole-5-carbonitrile Starting material: N-[(6-chloro-1-oxidopyridin-3-yl)methyl]-N-(2-furylmethyl)-N-methylamine. Yield: 4%: $^1$H NMR (DMSO-d6, 400 MHz) δ 14.80 (br s, 1 H), 10.86 (s, 1 H), 8.10 (s, 1 H), 7.91 (s, 1 H), 7.85 (d, J=9 Hz, 1 H), 7.79 (d, J=9 Hz, 1 H), 7.61 (d, J=1 Hz, 1 H), 7.27 (d, J=8 Hz, 1 H), 7.00 (d, J=8 Hz, 1 H), 6.43 (dd, J=3, 2 Hz, 1 H), 6.34 (d, 3 Hz, 1 H), 3.59 (s, 2 H), 3.42 (s, 2 H), 2.15 (s, 3 H); MS (ES) m/z 359 (M$^+$+1).

Example 70

2-Hydroxy-3-(5-{[methyl(phenyl)amino]methyl}pyridin-2-yl)-1H-indole-5-carbonitrile Starting material: N-[(6-chloro-1-oxidopyridin-3-yl)methyl]-N-methyl-N-phenylamine. The product was purified on a silica gel column using chloroform/methanol/conc. NH$_3$ (aq), (90:10:0.5), as the eluent. Yield 2%: $^1$H NMR (DMSO-d6, 400 MHz) δ 10.82 (br s, 1 H), 8.06 (s, 1 H), 7.91-7.68 (m, 3 H), 7.26-7.23 (m, 1 H), 7.22-7.16 (m, 2 H), 7.00-6.96 (m, 1 H), 6.80 (d, J=8 Hz, 2 H), 6.66 (t, J=7 Hz, 1 H), 4.49 (s, 2 H), 2.98 (s, 3 H); MS (ES) m/z 353 (M$^+$−1).

Example 71

2-Hydroxy-3-{5-[(3-methylpiperidin-1-yl)methyl]pyridin-2-yl}-1H-indole-5-carbonitrile To a suspension of sodium hydride (60% in mineral oil, 45 mg, 1.12 mmol) in N,N-dimethylformamide (1 mL) was added 5-cyanooxindole (133 mg, 0.84 mmol), and the mixture was stirred at ambient temperature for 10 min. To the obtained brownish solution was added a solution of 2-chloro-5-[(3-methylpiperidin-1-yl)methyl]pyridine 1-oxide (0.56 mmol) in N,N-dimethylformamide (1.5 mL). The reaction mixture was heated at 130° C. for 30 min, and was then allowed to cool. To the residue was added 2 M HCl(aq) and the obtained suspension was washed with ethyl acetate. The aqueous layer was neutralized with 45% NaOH(aq) and alkalized to saturation with NaHCO$_3$ (s), and extracted two times with ethyl acetate. The extracts were combined, dried (MgSO$_4$) and the solvent was removed in vacuo affording 84 mg of the crude product. The material was dissolved in ethyl acetate (10 mL), and to the solution was added phosphorus trichloride (0.2 mL, 2.24 mmol). The obtained orange suspension was heated at reflux for 1 h and was then allowed to cool. The precipitate was filtered, washed with ethyl acetate, and dried in vacuo affording 70 mg of an orange residue. The material was was purified by preparative HPLC (column: Xterra, C$_8$, 7 µm, 19×300 mm; eluent: 0.1 M NH$_4$OAc buffer/acetonitrile, 8:2 to 4:6) affording 15 mg (8% yield) of the title compund as an orange solid: $^1$H NMR (aceton-d6, 400 MHz) δ 9.86 (br s, 1 H), 8.11 (s, 1 H), 7.91 (dd, J=9, 2 Hz, 1 H), 7.84 (d, J=9 Hz, 1 H), 7.82 (d, J=1 Hz, 1 H), 7.26 (dd, J=8, 2 Hz, 1 H), 7.11 (d, J=8 Hz, 1 H), 3.44 (s, 2 H), 2.00-1.50 (m, 6 H), 0.95-0.81 (m, 4 H); MS (ES) m/z 347 (M$^+$+1).

The following Examples, 72-73, were prepared as described for Example 71:

Example 72

3-(5-{[Cyclohexyl(methyl)amino]methyl}pyridin-2-yl)-2-hydroxy-1H-indole-5-carbonitrile

Starting material: N-[(6-chloro-1-oxidopyridin-3-yl)methyl]-N-cyclohexyl-N-methylamine. Yield: 3%: $^1$H NMR (CDCl$_3$, 400 MHz) δ 8.64 (br s, 1 H), 7.79 (dd, J=9, 2 Hz, 1 H), 7.75 (s, 1 H), 7.68 (s, 1 H), 7.53 (d, J=9 Hz, 1 H), 7.30 (dd, J=8, 1 Hz, 1 H), 7.05 (d, J=8 Hz, 1 H), 3.52 (s, 2 H), 2.23 (s, 3 H), 1.88-1.80 (m, 5 H), 1.36-1.02 (m, 6 H); MS (ES) m/z 361 (M$^+$+1).

Example 73

2-Hydroxy-3-[5-(piperidin-1-ylmethyl)pyridin-2-yl]-H-indole-5-carbonitrile

Starting material: 2-chloro-5-(piperidin-1-ylmethyl)pyridine 1-oxide. Yield: 4%: $^1$H NMR (acetone-d6, 400 MHz) δ 9.85 (br s, 1 H), 8.11 (s, 1 H), 7.91 (dd, J=9, 2 Hz, 1 H), 7.85 (d, J=9 Hz, 1 H), 7.82 (d, J=1 Hz, 1 H), 7.26 (dd, J=8, 2 Hz, 1 H), 7.12 (d, J=8 Hz, 1 H), 3.43 (s, 2 H), 2.47-2.41 (m, 4 H), 1.61-1.54 (m, 4 H), 1.49-1.41 (m, 2 H); MS (ES) m/z 333 (M$^+$+1).

Example 74

3-{5-[(4-Methylpiperazin-1-yl)sulfonyl]pyridin-2-yl}-1H-indol-2-ol hydrochloride

Sodium hydride (46 mg, 60% dispersion in paraffin) was washed with hexane and dried in vacuo. N,N-Dimethylformamide (3 mL), oxindole (72 mg, 0.54 mmol) and 1-[(6-chloropyridin-3-yl)sulfonyl]-4-methylpiperazine (100 mg, 0.36 mmol; described in: Thunus L., *Annales Pharmaceutiques Francaises* 1977, 35, 197-203) were added to the sodium hydride and the reaction mixture was stirred at room temperature for 5 min. The reaction mixture was then heated for 10 min at 130° C. After cooling to room temperature, a saturated aqueous sodium hydrogen carbonate solution was added. The mixture was extracted twice with methylene chloride and the combined organic layers were dried (Na$_2$SO$_4$), filtrated and the solvent was removed in vacuo. The residue was purified on a silica gel column using a gradient ethyl acetate/methanol, (40:1 to 1:1), as the eluent. The product was dissolved in a mixture of methylene chloride (5 mL) and methanol (5 mL). Hydrogen chloride (3 mL, 1 M in diethyl ether) was added and stirring was continued for 10 min. The precipitate was washed with diethyl ether and dried in vacuo to give 50 mg (37% yield) of the title compound: $^1$H NMR (D$_2$O, 400 MHz) δ 7.95 (m, 1 H), 7.45 (d, J=2 Hz, 1 H), 7.43 (dd, J=9, 2 Hz, 1 H), 7.23 (m, 1 H), 7.14 (d, J=9 Hz, 1 H), 7.00 (m, 2 H), 3.88 (d, J=14 Hz, 2 H), 3.60 (d, J=12 Hz, 2 H), 3.23 (m, 2 H), 2.94 (m, 2 H), 2.90 (s, 3 H); MS (ES) m/z 373 (M$^+$+1).

Example 75

6-Chloro-3-{5-[(4-methylpiperazin-1-yl)sulfonyl]pyridin-2-yl}-1H-indol-2-ol hydrochloride

The title compound was prepared as described for Example 74 using 6-chlorooxindole. The base was purified on a silica gel column using a gradient chloroform/methanol, (100:0 to 4:1), as the eluent. The product was dissolved in a mixture of chloroform (10 mL) and methanol (10 mL). Hydrogen chloride (3 mL, 1 M in diethyl ether) was added and stirring was continued for 10 min. The precipitate was washed with diethyl ether and dried in vacuo to give 50 mg (29% yield) of the title compound: $^1$H NMR (DMSO-d6, 400 MHz) δ 10.95 (m, 1 H), 10.79 (s, 1 H), 8.49 (s, 1 H), 7.68 (m, 1 H), 7.64 (m, 1 H), 7.55 (d, J=8 Hz, 1 H), 6.98 (m, 1 H), 6.93 (m, 1 H), 3.74 (m, 2 H), 3.45 (m, 2 H), 3.12 (m, 2 H), 2.97 (m, 2 H), 2.75 (m, 3 H); MS (ES) m/z 407 (M$^+$+1).

Example 76

3-[5-(Morpholin-4-ylcarbonyl)pyridin-2-yl]-5-nitro-1H-indol-2-ol

Ethyl 6-(2-hydroxy-5-nitro-1H-indol-3-yl)nicotinate (0.327 g, 1.0 mmol) was suspended in benzene (13 mL) followed by the addition of morpholine (0.218 g, 2.5 mmol). The mixture was stirred (N$_2$ atmosphere) for 5 min at 0° C. To this mixture, trimethyl aluminum (2 M solution in hexane, 2 mL, 4 mmol) was added via a syringe. After 10 min the temperature was raised to 70° C. and the reaction mixture was stirred for 20 h then poured onto an ice-cold aqueous saturated NaHCO$_3$ solution and extracted with chloroform. The combined organic layer was concentrated and the light brown residue was purified on a silica gel column using chloroform/methanol/triethylamine, (50:10:1), as eluent to give 0.22 g (60% yield) of the title compound: $^1$H NMR (acetone-d6, 400 MHz) δ 8.47 (s, 1 H), 8.41 (s, H), 8.05 (d, J=8 Hz, 1 H), 7.99 (d, J=8 Hz, 1 H), 7.90 (d, J=8 Hz, 1 H), 7.19 (d, J=8 Hz, 1 H), 3.79 (br s, 2 H), 3.73 (br s, 4 H), 2.68 (br s, 4 H); MS (EI) m/z 369 (M+1$^+$).

Example 77

6-Bromo-3-[5-(morpholin-4-ylmethyl)pyridin-2-yl]-1H-indol-2-ol hydrochloride

To a N,N-dimethylformamide (1.5 mL) suspension of sodium hydride (60% dispersion in oil, 40 mg, 1.0 mmol, pre-washed with hexane) was added 6-bromoxindole (0.159 g, 0.75 mmol). The formed mixture was stirred for 5 min at room temperature followed by the is addition of 2-chloro-5-(morpholin-4-ylmethyl)pyridine 1-oxide (0.114 g, 0.5 mmol). The resulting reaction mixture was stirred (N$_2$ atmosphere) for 30 min at 120° C. The solvent was evaporated in vacuo and the residual oil was purified on a silica gel column using chloroform/methanol, (10:1), as eluent affording the N-oxide product. The N-oxide was dissolved in chloroform (3 mL) and phosphorus trichloride (0.412 g, 3.0 mmol) was added. The reaction mixture was stirred for 30 min at 60° C. and then cooled to room temperature. The mixture was quenched with methanol and concentrated. The residue was purified on a silica column using a chloroform/methanol gradient, (10:1 to 1:2), as the eluent to give 52 mg (4% yield) of the title compound as the base as brownish solid. The base (30 mg, 0.077 mmol) was dissolved in methylene chloride/methanol, (1:1), and treated with 1 M HCl in diethyl ether at 0° C. The resulting yellowish orange crystals were collected by filtration and washed with diethyl ether to give 5 mg (15% yield) of the title compound: $^1$H NMR (DMSO-d6, 400 MHz) δ 10.61 (s, 1 H), 8.59 (br s, 1 H), 8.23 (s, 1 H), 7.96 (s, 1 H), 7.70 (s, 1 H), 7.54 (d, J=8 Hz, 1 H), 7.09 (d, J=8 Hz, 1 H), 7.05 (s, 1 H), 4.17(br s, 2 H), 3.85 (br s, 4 H), 3.10 (br s, 4 H); MS (EI) m/z 388 (M$^+$), 390 (M$^+$+2).

Example 78

2-Hydroxy-3-[5-(morpholin-4-ylmethyl)pyridin-2-yl]-1H-indole-6-carbonitrile hydrochloride

The title compound was prepared as described for Example 77 using 6-cyanooxindole. The base was obtained as a yellow solid after purification by preparative HPLC (column: Xterra, $C_8$, 7 μm, 19×300 mm; eluent: 0.1 M $NH_4OAc$ buffer/acetonitrile, 8:2 to 4:6). Yield: 13%. The base was transformed to the yellow hydrochloride salt in 33% yield: $^1H$ NMR ($D_2O$, 400 MHz) δ 8.21 (s, 1 H), 8.04 (d, J=8 Hz, 1 H), 7.82 (d, J=8 Hz, 1 H), 7.64 (d, J=8 Hz, 1 H), 7.29 (s, 1 H), 7.28 (d, J=8 Hz, 1 H), 3.97 (s, 2 H), 3.69 (br s, 4 H), 2.65 (br s, 4 H); MS (EI) m/z 335 ($M^+$+1).

Example 79

5-Bromo-3-[5-(morpholin-4-ylmethyl)pyridin-2-yl]-1H-indol-2-ol hydrochloride

To a N,N-dimethylformamide (3.0 mL) suspension of sodium hydride (60% dispersion in oil, 0.480 g, 12.0 mmol, pre-washed with hexane) was added 5-bromooxindole (1.9 g, 9.0 mmol). The mixture was stirred for 10 min at 0° C. and for 5 min at room temperature. 2-Chloro-5-(morpholin-4-ylmethyl)pyridine 1-oxide (1.37 g, 6.0 mmol) was added and the resulting reaction mixture was stirred ($N_2$ atmosphere) for 50 min at 120° C., then cooled to room temperature. The N,N-dimethylformamide solution was diluted with an aqueous saturated $NaHCO_3$ solution and NaCl (s, 2 g) was added followed by extraction with chloroform and ethyl acetate. The combined organic phases were dried ($Na_2SO_4$) and concentrated in vacuo. The remaining N,N-dimethylformamide was removed by co-evaporation with toluene two times. The residual oil was dissolved in chloroform (10 mL) and phosphorus trichloride (3.0 g, 21.8 mmol) was added. The reaction mixture was stirred for 30 min at 60° C. and then cooled to room temperature. The mixture was poured into an aqueous saturated $NaHCO_3$ solution.

A brown precipitate was formed, which was filtered off, and the filtrate (containing some product) was treated separately (see bellow).

The brown solid was dissolved in methanol (150 mL) and insoluble materials were removed by filtration. This solution was concentrated to a brownish yellow solid, which was suspended in ethyl acetate (15 mL) and stirred overnight at room temperature. The yellow solid was collected by filtration and dried to afford 1.28 g of the product.

To the $NaHCO_3$ solution (filtrate, see above), NaCl(s) (2.0 g) was added followed by extractions with chloroform and ethyl acetate. The combined organic phases were dried ($Na_2SO_4$) and concentrated in vacuo. The residue was purified on a silica gel column using chloroform/methanol, (5:1) as eluent. The residue was suspended in ethyl acetate (15 mL) and stirred overnight at room temperature. The solid was filtered, dried to give 90 mg of the title compound as a yellow solid as the base. The obtained total amount of the base was 1.37 g (59% yield). A small amount of the free base (12 mg, 0.03 mmol) was dissolved in methylene chloride/methanol, (1:1) and treated with 1 M HCl in diethyl ether at 0° C. The resulting yellow crystals were collected by filtration and washed with diethyl ether to obtain 13 mg (100% yield) of the title compound: $^1H$ NMR (DMSO-d6, 400 MHz) δ 10.52 (s, 1 H), 8.09 (s, 1 H), 7.81 (d, J=8 Hz, 1 H), 7.70 (d, J=8 Hz, 1 H), 7.61 (s, 1 H), 7.04 (d, J=8 Hz, 1 H), 6.86 (d, J=8 Hz, 1 H), 3.62 (br s, 4 H), 3.40 (s, 2 H), 2.42 (br s, 4 H); MS (EI) m/z 388 ($M^+$), 390 ($M^+$+2).

Example 80

5,6-Dibromo-3-[5-(morpholin-4-ylmethyl)pyridin-2-yl]-1H-indol-2-ol hydrochloride

The title compound was prepared as described for Example 79 using 5,6-dibrom-1,3-dihydro-indol-2-one. The base (27% yield) was transformed to the hydrochloride salt. The salt was purified by re-crystallization from chloroform/methanol/diethyl ether and the crystals were washed with dimethylsulfoxide (1 mL) to give the title compound. Yield: 4%: $^1H$ NMR ($CDCl_3$, 400 MHz) δ 8.29 (s, 1 H), 7.75 (d, J=10 Hz, 1 H), 7.68 (s, 1 H), 7.62 (s, 1 H), 7.47 (d, J=10 Hz, 1 H), 7.21 (s, 1 H), 3.72 (br s, 4 H), 3.40 (s, 2 H), 2.48 (br s, 4 H).

Example 81

3-Fluoro-3-[5-(morpholin-4-ylmethyl)pyridin-2-yl]-2-oxoindoline-6-carbonitrile hydrochloride

2-Hydroxy-3-[5-(morpholin-4-ylmethyl)pyridin-2-yl]-1H-indole-6-carbonitrile (0.10 g, 0.3 mmol) was dissolved in tetrahydrofuran/dioxane, (1:1, 16 mL), under $N_2$ atmosphere and stirred at −20° C. for 5 min. To this mixture, sodium bis(trimethylsilyl)amide (1 M solution in tetrahydrofuran, 0.30 mL, 0.3 mmol) was added via syringe and the reaction was allowed to stir for 20 min at ambient temperature. 1-Fluoro-2,4,6-trimethylpyridinium triflate (0.112 g, 0.33 mmol) was added and the reaction was allowed to warm to room temperature and stirred for 16 h. The solvent was removed in vacuo and the residue was taken up in ethyl acetate and washed with an aqueous saturated $NaHCO_3$ solution. The organic phase was dried ($Na_2SO_4$) and evaporated in vacuo. The crude product was purified by preparative HPLC (column: Xterra, $C_8$, 10 μm, 19×300 mm; eluent: 0.05 M $NH_4OAc$ buffer/acetonitrile, 8:2-2:8) affording 50 mg (47% yield) of a yellowish brown solid. The solid (40 mg, 0.11 mmol) was dissolved in methylene chloride/methanol, (1:1), and treated with 1 M HCl in diethyl ether at 0° C. The resulting yellow crystals were collected by filtration and washed with diethyl ether to give 18 mg (42% yield) of the title compound: $^1H$ NMR (DMSO-d6, 400 MHz) δ 8.42 (s, 1 H), 7.96 (d, J=8 Hz, 1 H), 7.83 (d, J=8 Hz, 1 H), 7.50 (d, J=8 Hz, 1 H), 7.46 (d, J=8 Hz, 1 H), 7.44 (s, 1 H), 3.60 (br s, 4 H), 3.54 (s, 2 H), 2.38 (br s, 4 H): MS (EI) m/z 353 ($M^+$+1).

Example 82

3-5-[(4-Benzylpiperazin-1-yl)sulfonyl]pyridin-2-yl}-2-hydroxy-1H-indole-5-carbonitrile hydrochloride

To a suspension of sodium hydride (0.09 g, 2.2 mmol, 60% dispersion in oil, pre-washed with hexane) in N,N-dimethylformamide (3 mL), cooled on an ice-bath, was added a is solution of 5-cyanooxindole (0.32 g, 2.0 mmol) in N,N-dimethylformamide (3 mL). The mixture was stirred for 20 min under a nitrogen atmosphere and the ice-bath was removed. 1-Benzyl-4-[(6-chloropyridine-3-yl)sulfonyl]piperazine (0.35 g, 1.0 mmol), dissolved in N,N-dimethylformamide (4 mL), was added dropwise and the mixture was heated at 130° C. for 40 min. The solvent was evaporated in vacuo and the residue was partitioned between methylene chloride and aqueous $NaHCO_3$ (pH>7). The mixture was extracted with methylene chloride. The organic layers were combined, dried (Na$_2$SO$_4$) and the solvent was removed in vacuo. The crude product was purified on a silica gel column using chloroform/ethanol, (20:1), as the eluent. The base (120 mg) was dissolved in chloroform/methanol and a solution of HCl in diethyl ether (1 M) was added until acidic pH. The formed precipitation was filtered and washed with diethyl ether affording 71 mg (14% yield) of the title compound as a yellow solid: $^1$H NMR (DMSO-d6, 400 MHz) δ 11.15 (br s, 1 H), 10.54 (br s, 1 H), 8.54 (br s, 1 H), 8.01 (br s, 1 H), 7.88-7.81 (m, 1 H), 7.70 (dd, J=9, 2 Hz, 1 H), 7.56-7.47 (m, 2 H), 7.47-7.38 (m, 4 H), 7.06 (d, J=8 Hz, 1 H), 4.40-4.28 (m, 2 H), 3.83-3.66 (m, 2 H), 3.23-3.04 (m, 4 H), 3.04-2.88 (m, 2 H); MS (ES) m/z 474 (M$^+$+1).

Example 83

2-Hydroxy-3-(5-{[4-(3-methylbutyl)piperazin-1-yl]sulfonyl}pyridin-2-yl)-1H-indole-5-carbonitrile hydrochloride The title compound was prepared as described for Example 82 using 5-cyanooxindole and 1-[(6-chloropyridin-3-yl)sulfonyl]-4-(3-methylbutyl)piperazine. Yield: 5% of the title compound as a yellow solid: $^1$H NMR (DMSO-d6, 400 MHz) δ 11.15 (br s, 1 H), 10.63 (br s, 1 H), 8.57 (s, 1 H), 8.02 (s, 1 H), 7.94-7.81 (m, 1 H), 7.73 (d, J=9 Hz, 1 H), 7.41 (d, J=8 Hz, 1 H), 7.05 (d, J=8 Hz, 1 H), 3.82-3.67 (m, 2 H), 3.62-3.34 (m, 2 H), 3.20-2.92 (m, 6 H), 1.64-1.46 (m, 3 H), 0.86 (d, J=6 Hz, 6 H); MS (ES) m/z 454 (M$^+$+1).

Example 84

2-Hydroxy-3-{5-[(4-isopropylpiperazin-1-yl)sulfonyl]pyridin-2-yl}-1H-indole-5-carbonitrile hydrochloride The title compound was prepared as described for Example 82 using 5-cyanooxindole and 1-[(6-chloropyridin-3-yl)sulfonyl]-4-isopropylpiperazine. Yield: 30% of the title compound as a yellow solid; $^1$H NMR (DMSO-d6, 400 MHz) δ 11.56 (br s, 1 H), 10.68 (br s, 1 H), 8.57 (br s, 1 H), 8.02 (s, 1 H), 7.93-7.81 (m, 1 H), 7.74 (dd, J=9, 2 Hz, 1 H), 7.42 (dd, J=8, 1 Hz, 1 H), 7.06 (d, J=8 Hz, 1 H) 3.82-3.71 (m, 2 H), 3.58-3.31 (m, 3 H), 3.24-1.82 (m, 4 H), 1.24 (d, J=7 Hz, 6 H); MS (ES) m/z 304 (M$^+$+1).

Example 85

3-{5-[(4-Ethylpiperazin-1-yl)sulfonyl]pyridin-2-yl}-2-hydroxy-1H-indole-5-carbonitrile hydrochloride The title compound was prepared as described for Example 82 using 5-cyanooxindole and 1-[(6-chloropyridin-3-yl)sulfonyl]-4-ethylpiperazine. Yield: 4% of the title compound as a yellow solid: $^1$H NMR (DMSO-d6, 400 MHz) δ 11.15 (br s, 1 H), 10.75 (br s, 1 H), 8.56 (br s, 1 H), 8.04 (s, 1 H), 7.93-7.82 (m, 1 H), 7.73 (dd, J=9, 2 Hz, 1 H), 7.41 (dd, J=8, 1 Hz, 1 H), 7.05 (d, J=8 Hz, 1 H), 3.83-3.69 (m, 2 H), 3.69-3.42 (m, 2 H), 3.18-2.92 (m, 6 H), 1.20 (t, J=7.2 Hz, 3 H); MS (ES) m/z 412 (M$^+$+1).

Example 86

3-[5-(Morpholin-4-ylmethyl)pyridin-2-yl]-5-pyridin-3-yl-1H-indol-2-ol

To a solution of 3-[5-(morpholin-4-ylmethyl)-1-oxidopyridin-2-yl]-5-pyridin-3-yl-1H-indol-2-ol (200 mg, 0.6 mmol) in ethyl acetate (60 mL) was added phosphorus trichloride (0.4 mL). A yellow precipitate was formed and the mixture was refluxed for 3 h, and then diluted with ethyl acetate and washed with an aqueous saturated NaHCO$_3$ solution. The aqeous layer was extracted with two portions of ethyl acetate and one portion of chloroform. The organic- layers were combined, dried (Na$_2$SO$_4$) and concentrated in vacuo. The crude product was purified by preparative HPLC (column: Xterra, 19×300 mm, eluent: water/acetonitrile, (0:100 to 100:0), gradient) affording 6 mg (3% yield) of the title compound as a yellow solid: $^1$H NMR (DMSO-d6, 400 MHz) δ 10.50 (br s, 1 H), 8.92 (d, J=2 Hz, 1 H), 8.49 (dd, J=4, 1 Hz, 1 H), 8.12-8.06 (m, 1 H), 8.02 (s, 1 H), 7.90-7.71 (m, 1 H), 7.71-7.67 (m, 2 H), 7.43 (dd, J=8, 5 Hz, 1 H), 7.20 (d, J=8 Hz, 1 H), 6.98 (d, J=8 Hz, 1 H), 3.63-3.53 (m, 4 H), 3.40-3.24 (m, 2 H), 2.42-2.34 (m, 4 H); MS (ES) m/z 388 (M$^+$+1).

Example 87

3-[5-(Morpholin-4-ylmethyl)pyridin-2-yl]-5-thien-2-yl-1H-indol-2-ol hydrochloride The title compound was prepared as described for Example 86 using 3-[5-(morpholin-4-ylmethyl)-1-oxidopyridin-2-yl]-5-thien-2-yl-1H-indol-2-ol and phosphorus trichloride. The base was dissolved in chloroform/methanol, (3:1), and a solution of HCl in diethyl ether (1 M) was added until acidic pH. The formed precipitation was filtered, washed with diethyl ether and dried. Yield: 9% of the title compound as an yellow solid: $^1$H NMR (DMSO-d6, 400 MHz) δ 11.10 (br s, 1 H), 10.55 (s, 1 H), 8.21 (s, 1 H), 8.02-7.90 (m, 1 H), 7.85-7.62 (m, 2 H), 7.54-7.46 (m, 1 H), 7.46-7.37 (m, 1 H), 7.18 (d, J=8 Hz, 1 H), 7.15-7.06 (m, 1 H), 6.92 (d, J=8 Hz, 1 H), 4.24 (s, 2 H), 4.03-3.89 (m, 2 H), 3.84-3.51 (m, 2 H), 3.39-3.28 (m, 2 H) 3.16-3.05 (m, 2 H); MS (ES) m/s 392 (M$^+$+1).

Example 88

5-(2-Furyl)-3-[5-(moroholin-4-ylmethyl)pyridin-2-yl]-1H-indol-2-ol hydrochloride The title compound was prepared as described for Example 86 using 5-(2-furyl)-3-[5-(morpholin-4-ylmethyl)-1-oxidopyridin-2-yl]-1H-indol-2-ol. Yield: 6% of the title compound as an yellow solid: $^1$H NMR (DMSO-d6, 400 MHz) δ 10.26 (br s, 1 H), 10.56 (s, 1 H), 8.22 (s, 1 H), 8.03-7.94 (m, 1 H), 7.83-7.71 (m, 2 H), 7.66 (s, 1 H), 7.30 (d, j=8 Hz, 1 H), 6.98-6.86 (m, 2 H), 6.59-6.53 (m, 1 H), 4.31-4.10 (m, 2 H), 4.16-3.85 (m, 2 H), 3.85-3.70 (m, 2 H), 3.39-3.26 (m, 2 H), 3.17-3.01 (m, 2 H); MS (ES) m/z 376 (M$^+$+1).

Example 89

3-{3-Bromo-5-[(4-methylpiperazin-1-yl)sulfonyl]pyridin-2-yl}-5-nitro-1H-indol-2-ol hydrochloride The title compound was prepared as described for Example 55 using 5-nitrooxindole and 1-1-[(5-bromo-6-chloropyridin-3-yl)sulfonyl]-4-methylpiperazine. Purification on a silica gel column using chloroform/methanol, (8:2), as the eluent gave the title compound as the to base: ¹H NMR (CDCl₃, 400 MHz) δ 8.78 (br s, 1 H), 8.47 (br s, 1 H), 8.24 (dd, J=9, 2 Hz, 1 H), 7.96 (m, 1 H), 7.10 (d, J=9Hz, 1 H), 3.12 (m, 4 H), 2.50 (t, J=5 Hz, 4 H), 2.26 (s, 3 H).

The base was dissolved in chloroform and treated with 5 M HCl in diethyl ether. The hydrochloride was dried in vacuo and recrystallized from methanol to afford of the title is compound. Yield: 9.5%.

Example 90

3-[5-(Morpholin-4-ylmethyl)pyridin-2-yl]-5-(trifluoromethyl)-1H-indol-2-ol hydrochloride The title compound was prepared as described for Example 55 using 5-trifluoromethyloxindole. Yield: 8%: ¹H NMR (D₂O, 400 MHz) 7.87 (s, 1 H), 7.64 (d, J=9 Hz, 1 H), 7.55 (s, 1 H), 7.44 (d, J=9 Hz, 1 H), 7.29 (d, J=8 Hz, 1 H), 7.07(d, J=8 Hz, 1 H), 4.15 (s, 2 H), 4.06-3.85 (m, 4 H), 3.41-3.26 (m, 4 H).

Example 91

2-Hydroxy-3-{5-[(4-methylpiperazin-1-yl)sulfonyl]pyridin-2-yl}-1H-indole-6-carbonitrile hydrochloride The title compound was prepared as described for Example 55 using 6-cyanooxindole (1.5 equ) and 1-(6-chloropyridine-3-sulfonyl)-4-methylpiperazine (1 equ; described in: Thunus L., *Annales Pharmaceutiques Francaises* 1977, 35, 197-203). Purification on a silica gel column using chloroform/methanol/conc. NH₃(aq), (76:23: 1), as the eluent gave the title compound as the base. The base was dissolved in acetone/chloroform/methanol and treated with 5 M HCl in diethyl ether. The hydrochloride was dried to afford 24 mg (5.1% yield) of title compound: ¹H NMR (DMSO-d6, 400 MHz) δ 14.87 (s, 1 H), 11.00 (s, 1 H), 10.21 (s, 1 H), 8.62 (s, 1 H), 7.83 (s, 2 H), 7.73 (d, J=8 Hz, 1 H), 7.38 (d, J=8 Hz, 1 H), 7.23 (s, 1 H), 3.81-3.67 (m, 2 H), 3.57-3.38 (m, 2 H), 3.22-3.05 (m, 2 H), 2.97-2.85 (m, 2 H), 2.77 (s, 3 H).

Example 92

N-[(1-Ethylpyrrolidin-2-yl)methyl]-6-(2-hydroxy-5-nitro-1H-indol-3-yl)nicotinamide hydrochloride To a suspension of ethyl 6-(2-hydroxy-5-nitro-1H-indol-3-yl)nicotinate (100 mg, 0.30 mmol) in toluene (5 mL) was added 2-(aminomethyl)-1-ethylpyrrolidine (78 mg, 0.61 mmol) and the mixture was cooled to 0° C. under a nitrogen atmosphere. Trimethyl aluminium (0.6 mL, 2 M in hexane, 1.2 mmol) was added dropwise during 5 min and the reaction was heated to 70° C. over night. The reaction was quenched with water and an aqueous saturated NaHCO₃ solution and extracted with chloroform. The combined extracts were dried (Na₂SO₄) and the solvent was evaporated in vacuo. The residue was purified on a silica gel column using chloroform/methanol/conc. NH₃(aq), (80:19:1), as the eluent. Fractions containing product were collected and evaporated in vacuo and dried at 25° C. in a vacuum-cabinet over night. The residue was dissolved in methanol/chloroform and treated with 5 M HCl in diethyl ether. The hydrochloride was dried in vacuo to afford 30 mg (20% yield) of title compound as an orange solid: ¹H NMR (D₂O, 400 MHz) δ 7.65 (s, 1 H), 7.42 (d, J=8 Hz, 1 H), 7.32 (d, J=8 Hz, 1 H), 7.16 (s, 1 H), 6.63 (d, J=9 Hz, 1 H), 6.53 (d, J=8 Hz, 1 H), 3.66-3.52 (m, 4 H), 3.49-3.41 (m, 1 H), 3.13-3.02(m, 2 H), 2.23-2.16 (m, 1 H), 2.05-1.88 (m, 2 H), 1.87-1.76 (m, 1 H), 1.26 (t, J=7 Hz, 3 H).

The following Examples, 93-97, was prepared as described for Example 92:

Example 93

6-(2-Hydroxy-5-nitro-1H-indol-3-yl)-N-(2-morpholin-4-ylethyl)nicotinamide hydrochloride Starting material: 4-(2-aminoethyl)morpholine. The formed hydrochloride was recrystallized from methanol. Yield: 4.1%: ¹H NMR (D₂O, 400 MHz) δ 7.70 (s, 1 H), 7.52 (d, J=9 Hz, 1 H), 7.45 (d, J=8 Hz, 1 H), 7.29 (s, 1 H), 6.78 (d, J=9Hz, 1 H), 6.64 (d, J=8 Hz, 1 H), 4.05-3.75 (m, 4 H), 3.65-3.62 (m, 2 H), 3.50-3.20 (m, 6 H).

Example 94

6-(2-Hydroxy-5-nitro-1H-indol-3-yl)-N-methyl-N-(1-methylpiperidin-4-yl)nicotinamide hydrochloride Starting material: 1-methyl-4-(methylamino)piperidine. The formed hydrochloride was recrystallized from methanol. Yield: 3.3%: MS (ES) m/z 410 (M⁺+1).

Example 95

5-Nitro-3-{5-[(4-pyrrolidin-1-ylpiperidin-1-yl)carbonyl]pyridin-2-yl}-1H-indol-2-ol hydrochloride Starting material: 4-(1-pyrrolidinyl)piperidine. The formed hydrochloride was recrystallized from methanol. Yield: 5.2%: MS (EI, 70 eV) m/z (relative intensity) 435 (M⁺, 1), 298 (6), 282 (7), 207 (5), 174 (14), 154 (17), 124 (17), 110 (100), 98 (75), 84 (26), 70 (61), 52 (23).

Example 96

3-(5-{[3-(Dimethylamino)pyrrolidin-1-yl]carbonyl}pyridin-2-yl)-5-nitro-1H-indol-2-ol hydrochloride Starting material: 3-(dimethylamino)pyrrolidine. The formed hydrochloride was recrystallized from methanol. Yield: 1.5%: ¹H NMR (DMSO-d6, 400 MHz) δ 11.22 (s, 1 H), 8.50 (s, 1 H), 8.29 (s, 1 H), 8.04 (dd, J=9, 2 Hz, 1 H), 7.91 (dd, J=9, 2 Hz, 1 H), 7.73 (d, J=9 Hz, 1 H), 7.05 (d, J=9 Hz, 1 H), 4.05-3.83 (m, 2 H), 3.82-3.70 (m, 2 H), 3.66-3.54 (m, 1 H), 2.80 (br s, 6 H), 2.40-2.29 (m, 1 H), 2.23-2.10 (m, 1 H).

Example 97

N-[2-(Dimethylamino)-1-methylethyl]-6-(2-hydroxy-5-nitro-1H-indol-3-yl)nicotinamide hydrochloride Starting material: 3-(dimethylamino)pyrrolidine. Yield: 3.2%: ¹H NMR (D₂O, 400 MHz) δ 7.85 (s, 1 H), 7.60 (d, J=9 Hz, 1 H), 7.47 (d, J=9 Hz, 1 H), 7.36 (s, 1 H), 6.84 (d, J=9 Hz, 1 H), 6.64 (d, J=9 Hz, 1 H), 4.51-4.40 (m, 1 H), 3.27-3.12 (m, 2 H), 2.88-2.77 (m, 6 H), 1.25 (d, J=6 Hz, 3 H).

Example 98

6-(2-Hydroxy-5-nitro-1H-indol-3-yl)-N-(2-pyrollindin-1-ylethyl)nicotinamide fumarate A solution of ethyl 6-(2-hydroxy-5-nitro-1H-indol-3-yl)nicotinate (200 mg, 0.61 mmol) in 2-pyrrolidin-1-yl-ethylamine (1.5 mL) was heated at 120° C. in a closed vessel for 24 h. The mixture was cooled to room temperature and diluted with water and an aqueous solution of NaHCO$_3$ followed by extraction with chloroform. The phases were separated and evaporated in vacuo. Purification on a silica gel column using chloroform/methanol/conc NH$_3$(aq), (100:15:1.5), as the eluent gave 90 mg (37% yield) of the title compound as the base. The base was converted to the fumarate salt according to the procedure described for Example 103: MS (ES) m/z 396 (M$^+$+1).

Example 99

3-{5-[(4-Methylpiperazin-1-yl)carbonyl]pyridin-2-yl}-5-nitro-1H-indol-2-ol fumarate The title compound was prepared as described for Example 92 using ethyl 6-(2-hydroxy-5-nitro-1H-indol-3-yl)nicotinate (1 eqv), trimethyl aluminium (4 eqv), N-methylpipearzine (2 eqv) and benzene as the solvent. The crude product was purified on a silica gel column using chloroform/methanol/conc NH$_3$(aq), (100:12:1.2), as the eluent. Yield: 69% of the title compound as the base. The base was converted to the fumarate salt according to the procedure described for Example 103: MS (ES) m/z 382 (M$^+$+1).

Example 100

6-(5-Cyano-2-hydroxy-1H-indol-3-yl)-N-(2-pyrrolidin-1-ylethyl)nicotinamide fumarate The title compound was prepared as described for Example 98 using ethyl 6-(2-hydroxy-5-cyano-1H-indol-3-yl)nicotinate and 2-pyrrolidin-1-yl-ethylamine. Yield: 13% of the title compound: $^1$H NMR (on the base, CDCl$_3$, 300 MHz) δ 10.8 (br s, 1 H), 8.80-8.52 (m, 2 H), 8.18-7.86 (m, 3 H), 7.35-7.18 (m, 1 H), 6.98 (d, J=7 Hz, 1 H), 6.55 (s, 1 H), 3.60-3.35 (m, 2 H), 2.83 (m, 6 H), 1.80 (br s, 4 H).

Example 101

6-(5-Cyano-2-hydroxy-1H-indol-3-yl)-N-methyl-N-(2-pyrrolidin-1-ylethyl)pyridine-3-sulfonamide hydrochloride To an ice-cooled solution of 5-cyanooxindole (200 mg, 1.26 mmol) in N,N-dimethylformamide (5 mL) was added sodium hydride (60 mg, 1.5 mmol). The reaction mixture was stirred for 25 min whereafter 6-chloro-N-methyl-N-(2-pyrrolidin-1-ylethyl)pyridine-3-sulfonamide (303 mg, 1 mmol) was added. The reaction mixture was heated at 130° C. for 1 h and then allowed to cool to room temperature. An aqueous saturated solution of NaHCO$_3$ (50 mL) was added and the water phase was extracted with ethyl acetate. The organic phase was dried (Na$_2$SO$_4$) and purified on a silica gel column using chloroform/methanol/conc NH$_3$(aq), (500:35:3.5 to 500:50:5), as the eluent. The solvents were evaporated in vacuo and the residue was stirred over night in ethyl acetate, filtered and dried to give 160 mg (38% yield) of the title compound as the base. The base, dissolved in chloroform/methanol, was treated with HCl in diethyl ether to give the title compound: MS (ES) m/z 426 (M$^+$+1).

Example 102

6-(5-Cyano-2-hydroxy-1H-indol-3-yl)-N-[2-(dimethylamino)ethyl]pyridine-3-sulfonamide fumarate The title compound was prepared as described for Example 101 using 6-chloro-N-[2-(dimethylamino)ethyl]pyridine-3-sulfonamide and 5-cyanooxindole. The crude product was purified on a silica gel column using chloroforn/methanol/conc NH$_3$(aq), (100:10:1), as the eluent followed by another purification on a silica gel column using chloroform/methanol/conc NH$_3$(aq), (100:7:0.7), as the eluent. The base was converted to the fumarate salt according to the procedure described for Example 103: Yield: 20%: MS (ES) m/z 386 (M$^+$+1).

Example 103

6-(5-Cyano-2-hydroxy-1H-indol-3-yl)-N-[2-(dimethylamino)ethyl]-N-ethylpyridine-3-sulfonamide fumarate The title compound was prepared as described for Example 101 using 6-chloro-N-[2-(dimethylamino)ethyl]-N-ethylpyridine-3-sulfonamide and 5-cyanooxindole. The crude product was purified on a silica gel column using chloroform/methanol/conc NH$_3$(aq), (100:10:1), as the eluent: MS (ES) m/z 414 (M$^+$+1). The base was dissolved in chloroform (15 mL) and methanol (2 mL) and fumaric acid dissolved in methanol (2 mL) was added. Diethyl ether (20 mL) was added and the formed precipitate was filtered and dried to give the title compound. Yield: 10%: MS (ES) m/z 414 (M$^+$+1).

Example 104

6-(5-Cyano-2-hydroxy-1H-indol-3-yl)-N-[(1-ethylpyrrolidin-2-yl)methyl]pyridine-3-sulfonamide fumarate The title compound was prepared as described for Example 101 using 6-chloro-N-[(1-ethylpyrrolidin-2-yl)methyl]pyridine-3-sulfonamide and 5-cyanooxindole. The crude product was purified on a silica gel column using chloroform/methanol/conc NH$_3$(aq), (100:18:1.8), as the eluent. Yield: 50%: MS (ES) m/z 426 (M$^+$+1). The base was converted to the fumarate salt according to the procedure described for Example 103.

Example 105

2-Hydroxy-3-{5-[(4-methyl-1,4-diazepan-1-yl)sulfonyl]pyridin-2-yl}-1H-indole-5-carbonitrile fumarate The title compound was prepared as described for Example 101 using 1-[(6-chloropyridin-3-yl)sulfonyl]-4-methyl-1,4-diazepane and 5-cyanooxindole. The crude product was purified on a silica gel column using chloroform/methanol/conc NH$_3$(aq), (100:15:1.5), as the eluent. Yield: 50%: MS (ES) m/z 412 (M$^+$+1). The base was converted to the fumarate salt according to the procedure described for Example 103.

Example 106

2-Hydroxy-3-[5-(morpholin-4-ylsulfonyl)pyridin-2-yl]-1H-indole-5-carbonitrile The title compound was prepared as described for Example 101 using 4-[(6-chloropyridin-3-yl)sulfonyl]morpholine and 5-cyanooxindole. The reaction mixture was quenched with water and the solvents were evaporated in vacuo. Water was added and the mixture was filtered. The solid material was washed with water, methanol, ethyl acetate and diethyl ether to give the title compound. Yield: 44%: MS (ES) m/z 385 ($M^+$+1).

Example 107

3-{5-[(4-Methylpiperazin-1-yl)sulfonyl]pyridin-2-yl}-5-(2-methyl-1,3-thiazol-4-yl)-1H-indol-2-ol hydrochloride The title compound was prepared as described for Example 101 using 1-[(6-chloropyridin-3-yl)sulfonyl]4-methylpiperazine (described in: Thunus L., *Annales Pharmaceutiques Francaises* 1977, 35, 197-203) and 5-(2-methyl-1,3-thiazol-4-yl)-1,3-dihydro-2H-indol-2-one. The crude product was purified on a silica gel column using chloroform/methanol/conc $NH_3$(aq), (50:3:0.3), as the eluent. The base was dissolved in chloroform/methanol and converted to the hydrochloride salt using HCl in diethyl ether (1 M). Yield: 35% of the title compound: MS (ES) m/z 470 ($M^+$+1).

Example 108

3-{5-[(4-Methylpiperazin-1-yl)sulfonyl]pyridin-2-yl}-5-(1,3-thiazol-4-yl)-1H-indol-2-ol fumarate The title compound was prepared as described for Example 101 using 1-[(6-chloropyridin-3-yl)sulfonyl]-4-methylpiperazine (described in: Thunus L., *Annales Pharmaceutiques Francaises* 1977, 35, 197-203) and 5-(1,3-thiazol4-yl)-1,3-dihydro-2H-indol-2-one. The crude product was purified on a silica gel column using chloroform/methanol/conc $NH_3$(aq), (100:7:0.7), as the eluent. The base was converted to the fumarate salt according to the procedure described for Example 103: Yield: 8% of the title compound: MS (ES) m/z 456 ($M^+$+1).

Example 109

3-{5-[(4-Methylpiperazin-1-yl)sulfonyl]pyridin-2-yl}-5-(1,3-oxazol-5-yl)-1H-indol-2-ol The title compound was prepared as described for Example 101 using 1-[(6-chloropyridin-3-yl)sulfonyl]-4-methylpiperazine (described in: Thunus L., *Annales Pharmaceutiques Francaises* 1977, 35, 197-203) and 5-(1,3-oxazol-5-yl)-1,3-dihydro-2H-indol-2-one. The crude product was purified on a silica gel column using chloroform/methanol/conc $NH_3$(aq), (100:10:1), as the eluent followed by trituration in ethyl acetate. Yield: 1% of the title compound: MS (ES) m/z 441 ($M^+$+1).

Example 110

3-[5-(Morpholin-4-ylmethyl)pyridin-2-yl]-5-nitro-1H-indol-2-ol hydrochloride To a suspension of sodium hydride (60% dispersion in oil, 0.048 g, 1.19 mmol, pre-washed with hexane) in N,N-dimethylformamide (2.0 mL) was added 5-nitrooxindole (0.185 g, 1.04 mmol). The formed mixture was stirred for 5 min at room temperature and 2-chloro-5-(morpholin-4-ylmethyl)pyridine 1-oxide (0.16 g, 0.7 mmol) was added. The resulting reaction mixture was stirred for 30 minutes at 130° C. ($N_2$ atmosphere). The solvent was removed in vacuo and the residual oil was purified on a silica gel column using chloroform/methanol, (10:1) as the eluent affording the N-oxide product. The N-oxide was dissolved in chloroform (2 mL) and phosphorous trichloride (0.385 g, 2.80 mmol) was added. The reaction mixture was stirred for 30 min at 60° C. followed by extraction with an aqueous saturated $NaHCO_3$ solution. The organic layer was dried ($Na_2SO_4$) and concentrated to a yellowish red oil which was purified on a silica gel column using chloroform/methanol, (10:1) as the eluent to give 10 mg (4% yield) of the title compound as the free base as an yellow solid. The base (10 mg, 0.028 mmol) was dissolved in methylene chloride/methanol, (1:1) and treated with 1 M HCl in diethyl ether at 0° C. The resulting yellowish orange crystals were collected by filtration and washed with diethyl ether to obtain 2 mg (16% yield) of the title compound: $^1$H NMR (DMSO-d6, 400 MHz) δ 11.23 (s, 1 H), 10.83 (br s, 1 H), 8.36 (s, 2 H), 8.10 (dd, J=10, 2 Hz, 1 H), 7.94 (dd, J=9,2 Hz, 1 H), 7.87 (d, J=10 Hz, 1 H), 7.09 (d, J=9 Hz, 1 H), 4.34 (s, 2 H), 4.02 (d, J=13 Hz, 2 H), 3.77 (t, J=12 Hz, 2 H), 3.38 (d, J=11 Hz, 2 H), 3.14 (d, J=10 Hz, 2 H).

Pharmacology

Determination of ATP Competition in Scintillation Proximity GSK3β Assay

GSK3β Scintillation Proximity Assay.

The competition experiments were carried out in duplicate with 10 different concentrations of the inhibitors in clear-bottom microtiter plates (Wallac, Finland). A biotinylated peptide substrate, Biotin-Ala-Ala-Glu-Glu-Leu-Asp-Ser-Arg-Ala-Gly-Ser($PO_3H_2$)-Pro-Gln-Leu (AstraZeneca, Lund), was added at a final concentration of 1 μM in an assay buffer containing 1 mU recombinant human GSK3β (Dundee University, UK), 12 mM morpholinepropanesulfonic acid (MOPS), pH 7.0, 0.3 mM EDTA, 0.01% β-mercaptoethanol, 0.004% Brij 35 (a natural detergent), 0.5% glycerol and 0.5 μg BSA/25 μl. The reaction was initiated by the addition of 0.04 μCi [γ-$^{33}$P]ATP (Amersham, UK) and unlabelled ATP at a final concentration of 1 μM and assay volume of 25 μl. After incubation for 20 minutes at room temperature, each reaction was terminated by the addition of 25 μl stop solution containing 5 mM EDTA, 50 μM ATP, 0.1% Triton X-100 and 0.25 mg streptavidin coated Scintillation Proximity Assay (SPA) beads (Amersham, UK). After 6 hours the radioactivity was determined in a liquid scintillation counter (1450 MicroBeta Trilux, Wallac). The inhibition curves were analysed by non-linear regression using GraphPad Prism, USA. The $K_m$ value of ATP for GSK3β, used to calculate the inhibition constants ($K_i$) of the various compounds, was 20 μM.

The following abbreviations have been used:

| | |
|---|---|
| MOPS | Morpholinepropanesulfonic acid |
| EDTA | Ethylenediaminetetraacetic acid |
| BSA | Bovin Serum Albumin |
| ATP | Adenosine Triphosphate |
| SPA | Scintillation Proximity Assay |
| GSK3 | Glycogen synthase kinase 3 |
| MP-Carbonate | Macroporous triethylamonium methylpolystyrene carbonate |
| PS-Diisopropylethylamine | N,N-(Diisopropyl)aminomethylpolystyrene |
| PS-Thiophenol | 3-(3-Mercaptophenyl)propanamidomethylpolystyrene |
| PS-Isocyanate | Polystyrene methylisocyanate |

Results

Typical $K_i$ values for the compounds of the present invention are in the range of about 0.001 to about 10,000 nM. Other values for $K_i$ are in the range of about 0.001 to about 1000 nM. Further values for $K_i$ are in the range of about 0.010 nM to about 300 nM.

The invention claimed is:
1. A compound of formula Ia,

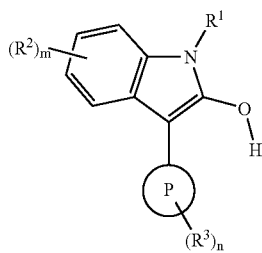

wherein the compound is in the form of a base or a pharmaceutically acceptable salt thereof, and
wherein:
P is a 6-membered ring containing one nitrogen;
$R^1$ hydrogen;
$R^2$ is $C_{0-6}$alkylcyano;
$R^3$ is $C_{0-6}$alkylNR$^4$R$^5$;
m is 1;
n is 1;
$R^4$ is selected from the group consisting of hydrogen, $C_{1-6}$alkyl, $C_{2-6}$alkenyl, $C_{2-6}$alkynyl, $C_{0-6}$alkylC$_{3-6}$cycloalkyl, $C_{0-6}$alkylaryl, $C_{0-6}$alkylheteroaryl, $C_{1-6}$alkylNR$^{14}$R$^{15}$, and a 5- or 6-membered heterocyclic group containing one or two heteroatoms independently selected from N, O, and S, wherein the heterocyclic group is optionally substituted by a group Y;
$R^5$ is selected from the group consisting of hydrogen, $C_{1-6}$alkyl, $C_{2-6}$alkenyl, $C_{2-6}$alkynyl, $C_{0-6}$alkylC$_{3-6}$cycloalkyl, $C_{0-6}$alkylaryl, $C_{0-6}$alkylheteroaryl, and $C_{1-6}$alkylNR$^{14}$R$^{15}$;
or $R^4$ and $R^5$ together with the N to which they are attached may form a 6-membered heterocyclic group containing one nitrogen and one oxygen; and
wherein any $C_{1-6}$alkyl, $C_{2-6}$alkenyl, $C_{2-6}$alkynyl, $C_{0-6}$alkylC$_{3-6}$cycloalkyl, $C_{0-6}$alkylaryl, and $C_{0-6}$alkylheteroaryl group defined under $R^2$ to $R^5$ is optionally substituted by one or more groups Z;
$R^{14}$ and $R^{15}$ are independently selected from hydrogen, $C_{1-6}$alkyl, and $C_{0-6}$alkylC$_{3-6}$cycloalkyl, wherein $R^{14}$ and $R^{15}$ optionally together form a 5- or 6-membered heterocyclic group containing one or more heteroatoms independently selected from N, O, and S, wherein the heterocyclic group is optionally substituted by a group Y;
Z is independently selected from the group consisting of oxo, halogen, nitro, CN, OR$^{16}$, $C_{1-6}$alkyl, $C_{0-6}$alkylaryl, $C_{0-6}$alkylC$_{3-6}$cycloalkyl, fluoromethyl, difluoromethyl, trifluoromethyl, fluoromethoxy, difluoromethoxy, trifluoromethoxy, OC$_{1-6}$alkylNR$^{16}$R$^{17}$, NR$^{16}$R$^{17}$, CONR$^{16}$R$^{17}$, NR$^{16}$(CO)R$^{17}$, O(CO)C$_{1-6}$alkyl, (CO)OC$_{1-6}$alkyl, COR$^{16}$, (SO$_2$)NR$^{16}$R$^{17}$, SO$_2$R$^{16}$, SOR$^{16}$, (CO)C$_{1-6}$alkylNR$^{16}$R$^{17}$, (SO$_2$)C$_{1-6}$alkylNR$^{16}$R$^{17}$, phenyl, heteroaryl, and a 5- or 6-membered heterocyclic group containing one or two heteroatoms independently selected from N, O, and S, wherein the phenyl, heteroaryl, and heterocyclic groups are optionally substituted by a group Y;
Y is selected from the group consisting of oxo, halogen, nitro, CN, OR$^{16}$, $C_{1-6}$alkyl, $C_{0-6}$alkylaryl, $C_{0-6}$alkylC$_{3-6}$cycloalkyl, fluoromethyl, difluoromethyl, trifluoromethyl, fluoromethoxy, difluoromethoxy, trifluoromethoxy, OC$_{1-6}$alkylNR$^{16}$R$^{17}$, NR$^{16}$R$^{17}$, CONR$^{16}$R$^{17}$, NR$^{16}$(CO)R$^{17}$, O(CO)C$_{1-6}$alkyl, (CO)OC$_{1-6}$alkyl, COR$^{16}$, (SO$_2$)NR$^{16}$R$^{17}$, SO$_2$R$^{16}$, SOR$^{16}$, (CO)C$_{1-6}$alkylNR$^{16}$R$^{17}$, (SO$_2$)C$_{1-6}$alkylNR$^{16}$R$^{17}$, phenyl, $C_{0-6}$alkylaryl, and heteroaryl, wherein the phenyl, $C_{0-6}$alkylaryl, and heteroaryl groups are optionally substituted with one or more substituents selected from the group consisting of halogen, nitro, CN, OR$^{16}$, $C_6$alkyl, fluoromethyl, difluoromethyl, trifluoromethyl, fluoromethoxy, difluoromethoxy, and trifluoromethoxy;
$R^{16}$ and $R^{17}$ are independently selected from hydrogen and $C_{1-6}$alkyl, and
wherein $R^{16}$ and $R^{17}$ optionally together form a 5- or 6-membered heterocyclic group containing one or more heteroatoms independently selected from N, O, and S.
2. A compound according to claim 1, wherein:
$R^5$ is $C_{1-6}$alkylNR$^{14}$R$^{15}$, and
$R^4$ selected from hydrogen, $C_{1-6}$alkyl; or
$R^4$ and $R^5$ together with the N to which they are attached form a 6-membered heterocyclic group containing one or more heteroatoms selected independently from N and O, wherein said heterocyclic group may optionally be substituted by a group Y;
and wherein $R^{14}$ and $R^{15}$ may together form a 5-membered heterocyclic group containing one or more heteroatoms, selected independently from N, and O;
Y is selected from $C_{1-6}$alkyl, $C_{0-6}$alkylaryl, NR$^{16}$R$^{17}$, phenyl, wherein the phenyl may be optionally substituted with nitro and trifluoromethyl;
wherein $R^{16}$ and $R^{17}$ may together form a 5-membered heterocyclic group containing one N heteroatom.

3. A compound according to claim 1, wherein P is pyridyl; $R^2$ is CN; $R^3$ is $C_{0-6}$alkylNR$^4$R$^5$; wherein $R^4$ and $R^5$ may together form a 5- or 6-membered heterocyclic group containing one or more heteroatoms selected independently from N and O.

4. A compound according to claim 3, wherein $R^4$ and $R^5$ together form a 6-membered heterocyclic group containing one or more heteroatoms selected independently from N and O.

5. A compound selected from:
2-Hydroxy-3-{5-[(4-methylpiperazin-1-yl)carbonyl]pyridin-2-yl}-1H-indole-5-carbonitrile;
2-Hydroxy-3-[6-(2-morpholin-4-ylethoxy)pyrimidin-4-yl]-1H-indole-5-carbonitrile;
3-(5-{[3-(Dimethylamino)pyrrolidin-1-yl]methyl}pyridin-2-yl)-2-hydroxy-1H-indole-5-carbonitrile;
2-Hydroxy-3-{5-[(4-methylpiperidin-1-yl)methyl]pyridin-2-yl}-1H-indole-5-carbonitrile;
3-[5-(Azetidin-1-ylmethyl)pyridin-2-yl]-2-hydroxy-1H-indole-5-carbonitrile;
2-Hydroxy-3-[5-(piperidin-1-ylmethyl)pyridin-2-yl]-1H-indole-5-carbonitrile;
3-[5-(Morpholin-4-ylcarbonyl)pyridin-2-yl]-5-nitro-1H-indol-2-ol, or
2-Hydroxy-3-[5-(morpholin-4-ylsulfonyl)pyridin-2-yl]-1H-indole-5-carbonitrile;
or a pharmaceutically acceptable salt thereof.

6. A compound selected from:
2-Hydroxy-3-{4-[(4-methylpiperazin-1-yl)carbonyl]pyridin-2-yl}-1H-indole-5-carbonitrile;
2-Hydroxy-3-{5-[(4-methylpiperazin-1-yl)methyl]pyridin-2-yl}-1H-indole-5-carbonitrile;
2-Hydroxy-3-{5-[(4-methylpiperazin-1-yl)sulfonyl]pyridin-2-yl}-1H-indole-5-carbonitrile;
2-Hydroxy-3-[5-(pyrrolidin-1-ylmethyl)pyridin-2-yl]-1H-indole-5-carbonitrile;
2-Hydroxy-3-{5-[(4-methyl-1,4-diazepan-1-yl)methyl]pyridin-2-yl}-1H-indole-5-carbonitrile;
2-Hydroxy-3-{5-[(4-pyrrolidin-1-yl)piperidin-1-yl)methyl]pyridin-2-yl}-1H-indole-5-carbonitrile;
3-{5-[(4-Methylpiperazin-1-yl)sulfonyl]pyridin-2-yl}-1H-indol-2-ol;
6-Chloro-3-{5-[(4-methylpiperazin-1-yl)sulfonyl]pyridin-2-yl}-1H-indol-2-ol;
6-Bromo-3[-5-(morpholin-4-ylmethyl)pyridin-2-yl]-1H-indol-2-ol;
5-Bromo-3[-5-(morpholin-4-ylmethyl)pyridin-2-yl]-1H-indol-2-ol;
3-Fluoro-3[-5-(morpholin-4-ylmethyl)pyridin-2-yl]-2-oxoindoline-6-carbonitrile;
3-{5-[(4-Benzylpiperazin-1-yl)sulfonyl]pyridin-2-yl}-2-hydroxy-1H-indole-5-carbonitrile;
2-Hydroxy-3-{5-[(4-isopropylpiperazin-1-yl)sulfonyl]pyridin-2-yl}-1H-indole-5-carbonitrile;
3-{5-[(4-Ethylpiperazin-1-yl)sulfonyl]pyridin-2-yl}-2-hydroxy-1H-indole-5-carbonitrile;
3-[5-(Morpholin-4-ylmethyl)pyridin-2-yl]-5-thien-2-yl-1H-indol-2-ol;
5-(2-Furyl)-3[-5-(morpholin-4-ylmethyl)pyridin-2-yl]-1H-indol-2-ol;
3-{3-Bromo-5-[(4-methylpiperazin-1-yl)sulfonyl]pyridin-2-yl}-5-nitro-1H-indol-2-ol;
3-[5-(Morpholin-4-ylmethyl)pyridin-2-yl]-5-(trifluoromethyl)-1H-indol-2-ol;
6-(2-Hydroxy-5-nitro-1H-indol-3-yl)-N-(2-morpholin-4-ylethyl)nicotinamide;
6-(2-Hydroxy-5-nitro-1H-indol-3-yl)-N-methyl-N-(1-methylpiperidin-4-yl)nicotinamide;
5-Nitro-3-{5-[(4-pyrrolidin-1-ylpiperidin-1-yl)carbonyl]pyridin-2-yl}-1H-indol-2-ol;
3-(5-{[3-(Dimethylamino)pyrrolidin-1-yl]carbonyl}pyridin-2-yl)-5-nitro-1H-indol-2-ol;
6-(5-Cyano-2-hydroxy-1H-indol-3-yl)-N-methyl-N-(2-pyrrolidin-1-ylethyl)pyridine-3-sulfonamide;
3-{5-[(4-Methylpiperazin-1-yl)sulfonyl]pyridin-2-yl}-5-(2-methyl-1,3-thiazol-4-yl)-1H-indol-2-ol;
3-[5-(Morpholin-4-ylmethyl)pyridin-2-yl]-5-nitro-1H-indol-2-ol;
6-(5-Cyano-2-hydroxy-1H-indol-3-yl)-N-(2-pyrrolidin-1-ylethyl)pyridine-3-sulfonamide;
2-Hydroxy-3-[5-(morpholin-4-ylmethyl)pyridin-2-yl]-1H-indole-5-carbonitrile;
2-Hydroxy-3-[5-(morpholin-4-ylmethyl)pyridin-2-yl]-1H-indole-6-carbonitrile;
5,6-Dibromo-3-[5-(morpholin-4-ylmethyl)pyridin-2-yl]-1H-indol-2-ol, or
2-Hydroxy-3-{5-[(4-methylpiperazin-1-yl)sulfonyl]pyridin-2-yl}-1H-indole-6-carbonitrile; p1 or a pharmaceutically acceptable salt thereof.

7. A hydrochloride salt of a compound according to claim 6.

8. 6-(2-Hydroxy-5-nitro-1H-indol-3-yl)-N-(2-pyrollindin-1-ylethyl)nicotinamide;
6-(5-Cyano-2-hydroxy-1H-indol-3-yl)-N-(2-pyrrolidin-1-ylethyl)nicotinamide;
2-Hydroxy-3-(5-[(4-methyl-1,4-diazepan-1-yl)sulfonyl]pyridin-2-yl}-1H-indole-5-carbonitrile;
3-{5-[(4-Methylpiperazin-1-yl)sulfonyl]pyridin-2-yl}-5-(1,3-thiazol-4-yl)-1H-indol-2-ol, or
3-{5-[(4-Methylpiperazin-1-yl)carbonyl]pyridin-2-yl}-5-nitro-1H-indol-2-ol;
or a pharmaceutically acceptable salt thereof.

9. A fumarate salt of a compound according to claim 8.

10. A compound that is 2-Hydroxy-3-{5-[(4-phenylpiperazin-1-yl)methyl]pyridin-2-yl}-1H-indole-5-carbonitrile or a pharmaceutically acceptable salt thereof.

11. A compound that is 2-Hydroxy-3-[5-({4-[2-nitro-4-(trifluoromethyl)phenyl]piperazin-1-yl}methyl)pyridin-2-yl]-1H-indole-5-carbonitrile or a pharmaceutically acceptable salt thereof.

12. A compound that is 2-Hydroxy-3[-5-(morpholin-4-ylmethyl)pyridin-2-yl]-1H-indole-5-carbonitrile or a pharmaceutically acceptable salt thereof.

13. A compound that is 3[-5-(Morpholin-4-ylmethyl)pyridin-2-yl]-5-pyridin-3-yl-1H-indol-2-ol or a pharmaceutically acceptable salt thereof.

14. A compound that is 3-{5-[(4-Methylpiperazin-1-yl)sulfonyl]pyridin-2-yl}-5-(1,3-oxazol-5-yl)-1H-indol-2-ol or a pharmaceutically acceptable salt thereof.

15. A pharmaceutical formulation comprising as active ingredient a therapeutically effective amount of a compound according to any one of claims 5-14 in association with at least one pharmaceutically acceptable carrier or diluent.

* * * * *